(12) United States Patent
Ohgi et al.

(10) Patent No.: US 9,528,111 B2
(45) Date of Patent: *Dec. 27, 2016

(54) SINGLE-STRANDED NUCLEIC ACID MOLECULE HAVING AMINO ACID BACKBONE

(71) Applicant: BONAC CORPORATION, Kurume-shi, Fukuoka (JP)

(72) Inventors: Tadaaki Ohgi, Kurume (JP); Hiroshi Suzuki, Itami (JP); Tomohiro Hamasaki, Kurume (JP); Eriko Aoki, Kurume (JP)

(73) Assignee: Bonac Corporation, Kurume (JP)

( * ) Notice: Subject to any disclaimer, the term of this patent is extended or adjusted under 35 U.S.C. 154(b) by 21 days.

This patent is subject to a terminal disclaimer.

(21) Appl. No.: 14/362,762

(22) PCT Filed: Dec. 29, 2012

(86) PCT No.: PCT/JP2012/084247
§ 371 (c)(1),
(2) Date: Jun. 4, 2014

(87) PCT Pub. No.: WO2013/103146
PCT Pub. Date: Jul. 11, 2013

(65) Prior Publication Data
US 2014/0329886 A1 Nov. 6, 2014

(30) Foreign Application Priority Data

Jan. 7, 2012 (JP) ................... 2012-001711
Feb. 9, 2012 (JP) ................... 2012-026745

(51) Int. Cl.
| | | |
|---|---|---|
| C12N 15/11 | (2006.01) | |
| C12N 15/113 | (2010.01) | |
| C07C 225/06 | (2006.01) | |
| A61K 47/48 | (2006.01) | |

(52) U.S. Cl.
CPC ..... *C12N 15/1136* (2013.01); *A61K 47/48215* (2013.01); *C07C 225/06* (2013.01); *C12N 15/111* (2013.01); *C12N 2310/14* (2013.01); *C12N 2310/3181* (2013.01); *C12N 2310/531* (2013.01); *C12N 2310/532* (2013.01); *C12N 2310/533* (2013.01); *C12N 2320/30* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 4,550,163 A | 10/1985 | Voss et al. | |
| 2003/0077608 A1 | 4/2003 | Coull et al. | |
| 2003/0232355 A1* | 12/2003 | Norden | B82Y 5/00 435/6.14 |
| 2004/0058886 A1 | 3/2004 | Scaringe | |
| 2004/0241855 A1* | 12/2004 | Cullis | A61K 9/1272 435/455 |
| 2005/0053979 A1 | 3/2005 | Livak et al. | |
| 2005/0233455 A1 | 10/2005 | Damha et al. | |
| 2006/0276421 A1 | 12/2006 | Kunugiza et al. | |
| 2009/0005332 A1 | 1/2009 | Hauser et al. | |
| 2010/0317714 A1 | 12/2010 | Xi et al. | |

FOREIGN PATENT DOCUMENTS

| | | | |
|---|---|---|---|
| DE | 873543 | 4/1953 | |
| DE | WO 2011009624 A1 * | 1/2011 | ....... A61K 47/48092 |
| JP | 2004-524032 A | 8/2004 | |
| JP | 2005-508634 A | 4/2005 | |
| JP | 2007-516695 A | 6/2007 | |
| JP | 2008-526213 A | 7/2008 | |
| JP | 2011-504730 A | 2/2011 | |
| WO | WO 2004/015075 A2 | 2/2004 | |
| WO | WO 2005/030960 A1 | 4/2005 | |
| WO | WO 2009/076321 A2 | 6/2009 | |

OTHER PUBLICATIONS

Hamazaki et al, Inhibition of Influenza Virus Replication in MDCK Cells by Circular Dumbbell RNA/DNA Chimeras with Closed Alkyl Loop Structures, 2002, Helvetica Chimica Acta, vol. 85, 2183-2194.*
Abe et al., *Bioconjugate Chemistry*, 22: 2082-2092 (2011).
De La Torre et al., *Helvetica Chimica Acta*, 85: 2594-2607 (2002).
Fire et al., *Nature*, 391: 806-811 (1998).
Japanese Patent Office, International Search Report in International Application No. PCT/JP2012/084247 (Apr. 16, 2013).
Bradshaw et al., *Journal of Organic Chemistry*, 53(8): 1808-1810 (1988).
Collins et al., *British Journal of Pharmacology*, 13(3): 238-243 (1958).
Gatto et al., *Journal of Organic Chemistry*, 51(26): 5373-5384 (1986).

(Continued)

*Primary Examiner* — Kate Poliakova-Georgantas
(74) *Attorney, Agent, or Firm* — Leydig, Voit & Mayer, Ltd.

(57) ABSTRACT

The invention provides a single-stranded nucleic acid molecule containing an expression inhibitory sequence that inhibits expression of a target gene, region (X), linker region (Lx), and region (Xc), wherein the linker region (Lx) is linked between the region (Xc) and the region (Xc), the region (Xc) is complementary to the region (X), at least one of the region (X) and the region (Xc) contains the expression inhibitory sequence, and the linker region (Lx) contains an atomic group derived from an amino acid. The single-stranded nucleic acid molecule can inhibit expression of the target gene.

31 Claims, 9 Drawing Sheets

(56) References Cited

OTHER PUBLICATIONS

Graubaum et al., *J. Prakt. Chem.*, 337(1): 534-537 (1995).
Maeda et al., *Bulletin of the Chemical Society of Japan*, 56(10): 3073-3077 (1983).
European Patent Office, Supplementary European Search Report in European Patent Application No. 12864101 (Sep. 1, 2015).
Bailén et al., *Tetrahedron Letters*, 42(30): 5013-5016 (2001).
Dankwardt, *Synlett*, 1998(7): 761 (Jul. 1998).
Hoogerhout et al., *Tetrahedron Letters*, 28(14): 1553-1556 (1987).
Ihara et al., *Journal of Organic Chemistry*, 45(9): 1623-1625 (1980).
Sommer et al., *Journal of Medicinal Chemistry*, 9(1): 84-88 (1966).

\* cited by examiner

Fig. 1
(A)
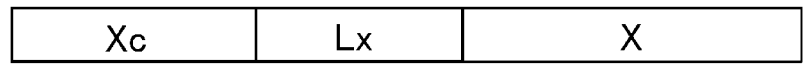
(B)
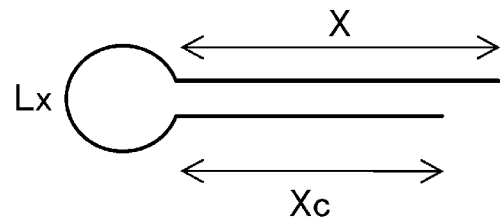
Fig. 2
(A)
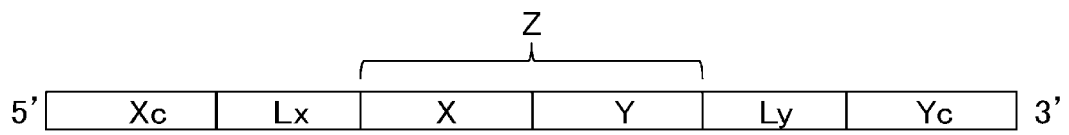
(B)
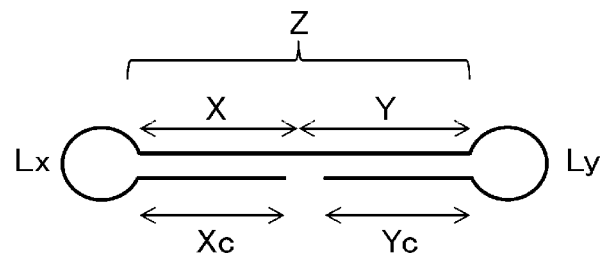

Fig. 3
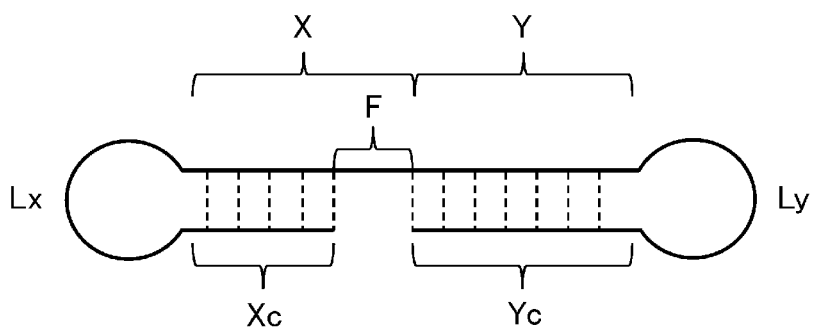
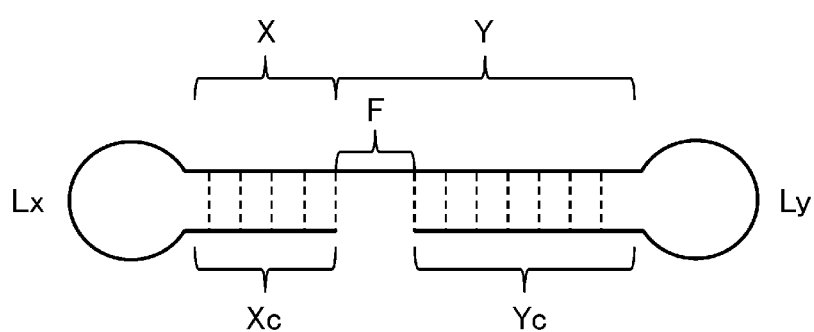
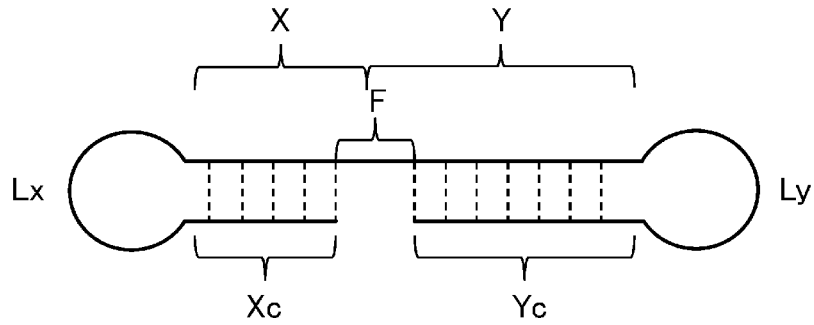
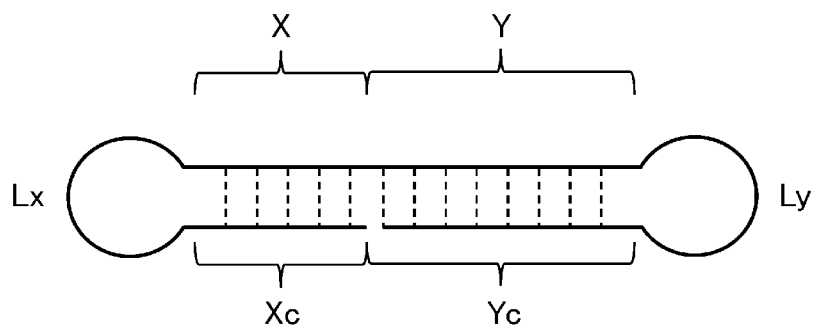

Fig. 5

| | Xc/Yc | | |
|---|---|---|---|
| NK-0036 | 25/1 | 5'- aaccaugagaaguaugacaacagccCACACCGGCUGUUGUCAUACUUCUCAUGGUUCUUCg -3' | 24 |
| NK-0025 | 24/1 | 5'- accaugagaaguaugacaacagccCACACCGGCUGUUGUCAUACUUCUCAUGGUUCUUCg -3' | 25 |
| NK-0037 | 23/2 | 5'- ccaugagaaguaugacaacagccCACACCGGCUGUUGUCAUACUUCUCAUGGUUCUUCga -3' | 26 |
| NK-0016 | 22/3 | 5'- caugagaaguaugacaacagccCACACCGGCUGUUGUCAUACUUCUCAUGGUUCUUCgaa -3' | 27 |
| NK-0038 | 21/4 | 5'- augagaaguaugacaacagccCACACCGGCUGUUGUCAUACUUCUCAUGGUUCUUCgaac -3' | 28 |
| NK-0026 | 20/5 | 5'- ugagaaguaugacaacagccCACACCGGCUGUUGUCAUACUUCUCAUGGUUCUUCgaacc -3' | 29 |
| NK-0027 | 18/7 | 5'- agaaguaugacaacagccCACACCGGCUGUUGUCAUACUUCUCAUGGUUCUUCgaaccau -3' | 30 |
| NK-0028 | 16/9 | 5'- aaguaugacaacagccCACACCGGCUGUUGUCAUACUUCUCAUGGUUCUUCgaaccauga -3' | 31 |
| NK-0029 | 14/11 | 5'- guaugacaacagccCACACCGGCUGUUGUCAUACUUCUCAUGGUUCUUCgaaccaugaga -3' | 32 |
| NK-0014 | 12/13 | 5'- augacaacagccCACACCGGCUGUUGUCAUACUUCUCAUGGUUCUUCgaaccaugagaag -3' | 33 |
| NK-0030 | 9/16 | 5'- acaacagccCACACCGGCUGUUGUCAUACUUCUCAUGGUUCUUCgaaccaugagaaguau -3' | 34 |
| NK-0031 | 7/18 | 5'- aacagccCACACCGGCUGUUGUCAUACUUCUCAUGGUUCUUCgaaccaugagaaguauga -3' | 35 |
| NK-0020 | 5/20 | 5'- cagccCACACCGGCUGUUGUCAUACUUCUCAUGGUUCUUCgaaccaugagaaguaugaca -3' | 36 |
| NK-0019 | 4/21 | 5'- agccCACACCGGCUGUUGUCAUACUUCUCAUGGUUCUUCgaaccaugagaaguaugacaa -3' | 37 |
| NK-0018 | 3/22 | 5'- gccCACACCGGCUGUUGUCAUACUUCUCAUGGUUCUUCgaaccaugagaaguaugacaac -3' | 38 |
| NK-0039 | 2/23 | 5'- ccCACACCGGCUGUUGUCAUACUUCUCAUGGUUCUUCgaaccaugagaaguaugacaaca -3' | 39 |
| NK-0032 | 1/24 | 5'- cCACACCGGCUGUUGUCAUACUUCUCAUGGUUCUUCgaaccaugagaaguaugacaacag -3' | 40 |
| NK-0040 | 1/25 | 5'- CACACCGGCUGUUGUCAUACUUCUCAUGGUUCUUCgaaccaugagaaguaugacaacagc -3' | 41 |

Fig. 9

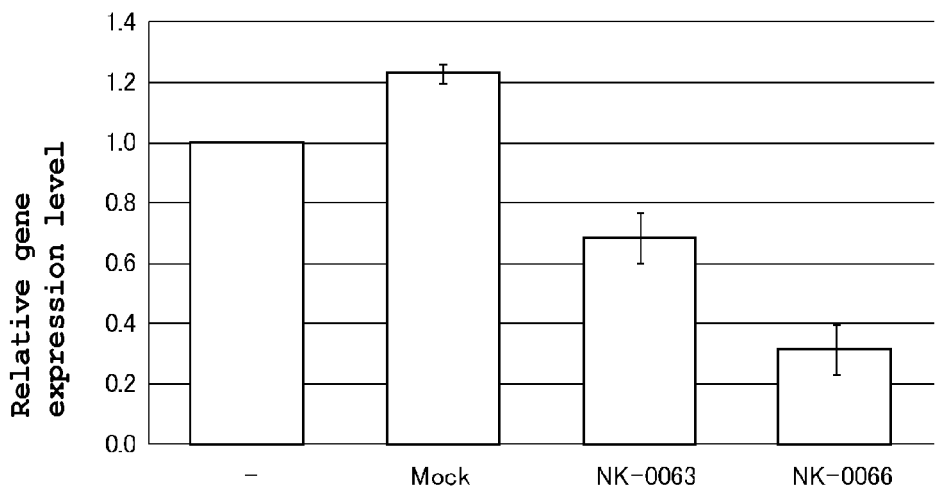

Fig. 10

| | Xc+Yc/X+Y | | |
|---|---|---|---|
| NK-0047 | 26/27 | 5'- aaccaugagaaguaugacaacagccCCACACCGGCUGUUGUCAUACUUCUCAUGGUUC*GUUCGc -3' | 54 |
| NK-0025 | 25/26 | 5'- accaugagaaguaugacaacagccCCACACCGGCUGUUGUCAUACUUCUCAUGGU*UCUUCGg -3' | 55 |
| NK-0048 | 24/25 | 5'- accaugagaaguaugacaacagCCACACGGCUGUUGUCAUACUUCUCAUGGUU*CUUCGg -3' | 56 |
| NK-0049 | 23/24 | 5'- ccaugagaaguaugacaacagcCCACACCGCUGUUGUCAUACUUCUCAUGGU*UCUUCGa -3' | 57 |
| NK-0050 | 23/24 | 5'- accaugagaaguaugacaacagCCACACCCUGUUGUCAUACUUCUCAUGGUU*CUUCGg -3' | 58 |
| NK-0051 | 22/23 | 5'- ccaugagaaguaugacaacagCCACACCCUGUUGUCAUACUUCUCAUGGUU*UUCGa -3' | 59 |
| NK-0052 | 21/22 | 5'- caugagaaguaugacaacagCCACACCCUGUUGUCAUACUUCUCAUGGU*UUCGa -3' | 60 |
| NK-0053 | 21/22 | 5'- ccaugagaaguaugacaacaCCACACCUGUUGUCAUACUUCUCAUGGUU*UUCGa -3' | 61 |
| NK-0054 | 20/21 | 5'- caugagaaguaugacaacaCCACACCUGUUGUCAUACUUCUCAUGGU*UUCGa -3' | 62 |

SINGLE-STRANDED NUCLEIC ACID MOLECULE HAVING AMINO ACID BACKBONE

CROSS-REFERENCE TO RELATED APPLICATIONS

This patent application is the U.S. national phase of International Patent Application No. PCT/JP2012/084247, filed Dec. 29, 2012, which claims the benefit of Japanese Patent Application No. 2012-001711, filed on Jan. 7, 2012, and Japanese Patent Application No. 2012-026745, filed on Feb. 9, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 15,794 bytes ASCII (Text) file named "716960SequenceListing.txt," created Jun. 2, 2014.

TECHNICAL FIELD

The present invention relates to a single-stranded nucleic acid molecule that inhibits gene expression. More particularly, the present invention relates to a single-stranded nucleic acid molecule having an amino acid backbone, a composition containing same and use thereof.

BACKGROUND ART

As a technique for inhibiting gene expression, for example, RNA interference (RNAi) is known (Non-Patent Document 1). Inhibition of gene expression by RNA interference is generally carried out, for example, by administering a short double-stranded RNA molecule to a cell or the like. The aforementioned double-stranded RNA molecule is generally called siRNA (small interfering RNA). It has been reported that gene expression can also be inhibited by a circular RNA molecule having a double strand partially formed therein by intermolecular annealing (Patent Document 1).

DOCUMENT LIST

Non-Patent Document non-patent document 1: Fire et al., Nature, 1998 Feb. 19; 391(6669):806-11

Patent Document patent document 1: US-A-2004-058886

SUMMARY OF THE INVENTION

Problems to be Solved by the Invention

However, in the aforementioned each techniques, the RNA molecules to induce the inhibition of the gene expression have the following problems.

First, in order to produce the aforementioned siRNA, it is necessary to synthesize a sense strand and an antisense strand separately and to hybridize these strands at the end of the process. Thus, there is a problem of low manufacturing efficiency. Furthermore, when the aforementioned siRNA is administered to a cell, it is necessary to administer the siRNA to the cell while repressing the dissociation to single-stranded RNAs, which requires a laborious task of setting the conditions for handling the siRNA. The circular RNA molecule has a problem in that its synthesis is difficult.

These RNA molecules basically are composed of nucleotide residues. At present, in order to impart some function or label to the aforementioned RNA molecules, there is no other way but to modify, for example, any of the components, i.e., a base, a sugar residue, or a phosphate group, of the nucleotide residue(s). Therefore, in the development of pharmaceutical products and the like utilizing RNA interference, it is very difficult to alter the RNA molecules to impart a further function thereto or to label them while maintaining their function of inhibiting the gene expression.

Therefore, it is an object of the present invention to provide a novel nucleic acid molecule that can be produced easily and efficiently and can inhibit gene expression.

Means of Solving the Problems

To achieve the aforementioned object, the nucleic acid molecule of the present invention is a single-stranded nucleic acid molecule containing an expression inhibitory sequence that inhibits expression of a target gene, and containing region (X), linker region (Lx) and region (Xc), wherein the aforementioned linker region (Lx) is linked between the aforementioned region (X) and the aforementioned region (Xc), the aforementioned region (Xc) is complementary to the aforementioned region (X), at least one of the aforementioned region (X) and the aforementioned region (Xc) contains the aforementioned expression inhibitory sequence, and the aforementioned linker region (Lx) contains an atomic group derived from an amino acid.

The first composition of the present invention is a composition for inhibiting the expression of a target gene, and characteristically contains the above-mentioned single-stranded nucleic acid molecule of the present invention.

The second composition of the present invention is a pharmaceutical composition which characteristically contains the above-mentioned single-stranded nucleic acid molecule of the present invention.

The expression inhibiting method of the present invention is a method of inhibiting the expression of a target gene, which characteristically uses the above-mentioned single-stranded nucleic acid molecule of the present invention.

The expression induction method of the present invention is a method of inducing RNA interference that inhibits expression of the target gene, wherein the aforementioned single-stranded nucleic acid molecule of the present invention is used.

The method of treating a disease of the present invention includes a step of administering the above-mentioned single-stranded nucleic acid molecule of the present invention to a patient, wherein the above-mentioned single-stranded nucleic acid molecule has, as the above-mentioned expression inhibitory sequence, a sequence that inhibits expression of a gene causing the above-mentioned disease.

Effect of the Invention

The single-stranded nucleic acid molecule of the present invention can inhibit gene expression. Since it is not circular, synthesis thereof is easy. Since it is a single strand that does not require an annealing step for a double strand, it can be produced efficiently. Moreover, since the aforementioned linker region contains the aforementioned non-nucleotide residue, for example, conventional alteration of nucleotide residue is not the limited option but, for example, alteration such as modification of the aforementioned linker region and the like is also possible.

It is the inventors of the present invention who first discovered that the gene expression can be inhibited according to the structure of the single-stranded nucleic acid molecule of the present invention. It is speculated that the gene expression inhibitory effect of the single-stranded nucleic acid molecule of the present invention is caused by a phenomenon similar to RNA interference. It is to be noted, however, that the inhibition of the gene expression in the present invention is not limited or restricted by RNA interference.

BRIEF DESCRIPTION OF THE DRAWINGS

FIG. 1 shows schematic views illustrating an example of the single-stranded nucleic acid molecule of the present invention.

FIG. 2 shows schematic views illustrating another example of the single-stranded nucleic acid molecule of the present invention.

FIG. 3 shows schematic views illustrating other examples of the single-stranded nucleic acid molecule of the present invention.

FIG. 5 shows ssRNA used in a Reference Example. The numbers on the right indicate sequence identification numbers (i.e., SEQ ID NOs: 24-41). From the 5' side, a region indicated with underlined lower-case letters is the aforementioned region (Xc); a region indicated with underlined upper-case letters is the aforementioned inner region (Z); and a region indicated with underlined lower-case letters is the aforementioned region (Yc). A region between the aforementioned regions (Xc) and (Z) is a linker region (Lx), and a region between the regions (Z) and (Yc) is a linker region (Ly). Also, "Xc/Yc" indicates the ratio between the base length (Xc) of the aforementioned region (Xc) and the base length (Yc) of the aforementioned region (Yc). "*" indicates an unpaired base.

FIG. 9 is a graph showing the relative expression level of the LMNA gene in a Reference Example.

FIG. 10 shows ssRNA used in a Reference Example. The numbers on the right indicate sequence identification numbers (SEQ ID NO: 54-62). From the 5' side, a region indicated with underlined lower-case letters is the aforementioned region (Xc); a region indicated with underlined upper-case letters is the aforementioned inner region (Z); and a region indicated with underlined lower-case letters is the aforementioned region (Yc). Also, "Xc+Yc/X+Y" indicates the ratio between the base length of the aforementioned regions (Xc) and (Yc) and the total base length of the inner 5' side region (X) and the inner 3' side region (Y). "*" indicates an unpaired base.

DESCRIPTION OF EMBODIMENTS

Figure 4:
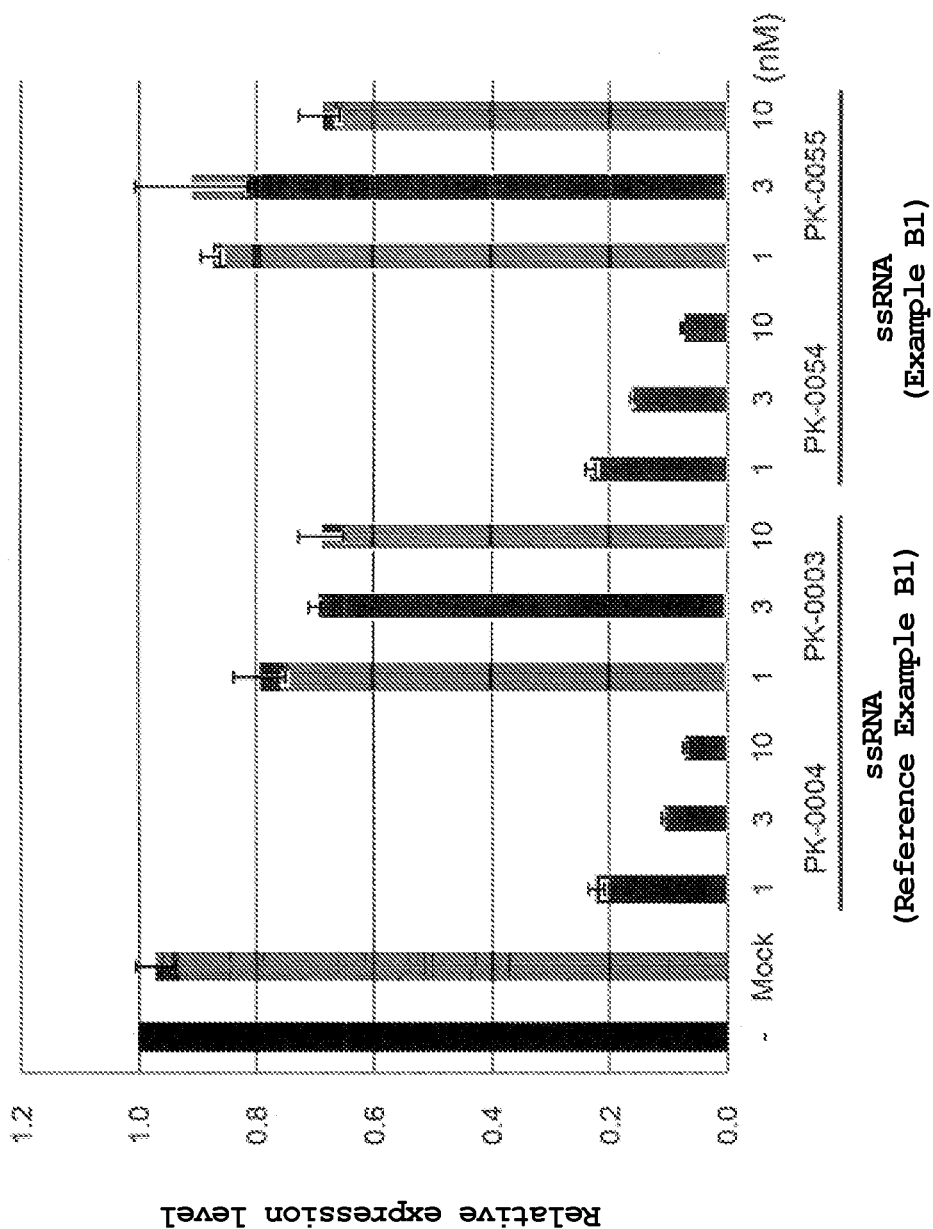
FIG. 4 is a graph showing the relative expression level of the GAPDH gene in the Example of the present invention.

Unless otherwise specified, the terms used in the present specification mean what is generally meant by them in the art.

1. ssPN Molecule

The single-stranded nucleic acid molecule of the present invention is, as described above, a single-stranded nucleic acid molecule containing an expression inhibitory sequence that inhibits expression of a target gene, and containing region (X), linker region (Lx) and region (Xc), wherein the aforementioned linker region (Lx) is linked between the aforementioned region (X) and the aforementioned region (Xc), the aforementioned region (Xc) is complementary to the aforementioned region (X), at least one of the aforementioned region (X) and the aforementioned region (Xc) contains the aforementioned expression inhibitory sequence, and the aforementioned linker region (Lx) contains an atomic group derived from an amino acid.

In the present invention, "inhibition of expression of a target gene" means, for example, inhibiting the expression of the aforementioned target gene. The mechanism by which the aforementioned inhibition is achieved is not particularly limited, and may be, for example, downregulation or silencing. The aforementioned inhibition of the expression of the target gene can be verified by, for example, a decrease in the amount of a transcription product derived from the target gene; a decrease in the activity of the aforementioned transcription product; a decrease in the amount of a translation product generated from the aforementioned target gene; a decrease in the activity of the aforementioned translation product; or the like. The aforementioned proteins may be, for example, mature proteins, precursor proteins before being subjected to processing or post-translational modification, or the like.

The single-stranded nucleic acid molecule of the present invention hereinafter also may be referred to as the "ssPN molecule" of the present invention. The ssPN molecule of the present invention can be used to inhibit, for example, the expression of a target gene in vivo or in vitro and can also be referred to as an "ssPN molecule for inhibiting the expression of a target gene" or "inhibitor of the expression of a target gene". Furthermore, the ssPN molecule of the present invention can inhibit the expression of the aforementioned target gene by, for example, RNA interference, and it can also be referred to as an "ssNP molecule for RNA interference", "ssPN molecule for inducing RNA interference", or "RNA interference agent or RNA interference-inducing agent". The present invention can also inhibit, for example, a side effect such as interferon induction.

In the ssPN molecule of the present invention, the 5' end and the 3' end are not linked to each other. Thus, the ssPN molecule of the present invention can also be referred to as a "linear single-stranded nucleic acid molecule".

In the ssPN molecule of the present invention, the aforementioned expression inhibitory sequence is a sequence that exhibits, for example, an activity of inhibiting the aforementioned expression of a target gene when the ssPN molecule of the present invention is introduced into a cell in vivo or in vitro. The aforementioned expression inhibitory sequence is not particularly limited, and can be set as appropriate depending on the kind of a target gene. As the aforementioned expression inhibitory sequence, for example, a sequence involved in RNA interference caused by siRNA can be used as appropriate. Generally, RNA interference is a phenomenon in which a long double-stranded RNA (dsRNA) is cleaved in a cell by Dicer to produce a double-stranded RNA (siRNA: small interfering RNA) composed of about 19 to 21 base pairs and having a protruding 3' end, and one of the single-stranded RNAs binds to a target mRNA to degrade the aforementioned mRNA, whereby the translation of the mRNA is inhibited. As the sequence of the single-stranded RNA of the aforementioned siRNA binding to the aforementioned target mRNA, for example, various kinds of sequences for various kinds of target genes have been reported. In the present invention, for example, the sequence of the single-stranded RNA of the aforementioned siRNA can be used as the aforementioned expression inhibitory sequence.

It should be noted that the point of the present invention is not the sequence information of the aforementioned expression inhibitory sequence for the aforementioned target gene, but, for example, the structure of a nucleic acid molecule that allows function of the aforementioned target gene expression inhibitory activity due to the aforementioned expression inhibitory sequence in a cell. Therefore, in the present invention, not only the sequences of the single-stranded RNA of the siRNA known at the time of the filing of the present application but also sequences that would be identified in the future can be used, for example, as the aforementioned expression inhibitory sequence.

The aforementioned expression inhibitory sequence is, for example, preferably at least 90% complementary, more preferably 95% complementary, still more preferably 98% complementary, and particularly preferably 100% complementary to a predetermined region of the aforementioned target gene. When such complementarity is satisfied, for example, an off-target effect can be reduced sufficiently.

As specific examples, when the target gene is a GAPDH gene, for example, a 19-base length sequence shown by SEQ ID NO: 5 can be used as the above-mentioned expression inhibitory sequence. When the target gene is TGF-β1, for example, a 21-base length sequence shown by SEQ ID NO: 15 can be used as the above-mentioned expression inhibitory sequence; when the target gene is a LAMA1 gene, for example, a 19-base length sequence shown by SEQ ID NO: 16 can be used as the above-mentioned expression inhibitory sequence; and when the target gene is a LMNA gene, for example, a 19-base length sequence shown by SEQ ID NO: 17 can be used.

```
                              (SEQ ID NO: 5)
5'-GUUGUCAUACUUCUCAUGG-3'

(SEQ ID NO: 15)
5'-AAAGUCAAUGUACAGCUGCUU-3'

(SEQ ID NO: 16)
5'-AUUGUAACGAGACAAACAC-3'

(SEQ ID NO: 17)
5'-UUGCGCUUUUUGGUGACGC-3'
```

It is speculated that the aforementioned inhibition of the expression of a target gene by the ssPN molecule of the present invention is achieved, for example, by RNA interference. It should be noted, however, that the present invention is by no means limited by this mechanism. Unlike the so-called siRNA, for example, the ssPN molecule of the present invention is not introduced to a cell or the like in the form of dsRNA composed of two single-stranded RNAs, and it is not always necessary to cleave out the aforementioned expression inhibitory sequence in the cell. Thus, it can be said, for example, that the ssPN molecule of the present invention exhibits an RNA interference-like function.

The ssPN molecule of the present invention can inhibit, for example, a side effect such as interferon induction in vivo and exhibits excellent nuclease resistance.

Each of the aforementioned linker regions may be composed of, for example, the non-nucleotide residue(s) having the aforementioned non-nucleotide structure only, or may contain the non-nucleotide residue(s) having the aforementioned non-nucleotide structure and the nucleotide residue(s).

In the aforementioned linker region, while the aforementioned "atomic group derived from an amino acid" is not particularly limited, it is, for example, an atomic group represented by the following formula (IA).

(IA)

In the aforementioned formula (IA), for example,
$X^1$ is $H_2$, O, S, or NH, and
atomic group A is optional but not containing a peptide bond.

In the ssPN molecule of the present invention, the aforementioned linker region is represented, for example, by the following formula (I):

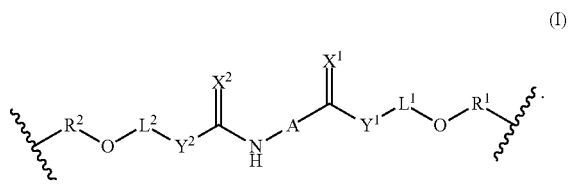

(I)

In the aforementioned formula (I), for example,
where:
$X^1$ and $X^2$ are each independently $H_2$, O, S, or NH;
$Y^1$ and $Y^2$ are each independently a single bond, $CH_2$, NH, O, or S;
$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or,
$L^1$ is a polyether chain obtained by substituting at least one carbon atom on the aforementioned alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

the aforementioned regions (Xc) and (X) are each linked to the aforementioned linker region (Lx) via —$OR^1$— or —$OR^2$—, wherein $R^1$ and $R^2$ may or may not be present, and when they are present, $R^1$ and $R^2$ are each independently a nucleotide residue or the aforementioned structure (I); and A is any atomic group, the following formula (Ia) is the aforementioned amino acid, and the following formula (Ia) is an amino acid other than peptide.

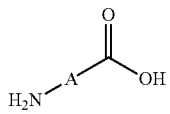

(Ia)

In the aforementioned formula (I), for example, $X^1$ and $X^2$ are each independently $H_2$, O, S, or NH. In the aforementioned formula (I), "$X^1$ is $H_2$" means that $X^1$ forms $CH_2$ (a methylene group) together with a carbon atom to which $X^1$ binds. The same applies to $X^2$.

In the aforementioned formula (I), $Y^1$ and $Y^2$ are each independently a single bond, $CH_2$, NH, O, or S.

In the aforementioned formula (I), $L^1$ is an alkylene chain having n carbon atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned formula (I), $L^2$ is an alkylene chain having m carbon atoms. A hydrogen atom(s) on the aforementioned alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned linker region (Lx). For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

For example, $R^a$, $R^b$, $R^c$ and $R^d$ are each independently a substituent or a protecting group, and may be the same or different. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like. These substituents are optionally substituted by one or more further substituents or further protecting groups. While the aforementioned further substituent is not particularly limited, for example, it may be a substituent exemplified above. The aforementioned further protecting group is not particularly limited and, for example, it may be a protecting group exemplified below. Hereinafter the same.

The aforementioned protecting group (or the aforementioned further protecting group) is a functional group that inactivates, for example, a highly-reactive functional group. Examples of the protecting group include known protecting groups. Regarding the aforementioned protecting group, for example, the description in the literature (J. F. W. McOmie, "Protecting Groups in Organic Chemistry", Plenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When $R^3$ is $OR^4$, the aforementioned protecting group is not particularly limited, and examples thereof include a TBDMS group, an ACE group, a TOM group, a CEE group, a CEM group, and a TEM group. Other examples of the protecting group include silyl-containing groups represented by the chemical formulae (P1) and (P2) to be shown later. The same applies hereinafter.

In the aforementioned formula (I), hydrogen atoms each independently may be substituted with, for example, a halogen such as Cl, Br, F, or I.

The aforementioned regions (Xc) and (X) are each linked, for example, to the aforementioned linker region (Lx) via —$OR^1$— or —$OR^2$—. $R^1$ and $R^2$ may or may not be present.

When $R^1$ and $R^2$ are present, $R^1$ and $R^2$ are each independently a nucleotide residue or the structure represented by the aforementioned formula (I). When $R^1$ and/or $R^2$ are/is the aforementioned nucleotide residue, the aforementioned linker region (Lx) is composed of, for example, the aforementioned non-nucleotide residue having the structure of the aforementioned formula (I) excluding the nucleotide residue $R^1$ and/or $R^2$, and the aforementioned nucleotide residue(s). When $R^1$ and/or $R^2$ are/is the structure represented by the aforementioned formula (I), the structure of the aforementioned linker region (Xc) is such that, for example, two or more of the aforementioned non-nucleotide residues having the structure of the aforementioned formula (I) are linked to each other. The number of the structures of the aforementioned formula (I) may be, for example, 1, 2, 3, or 4. When the linker region (Lx) includes a plurality of the aforementioned structures, the structures of the aforementioned (I) may be linked, for example, either directly or via the aforementioned nucleotide residue(s). On the other hand, when $R^1$ and $R^2$ are not present, the aforementioned linker region (Lx) is composed of, for example, the aforementioned non-nucleotide residue having the structure of the aforementioned formula (I) alone.

The combination of the aforementioned regions (Xc) and (X) with —$OR^1$— and —$OR^2$— is not particularly limited, and may be, for example, any of the following conditions.
Condition (1):
the aforementioned regions (Xc) and (X) are linked to the structure of the aforementioned formula (I) via —$OR^2$— and —$OR^1$—, respectively.
Condition (2):
the aforementioned regions (Xc) and (X) are linked to the structure of the aforementioned formula (I) via —$OR^1$— and —$OR^2$—, respectively.

In the ssPN molecule of the present invention, the atomic group A in the aforementioned formula (I) is not particularly limited and is optional; however, it is an amino acid represented by the following formula (Ia), which is not a peptide, as mentioned above.

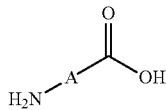

(Ia)

The atomic group A in the aforementioned formula (I), (IA) or (Ia) may or may not contain, for example, at least one selected from the group consisting of chain atomic group, alicyclic atomic group, and aromatic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. In the atomic group A in the aforementioned formula (I), (IA) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to any organic compound containing at least one amino group and at least one carboxy group in a molecule. The "peptide" refers to an organic compound having a structure wherein not less than 2 molecules of amino acid are bonded via a peptide bond. The aforementioned peptide bond may be an acid amide structure or an acid imide structure. When plural amino groups are present in the amino acid molecule represented by the aforementioned formula (Ia), the amino group clearly shown in the aforementioned formula (Ia) may be any amino group. In addition, when plural carboxy groups are present in the amino acid molecule represented by the aforementioned formula (Ia), the carboxy group clearly shown in the aforementioned formula (Ia) may be any carboxy group.

In the aforementioned linker region of the single-stranded nucleic acid of the present invention, the aforementioned amino acid may be, for example, natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a hetero ring. The aforementioned amino acid may be an amino acid constituting, for example, a protein. The aforementioned amino acid may be, for example, glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, tryptophan, β-alanine, 1-amino-2-carboxycyclopentane, or aminobenzoic acid, and may or may not further have a substituent or a protecting group. Examples of the aforementioned substituent include the substituents exemplified for the aforementioned $R^a$, $R^b$, $R^c$ and $R^d$. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned $R^a$, $R^b$, $R^c$ and $R^d$. When the amino acid of the aforementioned formula (Ia), which is not peptide, contains isomers such as optical isomer, geometric isomer, stereoisomer and the like, any isomer can be used.

In the ssPN molecule of the present invention, the aforementioned linker region (Lx) and the below-mentioned linker region (Ly) do not contain, for example, a non-nucleotide structure containing a pyrrolidine skeleton and a non-nucleotide structure containing a piperidine skeleton. Examples of the aforementioned pyrrolidine skeleton include the skeleton of a pyrrolidine derivative wherein one or more carbons constituting the 5-membered ring of pyrrolidine is/are substituted, and examples of the substituted carbon include carbon atoms other than C-2 carbon. The aforementioned carbon may be substituted by, for example, nitrogen, oxygen or sulfur. The aforementioned pyrrolidine skeleton may contain, for example, a carbon-carbon double bond or a carbon-nitrogen double bond in the 5-membered ring of pyrrolidine. In the aforementioned pyrrolidine skeleton, the carbon and nitrogen constituting the 5-membered ring of pyrrolidine may be bonded to, for example, hydrogen or the aforementioned substituent. The aforementioned linker region (Lx) can be bonded to, for example, the aforementioned region (X) and the aforementioned region (Xc) via any atom in the aforementioned pyrrolidine skeleton. The atom of the aforementioned pyrrolidine skeleton to be bonded to the aforementioned region (X) and the aforementioned region (Xc) is, for example, any one carbon atom or any one nitrogen of the aforementioned 5-membered ring. More specifically, for example, it is the 2-position carbon (C-2) or nitrogen of the aforementioned 5-membered ring. Examples of the aforementioned pyrrolidine skeleton include proline skeleton, prolinol skeleton and the like. As the aforementioned piperidine skeleton, for example, the skeleton of a piperidine derivative, wherein one or more carbons constituting the 6-membered ring of piperidine are substituted, can be mentioned. When the carbon is substituted, it is, for example, a carbon atom other than C-2 carbon. The aforementioned carbon may be, for example, substituted by nitrogen, oxygen or sulfur. The aforementioned piperidine skeleton may also contain, for example, in the 6-membered ring of piperidine, for example, a carbon-carbon double bond or a carbon-nitrogen double bond. In the aforementioned piperidine skeleton, the carbon and nitrogen constituting the 6-membered ring of piperidine may be bonded to, for example, a hydrogen group or the below-mentioned substituent. The aforementioned linker region (Lx) can also be bonded to, for example, the aforementioned region (X) and the aforementioned region (Xc) via any atom of the aforementioned piperidine skeleton. The atom of the aforementioned piperidine skeleton to be bonded to the aforementioned region (X) and the aforementioned region (Xc) is, for example, any one carbon atom or any one nitrogen of the aforementioned 6-membered ring, more specifically, for example, the 2-position carbon (C-2) and nitrogen of the aforementioned 6-membered ring.

As the aforementioned non-nucleotide structure containing a pyrrolidine skeleton or the aforementioned non-nucleotide structure containing a piperidine skeleton, for example, a structure represented by the following formula (Ib) can be mentioned. In the ssPN molecule of the present invention, the aforementioned linker region (Lx) and the below-mentioned linker region (Ly) do not contain, for example, a non-nucleotide structure containing a pyrrolidine skeleton and a non-nucleotide structure containing a piperidine skeleton.

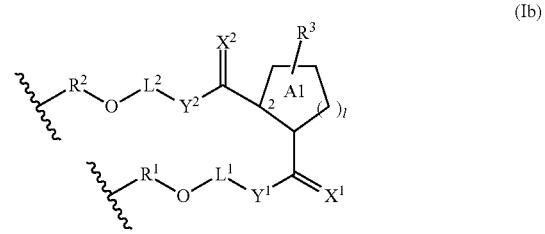

(Ib)

In the aforementioned formula (Ib), for example, $X^1$, $X^2$, $Y^1$, $Y^2$, $L^1$, $L^2$, $R^1$ and $R^2$ are as defined for the aforementioned formula (I).

$R^3$ is a hydrogen atom or substituent bonded to C-3, C-4, C-5 or C-6 on ring A. When $R^3$ is the aforementioned substituent, substituent $R^3$ may be one or more, or may be absent. When $R^3$ is present in plurality, they may be the same or different. The substituent $R^3$ is, for example, halogen, OH, $OR^4$, $NH_2$, $NHR^4$, $NR^4R^5$, SH, $SR^4$, oxo group (=O) and the like. $R^4$ and $R^5$ are, for example, each independently a substituent or a protecting group, and may be the same or different.

l is 1 or 2; when l=1, ring A is a 5-membered ring, for example, the aforementioned pyrrolidine skeleton. The aforementioned pyrrolidine skeleton is, for example, proline skeleton, prolinol skeleton or the like, and exemplified by the divalent structures thereof. When l=2, ring A is a 6-membered ring, for example, the aforementioned piperidine skeleton. In ring A, one carbon atom other than C-2 on ring A may be substituted by nitrogen, oxygen or sulfur. Ring A may contain, in ring A, a carbon-carbon double bond or a carbon-nitrogen double bond. Ring A is, for example, L type or D type. In ring A, one carbon atom other than the above-mentioned C-2 on ring A may be substituted by nitrogen, oxygen or sulfur, and may contain, in the above-mentioned ring A, a carbon-carbon double bond or a carbon-nitrogen double bond.

Examples of the structure of the aforementioned formula (I) include the structures of the following formulae (I-1) to (I-4). In the following formulae, n and m are the same as in the aforementioned formula (I).

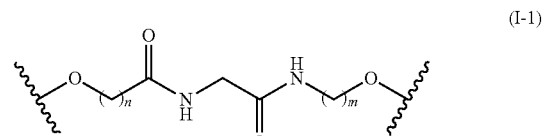

(I-1)

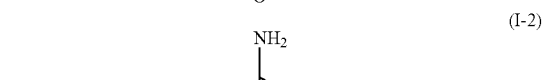

(I-2)

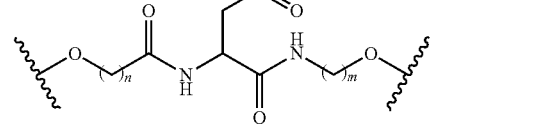

(I-3)

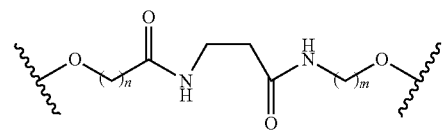

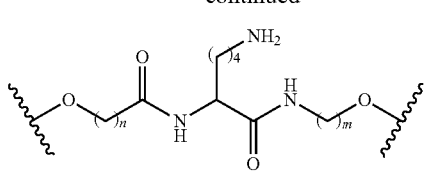
(I-4)

In the aforementioned formulae (I-1) to (I-4), n and m are not particularly limited, and are as described above. Specific example thereof is the aforementioned formula (I-1) wherein n=11 and m=12. The structure thereof is shown by the following formula (I-1a). Another specific example is the aforementioned formula (I-1) wherein n=5 and m=4. The structure thereof is shown by the following formula (I-1b). Still another specific example is the aforementioned formula (I-4) wherein n=5 and m=4. The structure thereof is shown by the following formula (I-4a).

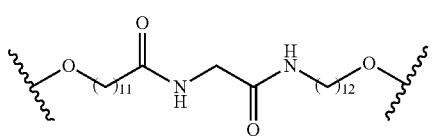
(I-1a)

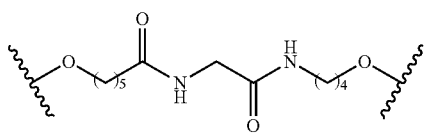
(I-1b)

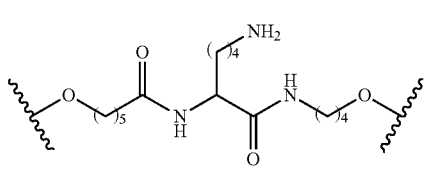
(I-4a)

In the ssPN molecule of the present invention, the aforementioned region (Xc) is complementary to the aforementioned region (X). Thus, in the ssPN molecule of the present invention, a double strand can be formed by fold-back of the aforementioned region (Xc) toward the region (X) and self-annealing of the aforementioned regions (Xc) and (X). The ssPN molecule of the present invention can form a double strand intramolecularly as described above. Thus, the structure of the ssPN molecule is totally different from, for example, the structure of a double-stranded RNA obtained through annealing of two separate single-stranded RNAs, such as siRNA conventionally used in RNA interference.

In the ssPN molecule of the present invention, for example, only the aforementioned region (Xc) may fold back to form a double strand with the aforementioned region (X), or another double strand may be formed in another region. Hereinafter, the former ssPN molecule, i.e., the ssPN molecule in which double strand formation occurs at one location is referred to as a "first ssPN molecule", and the latter ssPN molecule, i.e., the ssPN molecule in which double strand formation occurs at two locations is referred to as a "second ssPN molecule". Examples of the aforementioned first and second ssPN molecules are given below. It should be noted, however, that the present invention is not limited to these illustrative examples.

(1) First ssPN Molecule

The aforementioned first ssPN molecule is, for example, a molecule including the aforementioned region (X), the aforementioned region (Xc), and the aforementioned linker region (Lx).

The aforementioned first ssPN molecule may include the aforementioned region (Xc), the aforementioned linker region (Lx), and the aforementioned region (X) in this order from, for example, the 5' side to the 3' side, or may include the aforementioned region (Xc), the aforementioned linker region (Lx), and the aforementioned region (X) in this order from the 3' side to the 5' side.

In the aforementioned first ssPN molecule, the aforementioned region (Xc) is complementary to the aforementioned region (X). It is only necessary that the aforementioned region (Xc) has a sequence complementary to the entire region or part of the aforementioned region (X). Preferably, the aforementioned region (Xc) includes or is composed of a sequence complementary to the entire region or part of the region (X). The aforementioned region (Xc) may be, for example, perfectly complementary to the entire region or part of the aforementioned region (X), or one or a few bases in the region (Xc) may be noncomplementary to the same. Preferably, the region (Xc) is perfectly complementary to the same. The aforementioned expression "one or a few bases" means, for example, 1 to 3 bases, preferably 1 base or 2 bases.

In the aforementioned first ssPN molecule, the aforementioned expression inhibitory sequence is included in at least one of the aforementioned regions (Xc) and (X), as described above. The aforementioned first ssPN molecule may include, for example, one expression inhibitory sequence or two or more expression inhibitory sequences mentioned above.

In the latter case, the aforementioned first ssPN molecule may include, for example: two or more identical expression inhibitory sequences for the same target gene; two or more different expression inhibitory sequences for the same target gene; or two or more different expression inhibitory sequences for different target genes. When the aforementioned first ssPN molecule includes two or more expression inhibitory sequences mentioned above, the positions of the respective expression inhibitory sequences are not particularly limited, and they may be in one region or different regions selected from the aforementioned regions (X) and (Xc). When the aforementioned first ssPN molecule includes two or more expression inhibitory sequences mentioned above for different target genes, for example, the aforementioned first ssPN molecule can inhibit the expressions of two or more kinds of different target genes.

FIG. 1 shows schematic views illustrating an example of the aforementioned first ssPN molecule. FIG. 1A is a schematic view showing one example of the order of the respective regions in the aforementioned ssPN molecule. FIG. 1B is a schematic view showing the state where a double strand is formed in the aforementioned ssPN molecule. As shown in FIG. 1B, in the aforementioned ssPN molecule, a double strand is formed between the aforementioned regions (Xc) and (X), and the aforementioned Lx region has a loop structure depending on its length. The schematic views shown in FIG. 1 merely illustrate the order in which the aforementioned respective regions are linked to each other and the positional relationship of the respective regions forming the double strand, and they do not limit, for example, the lengths of the respective regions, the shape of the aforementioned linker region (Lx), and the like.

In the aforementioned first ssPN molecule, the number of bases in each of the aforementioned regions (Xc) and (X) is not particularly limited. Examples of the lengths of the respective regions are given below. However, it is to be noted that the present invention is by no means limited thereto. In the present invention, "the number of bases" means the "length", for example, and it can also be referred to as the "base length". In the present invention, for example, the numerical range regarding the number of bases discloses all the positive integers falling within that range. For example, the description "1 to 4 bases" disclosed all of "1, 2, 3, and 4 bases" (the same applies hereinafter).

The aforementioned region (Xc) may be, for example, perfectly complementary to the entire region of the aforementioned region (X). In this case, it means that, for example, the aforementioned region (Xc) is composed of a base sequence complementary to the entire region extending from the 5' end to the 3' end of the aforementioned region (X). In other words, it means that the aforementioned region (Xc) has the same base length as the aforementioned region (X), and all the bases in the aforementioned region (Xc) are complementary to all the bases in the aforementioned region (X).

Furthermore, the aforementioned region (Xc) may be, for example, perfectly complementary to part of the aforementioned region (X). In this case, it means that, for example, the aforementioned region (Xc) is composed of a base sequence complementary to the part of the aforementioned region (X). In other words, it means that the aforementioned region (Xc) is composed of a base sequence whose base length is shorter than the base length of the aforementioned region (X) by one or more bases, and all the bases in the aforementioned region (Xc) are complementary to all the bases in the part of the aforementioned region (X). The aforementioned part of the region (X) is preferably a region having a base sequence composed of, for example, successive bases starting from the base at the end (the 1st base) on the aforementioned region (Xc) side in the aforementioned region (X).

In the aforementioned first ssPN molecule, the relationship between the number of bases (X) in the aforementioned region (X) and the number of bases (Xc) in the aforementioned region (Xc) satisfy, for example, the following condition (3) or (5). For example, in the former case, specifically, the following condition (11) is satisfied:

$$X > Xc \quad (3)$$

$$X - Xc = 1 \text{ to } 10, \text{ preferably } 1, 2, \text{ or } 3, \text{ more preferably } 1 \text{ or } 2 \quad (11)$$

$$X = Xc \quad (5)$$

When the aforementioned region (X) and/or the aforementioned region (Xc) include(s) the aforementioned expression inhibitory sequence, the aforementioned region may be, for example, a region composed of the aforementioned expression inhibitory sequence only or a region including the aforementioned expression inhibitory sequence. The number of bases in the aforementioned expression inhibitory sequence is, for example, 19 to 30, preferably 19, 20, or 21. In the region(s) including the aforementioned expression inhibitory sequence, for example, the aforementioned expression inhibitory sequence further may have an additional sequence on its 5' side and/or 3' side. The number of bases in the aforementioned additional sequence is, for example, 1 to 31, preferably 1 to 21, and more preferably 1 to 11.

The number of bases in the aforementioned region (X) is not particularly limited. When the aforementioned region (X) includes the aforementioned expression inhibitory sequence, the lower limit of the number of bases in the aforementioned region (X) is, for example, 19, and the upper limit of the same is, for example, 50, preferably 30, and more preferably 25. Specifically, the number of bases in the aforementioned region (X) is, for example, 19 to 50, preferably 19 to 30, and more preferably 19 to 25.

The number of bases in the aforementioned region (Xc) is not particularly limited. The lower limit of the number of bases in the aforementioned region (Xc) is, for example, 19, preferably 20, and more preferably 21, and the upper limit of the same is, for example, 50, more preferably 40, and still more preferably 30.

In the aforementioned ssPN molecule, the length of the aforementioned linker region (Lx) is not particularly limited. The length of the aforementioned linker region (Lx) is preferably such that, for example, the aforementioned regions (X) and (Xc) can form a double strand. When the aforementioned linker region (Lx) includes the aforementioned nucleotide residue(s) in addition to the aforementioned non-nucleotide residue(s), the lower limit of the number of bases in the aforementioned linker region (Lx) is, for example, 1, preferably 2, and more preferably 3, and the upper limit of the same is, for example, 100, preferably 80, and more preferably 50.

The full length of the aforementioned first ssPN molecule is not particularly limited. In the aforementioned first ssPN molecule, the lower limit of the total number of bases (the number of bases in the full length ssPN molecule), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the aforementioned first ssPN molecule, the lower limit of the total number of bases excluding that in the aforementioned linker region (Lx) is, for example, 38, preferably 42, more preferably 50, still more preferably 51, and particularly preferably 52, and the upper limit of the same is, for example, 300, preferably 200, more preferably 150, still more preferably 100, and particularly preferably 80.

(2) Second ssPN Molecule

The aforementioned second ssPN molecule is a molecule that further includes a region (Y) and a region (Yc) that is complementary to the aforementioned region (Y), in addition to, for example, the aforementioned region (X), the aforementioned linker region (Lx), and the aforementioned region (Xc). In the aforementioned second ssPN molecule, an inner region (Z) is composed of the aforementioned region (X) and the aforementioned region (Y) that are linked to each other. The description regarding the aforementioned first ssPN molecule also applies to the aforementioned second ssPN molecule, unless otherwise stated.

The aforementioned second ssPN molecule may include, for example, the aforementioned region (Xc), the aforementioned linker region (Lx), the aforementioned region (X), the aforementioned region (Y), and the aforementioned region (Yc) in this order from the 5' side to the 3' side. In this case, the aforementioned region (Xc) also is referred to as a "5' side region (Xc)"; the aforementioned region (X) in the aforementioned inner region (Z) also is referred to as an "inner 5' side region (X)"; the aforementioned region (Y) in the aforementioned inner region (Z) also is referred to as an "inner 3' region (Y)"; and the aforementioned region (Yc) also is referred to as a "3' side region (Yc)". Alternatively, the aforementioned second ssPN molecule may include, for example, the aforementioned region (Xc), the aforementioned linker region (Lx), the aforementioned region (X), the aforementioned region (Y), and the aforementioned region (Yc) in this order from the 3' side to the 5' side. In this case, the aforementioned region (Xc) also is referred to as a "3' side region (Xc)"; the aforementioned region (X) in the aforementioned inner region (Z) also is referred to as an "inner 3' side region (X)"; the aforementioned region (Y) in the aforementioned inner region (Z) also is referred to as an "inner 5' region (Y)"; and the aforementioned region (Yc) also is referred to as a "5' side region (Yc)".

As described above, the aforementioned inner region (Z) is composed of, for example, the aforementioned regions (X) and (Y) that are linked to each other. For example, the aforementioned regions (X) and (Y) are linked directly to each other with no intervening sequence therebetween. The aforementioned inner region (Z) is defined as being "composed of the aforementioned regions (X) and (Y) that are linked to each other" merely to indicate the sequence context between the aforementioned regions (Xc) and (Yc). This definition does not intend to limit that, in the use of the aforementioned ssPN molecule, the aforementioned regions (X) and (Y) in the aforementioned inner region (Z) are discrete independent regions. That is, for example, when the aforementioned expression inhibitory sequence is included in the aforementioned inner region (Z), the aforementioned expression inhibitory sequence may be arranged to extend across the aforementioned regions (X) and (Y) in the aforementioned inner region (Z).

In the aforementioned second ssPN molecule, the aforementioned region (Xc) is complementary to the aforementioned region (X). It is only necessary that the aforementioned region (Xc) has a sequence complementary to the entire region or part of the aforementioned region (X). Preferably, the aforementioned region (Xc) includes or is composed of a sequence complementary to the entire region or part of the aforementioned region (X). The aforementioned region (Xc) may be, for example, perfectly complementary to the entire region or part of the aforementioned region (X), or one or a few bases in the aforementioned region (Xc) may be noncomplementary to the same. Preferably, the aforementioned region (Xc) is perfectly complementary to the same. The aforementioned expression "one or a few bases" means, for example, 1 to 3 bases, preferably 1 base or 2 bases.

In the aforementioned second ssPN molecule, the aforementioned region (Yc) is complementary to the aforementioned region (Y). It is only necessary that the aforementioned region (Yc) has a sequence complementary to the entire region or part of the aforementioned region (Y). Preferably, the aforementioned region (Yc) includes or is composed of a sequence complementary to the entire region or part of the aforementioned region (Y). The aforementioned region (Yc) may be, for example, perfectly complementary to the entire region or part of the aforementioned region (Y), or one or a few bases in the aforementioned region (Yc) may be noncomplementary to the same. Preferably, the aforementioned region (Yc) is perfectly complementary to the same. The aforementioned expression "one or a few bases" means, for example, 1 to 3 bases, preferably 1 base or 2 bases.

In the aforementioned second ssPN molecule, at least one of the aforementioned inner region (Z), which is composed of the aforementioned regions (X) and (Y), and the aforementioned region (Xc) includes, for example, the aforementioned expression inhibitory sequence. Furthermore, the aforementioned region (Yc) also may include the aforementioned expression inhibitory sequence. When the aforementioned inner region (Z) includes the aforementioned expression inhibitory sequence, for example, either of the aforementioned regions (X) and (Y) may include the aforementioned expression inhibitory sequence, or the aforementioned expression inhibitory sequence may be included to extend across the aforementioned regions (X) and (Y). The aforementioned second ssPN molecule may include, for example, one expression inhibitory sequence mentioned above, or two or more expression inhibitory sequences mentioned above.

When the aforementioned second ssPN molecule includes two or more expression inhibitory sequences mentioned above, the positions of the respective expression inhibitory sequences are not particularly limited. They may be in either one of the aforementioned inner region (Z) and the aforementioned region (Xc), or may be in one of the aforementioned inner region (Z) and the aforementioned region (Xc), and any region other than these regions.

In the aforementioned second ssPN molecule, for example, the aforementioned regions (Yc) and (Y) may be linked to each other either directly or indirectly. In the former case, for example, the aforementioned regions (Yc) and (Y) may be linked directly by phosphodiester linkage or the like. In the latter case, for example, the aforementioned second ssPN molecule may be configured so that it has a linker region (Ly) between the aforementioned regions (Yc) and (Y) and the aforementioned regions (Yc) and (Y) are linked via the aforementioned linker region (Ly).

When the aforementioned second ssPN molecule has the aforementioned linker region (Ly), for example, the aforementioned linker region (Ly) may be a linker composed of the aforementioned nucleotide residue(s), or a linker having a non-nucleotide structure containing at least one of a pyrrolidine skeleton and a piperidine skeleton such as described above. In the latter case, the aforementioned linker region (Ly) can be represented by the aforementioned formula (I), for example, and all the descriptions regarding the aforementioned formula (I) stated above in connection with the aforementioned linker region (Lx) also apply to the aforementioned linker region (Ly). When the aforementioned linker region (Lx) and the aforementioned linker region (Ly) are both represented by the aforementioned formula (I), A, $X^1$, $X^2$, $Y^1$, $Y^2$, $L^1$, $L^2$, $R^1$ and $R^2$ in the aforementioned linker region (Lx) and the aforementioned linker region (Ly) may be respectively the same or different.

The aforementioned regions (Yc) and (Y) are, for example, each linked to the aforementioned linker region (Ly) via —$OR^1$— or —$OR^2$—. In the aforementioned linker region (Ly), $R^1$ and $R^2$ may or may not be present, as in the above-described linker region (Lx).

The combination of the aforementioned regions (Xc) and (X) with aforementioned —$OR^1$— and —$OR^2$—, and the combination of the aforementioned regions (Yc) and (Y) with aforementioned —$OR^1$- and —$OR^2$— are not particularly limited, and may be, for example, any of the following conditions:

Condition (1):
the aforementioned regions (Xc) and (X) are linked to the structure of the aforementioned formula (I) via —$OR^2$— and —$OR^1$—, respectively; and
the aforementioned regions (Yc) and (Y) are linked to the structure of the aforementioned formula (I) via —$OR^1$— and —$OR^2$—, respectively.
Condition (2):
the aforementioned regions (Xc) and (X) are linked to the structure of the aforementioned formula (I) via —$OR^2$— and —$OR^1$—, respectively; and the aforementioned regions (Yc) and (Y) are linked to the structure of the aforementioned formula (I) via —OR²— and —OR¹—, respectively.

Condition (3):
the aforementioned regions (Xc) and (X) are linked to the structure of the aforementioned formula (I) via —OR¹— and —OR²—, respectively; and
the aforementioned regions (Yc) and (Y) are linked to the structure of the aforementioned formula (I) via —OR¹— and —OR²—, respectively.

Condition (4):
the aforementioned regions (Xc) and (X) are linked to the structure of the aforementioned formula (I) via —OR¹— and —OR²—, respectively; and
the aforementioned regions (Yc) and (Y) are linked to the structure of the aforementioned formula (I) via —OR²— and —OR¹—, respectively.

FIG. 2 shows schematic views illustrating an example of the aforementioned second ssPN molecule having the aforementioned linker region (Ly). FIG. 2A is a schematic view showing the order of the respective regions from the 5' side to the 3' side in the aforementioned ssPN molecule, as an illustrative example. FIG. 2B is a schematic view showing the state where double strands are formed in the aforementioned ssPN molecule. As shown in FIG. 2B, in the aforementioned ssPN molecule, double strands are formed between the aforementioned regions (Xc) and (X) and between the aforementioned regions (Y) and (Yc), and the aforementioned Lx region and the aforementioned Ly region each have a loop structure depending on their lengths. The schematic views shown in FIG. 2 merely illustrates the order in which the respective regions are linked and the positional relationship of the respective regions forming the double strand, and they do not limit, for example, the lengths of the respective regions, the shape of the linker region, and the like. Furthermore, although the aforementioned region (Xc) in on the 5' side in FIG. 2, the position of the aforementioned region (Xc) is not limited thereto, and the aforementioned region (Xc) may be on the 3' side.

In the aforementioned second ssPN molecule, the number of bases in each of the aforementioned regions (Xc), (X), (Y), and (Yc) is not particularly limited. Examples of the lengths of the respective regions are given below. It is to be noted, however, that the present invention is by no means limited thereto.

As described above, for example, the aforementioned region (Xc) may be complementary to the entire region of the aforementioned region (X). In this case, it is preferable that, for example, the aforementioned region (Xc) has the same base length as the aforementioned region (X), and is composed of a base sequence complementary to the entire region of the aforementioned region (X). It is more preferable that the aforementioned region (Xc) has the same base length as the aforementioned region (X) and all the bases in the aforementioned region (Xc) are complementary to all the bases in the aforementioned region (X), i.e., for example, the region (Xc) is perfectly complementary to the region (X). It is to be noted, however, that the configuration of the region (Xc) is not limited thereto, and one or a few bases in the region (Xc) may be noncomplementary to the corresponding bases in the region (X), for example, as described above.

Furthermore, as described above, the aforementioned region (Xc) may be complementary to, for example, a part of the aforementioned region (X). In this case, it is preferable that, for example, the aforementioned region (Xc) has the same base length as the part of the aforementioned region (X), i.e., the aforementioned region (Xc) is composed of a base sequence whose base length is shorter than the base length of the aforementioned region (X) by one or more bases. It is more preferable that the aforementioned region (Xc) has the same base length as the part of the aforementioned region (X) and all the bases in the aforementioned region (Xc) are complementary to all the bases in the part of the aforementioned region (X), i.e., for example, the region (Xc) is perfectly complementary to the part of the region (X). The part of the aforementioned region (X) is preferably a region having a base sequence composed of, for example, successive bases starting from the base at the end (the 1st base) on the aforementioned region (Xc) side in the aforementioned region (X).

As described above, the aforementioned region (Yc) may be complementary to, for example, the entire region of the aforementioned region (Y). In this case, it is preferable that, for example, the aforementioned region (Yc) has the same base length as the aforementioned region (Y), and is composed of a base sequence complementary to the entire region of the aforementioned region (Y). It is more preferable that the aforementioned region (Yc) has the same base length as the aforementioned region (Y) and all the bases in the aforementioned region (Yc) are complementary to all the bases in the aforementioned region (Y), i.e., for example, the region (Yc) is perfectly complementary to the region (Y). It is to be noted, however, that the configuration of the region (Yc) is not limited thereto, and one or a few bases in the region (Yc) may be noncomplementary to the corresponding bases in the region (Y), for example, as described above.

Furthermore, as described above, the aforementioned region (Yc) may be complementary to, for example, a part of the aforementioned region (Y). In this case, it is preferable that, for example, the aforementioned region (Yc) has the same base length as the part of the aforementioned region (Y), i.e., the aforementioned region (Yc) is composed of a base sequence whose base length is shorter than the base length of the aforementioned region (Y) by one or more bases. It is more preferable that the aforementioned region (Yc) has the same base length as the part of the aforementioned region (Y) and all the bases in the aforementioned region (Yc) are complementary to all the bases in the part of the aforementioned region (Y), i.e., for example, the region (Yc) is perfectly complementary to the part of the region (Y). The part of the aforementioned region (Y) is preferably a region having a base sequence composed of, for example, successive bases starting from the base at the end (the 1st base) on the aforementioned region (Yc) side in the aforementioned region (Y)

In aforementioned the second ssPN molecule, the relationship of the number of bases (Z) in the aforementioned inner region (Z) with the number of bases (X) in the aforementioned region (X) and the number of bases (Y) in the aforementioned region (Y) and the relationship of the number of bases (Z) in the aforementioned inner region (Z) with the number of bases (X) in the aforementioned region (X) and the number of bases (Xc) in the aforementioned region (Xc) satisfy, for example, the conditions of the following expressions (1) and (2).

$$Z=X+Y \quad (1)$$

$$Z>Xc+Yc \quad (2)$$

In the aforementioned second ssPN molecule, the relationship between the number of bases (X) in the aforementioned region (X) and the number of bases (Y) in the aforementioned region (Y) is not particularly limited, and satisfy, for example, any of the conditions of the following expressions:

$$X=Y \tag{19}$$

$$X<Y \tag{20}$$

$$X>Y \tag{21}.$$

In the second ssPN molecule, the relationship between the number of bases (X) in the aforementioned region (X) and the number of bases (Xc) in the aforementioned region (Xc), and the relationship between the number of bases (Y) in the aforementioned region (Y) and the number of bases (Yc) in the aforementioned region (Yc) satisfy, for example, any of the following conditions (a) to (d):

(a) Conditions of the following expressions (3) and (4) are satisfied.

$$X>Xc \tag{3}$$

$$Y=Yc \tag{4}$$

(b) Conditions of the following expressions (5) and (6) are satisfied.

$$X=Xc \tag{5}$$

$$Y>Yc \tag{6}$$

(c) Conditions of the following expressions (7) and (8) are satisfied.

$$X>Xc \tag{7}$$

$$Y>Yc \tag{8}$$

(d) Conditions of the following expressions (9) and (10) are satisfied.

$$X=Xc \tag{9}$$

$$Y=Yc \tag{10}$$

In the above-described conditions (a) to (d), for example, the difference between the number of bases (X) in the aforementioned region (X) and the number of bases (Xc) in the aforementioned region (Xc), and the difference between the number of bases (Y) in the aforementioned region (Y) and the number of bases (Yc) in the aforementioned region (Yc) preferably satisfy the following conditions.

(a) Conditions of the following expressions (11) and (12) are satisfied.

$$X-Xc=1 \text{ to } 10, \text{ preferably } 1, 2, 3, \text{ or } 4, \text{ more preferably } 1, 2, \text{ or } 3 \tag{11}$$

$$Y-Yc=0 \tag{12}$$

(b) Conditions of the following expressions (13) and (14) are satisfied.

$$X-Xc=0 \tag{13}$$

$$Y-Yc=1 \text{ to } 10, \text{ preferably } 1, 2, 3, \text{ or } 4, \text{ more preferably } 1, 2, \text{ or } 3 \tag{14}$$

(c) Conditions of the following expressions (15) and (16) are satisfied.

$$X-Xc=1 \text{ to } 10, \text{ preferably}, 1, 2, \text{ or } 3, \text{ more preferably } 1 \text{ or } 2 \tag{15}$$

$$Y-Yc=1 \text{ to } 10, \text{ preferably}, 1, 2, \text{ or } 3, \text{ more preferably } 1 \text{ or } 2 \tag{16}$$

(d) Conditions of the following expressions (17) and (18) are satisfied.

$$X-Xc=0 \tag{17}$$

$$Y-Yc=0 \tag{18}$$

Regarding the second ssPN molecules satisfying the aforementioned conditions (a) to (d), examples of their structures are shown respectively in the schematic views of FIG. 3. FIG. 3 shows the ssPN molecules including the aforementioned linker regions (Lx) and (Ly). FIG. 3A shows an example of the ssPN molecule satisfying the aforementioned condition (a); FIG. 3B shows an example of the ssPN molecule satisfying the aforementioned condition (b); FIG. 3C shows an example of the ssPN molecule satisfying the aforementioned condition (c); and FIG. 3D shows an example of the ssPN molecule satisfying the aforementioned condition (d). In FIG. 3, dotted lines indicate a state where double strands are formed by self-annealing. The ssPN molecules shown in FIG. 3 are all directed to examples where the relationship between the number of bases (X) in the aforementioned region (X) and the number of bases (Y) in the aforementioned region (Y) satisfy "X<Y" of the aforementioned expression (20). It is to be noted, however, that the relationship is not limited thereto, and "X=Y" of the aforementioned expression (19) or "X>Y" of the aforementioned expression (21) may be satisfied as described above. The schematic views shown in FIG. 3 merely illustrate the relationship between the aforementioned regions (X) and (Xc) and the relationship between the aforementioned regions (Y) and (Yc), and they do not limit, for example, the length and shape of each region, the presence or absence of the linker region (Ly), and the like.

The ssPN molecules of the above-mentioned (a) to (c) are configurations having a base not aligned with both the aforementioned regions (Xc) and (Yc) in the aforementioned inner region (Z) since, for example, the aforementioned regions (Xc) and (X), and regions (Yc) and (Y) each form a double strand. They may also be said configurations having a base not forming a double strand. In the aforementioned inner region (Z), the aforementioned base that is not aligned (also referred to as a base that does not form a double strand) is hereinafter to be referred to as an "unpaired base". In FIG. 3, the region of the aforementioned unpaired base is shown by "F". The number of the bases in the aforementioned region (F) is not particularly limited. The number of the bases (F) in the aforementioned region (F) is, for example, the number of the bases of "X−Xc" for the ssPN molecule of the aforementioned (a); the number of the bases of "Y−Yc" for the ssPN molecule of the above-mentioned (b); and the total of the number of the bases of "X−Xc" and the number of the bases of "Y−Yc" for the ssPN molecule of the aforementioned (c).

On the other hand, the ssPN molecule satisfying the aforementioned condition (d) is configured so that, for example, the entire region of the aforementioned inner region (Z) is aligned with the aforementioned regions (Xc) and (Yc), in other words, the entire region of the aforementioned inner region (Z) forms a double strand. In the ssPN molecule satisfying the aforementioned condition (d), the 5' end of the aforementioned region (Xc) and the 3' end of the aforementioned region (Yc) are not linked to each other.

The total number of the bases in the aforementioned region (Xc), the bases in the aforementioned region (Yc), and the aforementioned unpaired bases (F) in the aforementioned inner region (Z) is equal to the number of the bases in the aforementioned inner region (Z). Thus, the length of the aforementioned region (Xc) and the length of the aforementioned region (Yc) can be determined as appropriate depending on, for example, the length of the aforementioned inner region (Z), the number of the aforementioned unpaired bases, and the positions of the unpaired bases.

The number of the bases in the aforementioned inner region (Z) is, for example, 19 or more. The lower limit of the number of the bases is, for example, 19, preferably 20, and more preferably 21. The upper limit of the number of the aforementioned bases is, for example, 50, preferably 40, and more preferably 30. A specific example of the number of the bases in the aforementioned inner region (Z) is 19, 20, 21, 22, 23, 24, 25, 26, 27, 28, 29, or 30. When the aforementioned inner region (Z) includes the aforementioned expression inhibitory sequence, for example, such conditions are preferable.

When the aforementioned inner region (Z) includes the aforementioned expression inhibitory sequence, the aforementioned inner region (Z) may be, for example, a region composed of the aforementioned expression inhibitory sequence only or a region including the aforementioned expression inhibitory sequence. The number of bases of the aforementioned expression inhibitory sequence is, for example, 19 to 30, preferably 19, 20, or 21. When the aforementioned inner region (Z) includes the aforementioned expression inhibitory sequence, the aforementioned expression inhibitory sequence further may have an additional sequence on its 5' side and/or 3' side. The number of bases in the aforementioned additional sequence is, for example, 1 to 31, preferably 1 to 21, more preferably 1 to 11, and still more preferably 1 to 7.

The number of bases in the aforementioned region (Xc) is, for example, 1 to 29, preferably 1 to 11, more preferably 1 to 7, still more preferably 1 to 4, and particularly preferably 1, 2, or 3. When the aforementioned inner region (Z) or the aforementioned region (Yc) includes the aforementioned expression inhibitory sequence, for example, the number of bases as described above is preferable. A specific example is as follows: when the number of bases in the aforementioned inner region (Z) is 19 to 30 (e.g., 19), the number of bases in the aforementioned region (Xc) is, for example, 1 to 11, preferably 1 to 7, more preferably 1 to 4, and still more preferably 1, 2, or 3.

When the aforementioned region (Xc) includes the aforementioned expression inhibitory sequence, the aforementioned region (Xc) may be, for example, a region composed of the aforementioned expression inhibitory sequence only or a region including the aforementioned expression inhibitory sequence. For example, the length of the aforementioned expression inhibitory sequence is as described above. When the aforementioned region (Xc) includes the aforementioned expression inhibitory sequence, the aforementioned expression inhibitory sequence further may have an additional sequence on its 5' side and/or 3' side. The number of bases in the aforementioned additional sequence is, for example, 1 to 11, preferably 1 to 7.

The number of bases in the aforementioned region (Yc) is, for example, 1 to 29, preferably 1 to 11, more preferably 1 to 7, still more preferably 1 to 4, and particularly preferably 1, 2, or 3. When the aforementioned inner region (Z) or the aforementioned region (Xc) includes the aforementioned expression inhibitory sequence, for example, the number of bases as described above is preferable. A specific example is as follows: when the number of bases in the aforementioned inner region (Z) is 19 to 30 (e.g., 19), the number of bases in the aforementioned region (Yc) is, for example, 1 to 11, preferably 1 to 7, more preferably 1, 2, 3, or 4, and still more preferably 1, 2, or 3.

When the aforementioned region (Yc) includes the aforementioned expression inhibitory sequence, the aforementioned region (Yc) may be, for example, a region composed of the aforementioned expression inhibitory sequence only or a region including the aforementioned expression inhibitory sequence. The length of the aforementioned expression inhibitory sequence is, for example, as described above. When the aforementioned region (Yc) includes the aforementioned expression inhibitory sequence, the aforementioned expression inhibitory sequence further may have an additional sequence on its 5' side and/or 3' side. The number of bases in the aforementioned additional sequence is, for example, 1 to 11, preferably 1 to 7.

As described above, the relationship among the number of bases in the aforementioned inner region (Z), the number of bases in the aforementioned region (Xc), and the number of bases in the aforementioned region (Yc) can be expressed by, for example, the aforementioned expression (2): "Z $\geq$ Xc+Yc". Specifically, the number of bases represented by "Xc+Yc" is, for example, equal to the number of bases in the aforementioned inner region (Z), or lower than the number of bases in the aforementioned inner region (Z). In the latter case, "Z−(Xc+Yc)" is, for example, 1 to 10, preferably 1 to 4, and more preferably 1, 2, or 3. The aforementioned "Z−(Xc+Yc)" corresponds, for example, to the number of bases (F) in the unpaired base region (F) in the aforementioned inner region (Z).

In the aforementioned second ssPN molecule, the lengths of the aforementioned linker regions (Lx) and (Ly) are not particularly limited. The aforementioned linker region (Lx) is as described above. When the constitutional unit of the aforementioned linker region (Ly) include a base(s), the lower limit of the number of bases in the aforementioned linker region (Ly) is, for example, 1, preferably 2, and more preferably 3, and the upper limit of the same is, for example, 100, preferably 80, and more preferably 50. The number of bases in each of the aforementioned linker regions is specifically 1 to 50, 1 to 30, 1 to 20, 1 to 10, 1 to 7, or 1 to 4, for example, but it is not limited to these examples.

The aforementioned linker region (Ly) may be, for example, the same as or different from the aforementioned linker region (Lx).

The full length of the aforementioned second ssPN molecule is not particularly limited. In the aforementioned second ssPN molecule, the lower limit of the total number of bases (the number of bases in the full length ssPN molecule), is, for example, 38, preferably 42, more preferably 50, still more preferably 51, and particularly preferably 52, and the upper limit of the same is, for example, 300, preferably 200, more preferably 150, still more preferably 100, and particularly preferably 80. In the aforementioned second ssPN molecule, the lower limit of the total number of bases excluding those in the aforementioned linker regions (Lx) and (Ly) is, for example, 38, preferably 42, more preferably 50, still more preferably 51, and particularly preferably 52, and the upper limit of the same is, for example, 300, preferably 200, more preferably 150, still more preferably 100, and particularly preferably 80.

In the ssPN molecule of the present invention, it is only necessary that the aforementioned linker region (Lx) has the aforementioned non-nucleotide structure, as described above, and other constitutional units are not particularly limited. Examples of the aforementioned constitutional units include nucleotide residues. Examples of the aforementioned nucleotide residues include a ribonucleotide residue and a deoxyribonucleotide residue. The aforementioned nucleotide residue may be, for example, the one that is not modified (unmodified nucleotide residue) or the one that has been modified (modified nucleotide residue). By configuring the ssPN molecule of the present invention to include the aforementioned modified nucleotide residue, for example, the resistance of the ssPN molecule to nuclease can be improved, thereby allowing the stability of the ssPN molecule to be improved. Furthermore, the ssPN molecule of the present invention further may include, for example, a non-nucleotide residue in addition to the aforementioned nucleotide residue.

The aforementioned nucleotide residue is preferable as the constitutional unit of each of the aforementioned region (Xc), the aforementioned region (X), the aforementioned region (Y) and the aforementioned region (Yc). Each of the aforementioned regions is composed of, for example, any of the following residues (1) to (3):
(1) an unmodified nucleotide residue(s)
(2) a modified nucleotide residue(s)
(3) an unmodified nucleotide residue(s) and a modified nucleotide residue(s).

The aforementioned linker region (Lx) may be composed of, for example, the aforementioned non-nucleotide residue(s) only, or may be composed of the aforementioned non-nucleotide residue(s) and the aforementioned nucleotide residue(s). The aforementioned linker region (Lx) is composed of, for example, any of the following residues (4) to (7):
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s).

The constitutional units of the aforementioned linker region (Ly) are not particularly limited, and examples thereof include the aforementioned nucleotide residues and the aforementioned non-nucleotide residues, as described above. Each of the aforementioned linker regions may be composed of, for example, the aforementioned nucleotide residue(s) only, the aforementioned non-nucleotide residue(s) only, or both the aforementioned nucleotide residue(s) and the aforementioned non-nucleotide residue(s). Each of the aforementioned linker regions is composed of, for example, any of the following residues (1) to (7):
(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s).

Examples of the ssPN molecule, excluding the aforementioned linker region (Lx), of the present invention include molecules composed of the aforementioned nucleotide residues only; and molecules including the aforementioned non-nucleotide residue(s) in addition to the aforementioned nucleotide residues. In the ssPN molecule of the present invention, for example, the aforementioned nucleotide residues may be the aforementioned unmodified nucleotide residues only; the aforementioned modified nucleotide residues only; or both the aforementioned unmodified nucleotide residue(s) and the aforementioned modified nucleotide residue(s), as described above. When the aforementioned ssPN molecule includes both the aforementioned unmodified nucleotide residue(s) and the aforementioned modified nucleotide residue(s), the number of the aforementioned modified nucleotide residue(s) is not particularly limited, and is, for example, "one to several", specifically, for example, 1 to 5, preferably 1 to 4, more preferably 1 to 3, and most preferably 1 or 2. When the ssPN molecule of the present invention include the aforementioned non-nucleotide residue(s), the number of the aforementioned non-nucleotide residue(s) is not particularly limited, and is, for example, "one to several", specifically, for example, 1 or 2.

In the ssPN molecule of the present invention, for example, the aforementioned nucleotide residue is preferably a ribonucleotide residue. In this case, for example, the ssPN molecule of the present invention also is referred to as an "ssRNA molecule" or "P-ssRNA molecule". Examples of the aforementioned ssRNA molecule, excluding the aforementioned linker region (Lx), include molecules composed of the aforementioned ribonucleotide residues only; and a molecule including the aforementioned non-nucleotide residue(s) in addition to the aforementioned ribonucleotide residues. As described above, as the aforementioned ribonucleotide residues, for example, the aforementioned ssRNA molecule may include: the aforementioned unmodified ribonucleotide residues only; the aforementioned modified ribonucleotide residues only; or both the aforementioned unmodified ribonucleotide residue(s) and the aforementioned modified ribonucleotide residue(s).

When the aforementioned ssRNA molecule includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the aforementioned ssRNA molecule includes, for example, the aforementioned deoxyribonucleotid residue(s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

The ssPN molecule of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, and a Cy5 dye. Examples of the aforementioned dye include Alexa dyes such as Alexa 488. Examples of the aforementioned isotope include stable isotopes and radioisotopes. Among them, stable isotopes are preferable. For example, the aforementioned stable isotopes have a low risk of radiation exposure and they require no dedicated facilities. Thus, stable isotopes are excellent in handleability and can contribute to cost reduction. Moreover, for example, the aforementioned stable isotope does not change the physical properties of a compound labeled therewith and thus has an excellent property as a tracer. The aforementioned stable isotope is not particularly limited, and examples thereof include $^2$H, $^{13}$C, $^{15}$N, $^{17}$O, $^{18}$O, $^{33}$S, $^{34}$S, and, $^{36}$S.

In the ssPN molecule of the present invention, as described above, it is preferable to introduce, for example, the aforementioned labeling substance into the aforementioned non-nucleotide structure, preferably to the aforementioned non-nucleotide residue(s) in the aforementioned linker region (Lx). For example, introduction of the labeling substance to the aforementioned non-nucleotide residue(s) can be carried out easily and at low cost.

As described above, the ssPN molecule of the present invention can inhibit the aforementioned expression of a target gene. Thus, the ssPN molecule of the present invention can be used, for example, as a therapeutic agent for treating a disease caused by a gene. When the aforementioned ssPN molecule includes, as the aforementioned expression inhibitory sequence, a sequence that inhibits expression of a gene causing the aforementioned disease, for example, it is possible to treat the aforementioned disease by inhibiting the expression of the aforementioned target gene. In the present invention, the term "treatment" encompasses: prevention of the aforementioned diseases; improvement of the diseases; and improvement in prognosis, for example, and it can mean any of them.

The method of using the ssPN molecule of the present invention is not particularly limited. For example, the aforementioned ssPN molecule may be administered to a subject having the aforementioned target gene.

Examples of the aforementioned subject to which the ssPN molecule of the present invention is administered include cells, tissues, organs and the like. Examples of the aforementioned subject also include humans, nonhuman animals and the like such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

In the present invention, the aforementioned target gene whose expression is to be inhibited is not particularly limited, and any desired gene can be set to the target gene. The aforementioned expression inhibitory sequence may be designed as appropriate depending on the aforementioned gene.

Specific examples of the ssPN molecule of the present invention include, but are not limited to, the following. The base sequence of the aforementioned ssPN molecule when the aforementioned target gene is GAPDH gene is, for example, the base sequence shown by SEQ ID NO: 4 or 18, which may include one to several deletions, substitutions and/or additions, and when the aforementioned target gene is TGF-β1, the ssPN molecule is exemplified by the base sequences shown by SEQ ID NOs: 19-23, which may include one to several deletions, substitutions and/or additions. In the sequences of the following SEQ ID NOs: 4 and 18, the underlined part GUUGUCAUACUUCUCAUGG (SEQ ID NO: 5) is the region relating to the inhibition of the expression of GAPDH gene. In the following SEQ ID NOs: 19-23, "*" shows an unpaired base. In the following SEQ ID NOs: 4 and 18-23, the structures of Lx and Ly are not particularly limited and may be, for example, structure (Lg) shown in the below-mentioned Examples.

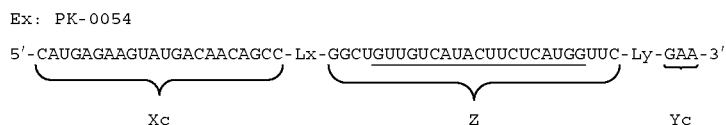

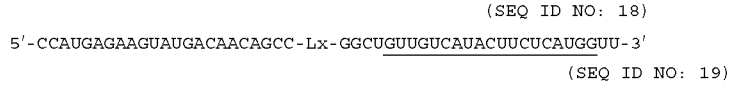

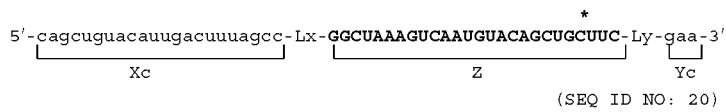

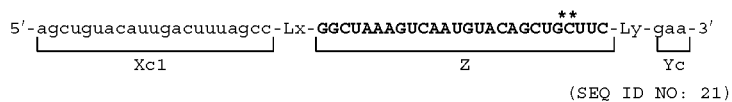

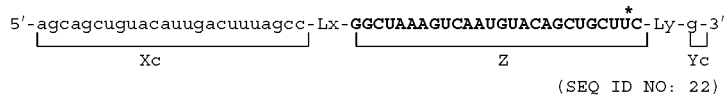

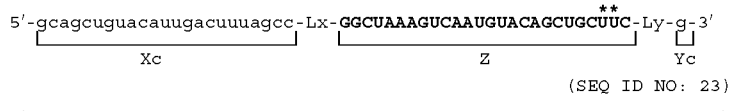

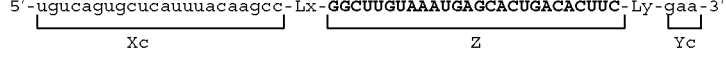

As to the use of the ssPN molecule of the present invention, the following description regarding the composition, the expression inhibitory method, the treatment method, and the like according to the present invention to be describe below can be referred to.

Since the ssPN molecule of the present invention can inhibit the expression of a target gene as described above, for example, it is useful as a pharmaceutical product, a diagnostic agent, an agricultural chemical, and a tool for conducting research on medical science, life science, and the like.

In the present invention, the term "alkyl" encompasses, for example, straight-chain and branched alkyl groups. The number of carbon atoms in the aforementioned alkyl is not particularly limited, and is, for example, 1 to 30, preferably 1 to 6 or 1 to 4. Examples of the aforementioned alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl. Among them, for example, methyl, ethyl, n-propyl, isopropyl, n-butyl, isobutyl, sec-butyl, tert-butyl, n-pentyl, isopentyl, neopentyl, n-hexyl, isohexyl, and the like are preferable.

In the present invention, the term "alkenyl" encompasses, for example, straight-chain and branched alkenyls. Examples of the aforementioned alkenyl include the aforementioned alkyls having one or more double bonds. The number of carbon atoms in the aforementioned alkenyl is not particularly limited, and is, for example, the same as that in the aforementioned alkyl, preferably 2 to 8. Examples of the aforementioned alkenyl include vinyl, 1-propenyl, 2-propenyl, 1-butenyl, 2-butenyl, 3-butenyl, 1,3-butadienyl, and 3-methyl-2-butenyl.

In the present invention, the term "alkynyl" encompasses, for example, straight-chain and branched alkynyls. Examples of the aforementioned alkynyl include the aforementioned alkyls having one or more triple bonds. The number of carbon atoms in the aforementioned alkynyl is not particularly limited, and is, for example, the same as that in the aforementioned alkyl, preferably 2 to 8. Examples of the aforementioned alkynyl include ethynyl, propynyl, and butynyl. The aforementioned alkynyl may further include, for example, one or more double bonds.

In the present invention, the term "aryl" encompasses, for example, monocyclic aromatic hydrocarbon groups and polycyclic aromatic hydrocarbon groups. Examples of the aforementioned monocyclic aromatic hydrocarbon group include phenyl. Examples of the aforementioned polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Among them, for example, phenyl, naphthyls such as 1-naphthyl and 2-naphthyl, and the like are preferable.

In the present invention, the term "heteroaryl" encompasses, for example, monocyclic aromatic heterocyclic groups and condensed aromatic heterocyclic groups. Examples of the aforementioned heteroaryl include furyls (e.g., 2-furyl, 3-furyl), thienyls (e.g., 2-thienyl, 3-thienyl), pyrrolyls (e.g., 1-pyrrolyl, 2-pyrrolyl, 3-pyrrolyl), imidazolyls (e.g., 1-imidazolyl, 2-imidazolyl, 4-imidazolyl), pyrazolyls (e.g., 1-pyrazolyl, 3-pyrazolyl, 4-pyrazolyl), triazolyls (e.g., 1,2,4-triazol-1-yl, 1,2,4-triazol-3-yl, 1,2,4-triazol-4-yl), tetrazolyls (e.g., 1-tetrazolyl, 2-tetrazolyl, 5-tetrazolyl), oxazolyls (e.g., 2-oxazolyl, 4-oxazolyl, 5-oxazolyl), isoxazolyls (e.g., 3-isoxazolyl, 4-isoxazolyl, 5-isoxazolyl), thiazolyls (e.g., 2-thiazolyl, 4-thiazolyl, 5-thiazolyl), thiadiazolyls, isothiazolyls (e.g., 3-isothiazolyl, 4-isothiazolyl, 5-isothiazolyl), pyridyls (e.g., 2-pyridyl, 3-pyridyl, 4-pyridyl), pyridazinyls (e.g., 3-pyridazinyl, 4-pyridazinyl), pyrimidinyls (e.g., 2-pyrimidinyl, 4-pyrimidinyl, 5-pyrimidinyl), furazanyls (e.g., 3-furazanyl), pyrazinyls (e.g., 2-pyrazinyl), oxadiazolyls (e.g., 1,3,4-oxadiazol-2-yl), benzofuryls (e.g., 2-benzo[b]furyl, -benzo[b]furyl, 4-benzo[b]furyl, 5-benzo[b]furyl, 6-benzo[b]furyl, 7-benzo[b]furyl), benzothienyls (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g., 1-benzimidazolyl, 2-benzimidazolyl, 4-benzimidazolyl, 5-benzimidazolyl), dibenzofuryls, benzoxazolyls, benzothiazolyls, quinoxalinyls (e.g., 2-quinoxalinyl, 5-quinoxalinyl, 6-quinoxalinyl), cinnolinyls (e.g., 3-cinnolinyl, 4-cinnolinyl, 5-cinnolinyl, 6-cinnolinyl, 7-cinnolinyl, 8-cinnolinyl), quinazolinyls (e.g., 2-quinazolinyl, 4-quinazolinyl, 5-quinazolinyl, 6-quinazolinyl, 7-quinazolinyl, 8-quinazolinyl), quinolyls (e.g., 2-quinolyl, 3-quinolyl, 4-quinolyl, 5-quinolyl, 6-quinolyl, 7-quinolyl, 8-quinolyl), phthalazinyls (e.g., 1-phthalazinyl, 5-phthalazinyl, 6-phthalazinyl), isoquinolyls (e.g., 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g., 2-pteridinyl, 4-pteridinyl, 6-pteridinyl, 7-pteridinyl), carbazolyls, phenanthridinyls, acridinyls (e.g., 1-acridinyl, 2-acridinyl, 3-acridinyl, 4-acridinyl, 9-acridinyl), indolyls (e.g., 1-indolyl, 2-indolyl, 3-indolyl, 4-indolyl, 5-indolyl, 6-indolyl, 7-indolyl), isoindolyls, phenazinyls (e.g., 1-phenazinyl, 2-phenazinyl), and phenothiazinyls (e.g., 1-phenothiazinyl, 2-phenothiazinyl, 3-phenothiazinyl, 4-phenothiazinyl).

In the present invention, for example, the term "cycloalkyl" refers to cyclic saturated hydrocarbon groups and the number of carbon atoms in the cycloalkyl is, for example, 3 to 15. Examples of the aforementioned cycloalkyl include cyclopropyl, cyclobutyl, cyclopentyl, cyclohexyl, cycloheptyl, cyclooctyl, bridged cyclic hydrocarbon groups, and spiro hydrocarbon groups. Among them, cyclopropyl, cyclobutyl, cyclopentyl, cyclohexyl, bridged cyclic hydrocarbon groups, and the like are preferable.

In the present invention, examples of the "bridged cyclic hydrocarbon groups" include bicyclo[2.1.0]pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, and 2-adamantyl.

In the present invention, examples of the "spiro hydrocarbon groups" include spiro[3.4]octyl.

In the present invention, the term "cycloalkenyl" encompasses, for example, unsaturated cyclic aliphatic hydrocarbon groups and the number of carbon atoms in the cycloalkenyl is, for example, 3 to 7. Examples of the aforementioned group include cyclopropenyl, cyclobutenyl, cyclopentenyl, cyclohexenyl, and cycloheptenyl. Among them, cyclopropenyl, cyclobutenyl, cyclopentenyl, cyclohexenyl, and the like are preferable. The aforementioned term "cycloalkenyl" also encompasses, for example, bridged cyclic hydrocarbon groups and spiro hydrocarbon groups having an unsaturated bond in their rings.

In the present invention, examples of the "arylalkyl" include benzyl, 2-phenethyl, and naphthalenylmethyl. Examples of the "cycloalkylalkyl" and "cyclylalkyl" include cyclohexylmethyl and adamantylmethyl. Examples of the "hydroxyalkyl" include hydroxymethyl and 2-hydroxyethyl.

In the present invention, the "alkoxy" encompasses, for example, groups composed of any of the aforementioned alkyls and oxygen (alkyl-O-groups) and examples thereof include methoxy, ethoxy, n-propoxy, isopropoxy, and n-butoxy. Examples of the "alkoxyalkyl" include methoxymethyl. Examples of the "aminoalkyl" include 2-aminoethyl.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolidinyl, 2-imidazolidinyl, 4-imidazolidinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, and tetrahy drofuranyl.

In the present invention, examples of the "heterocyclylalkyl" include piperidinylmethyl and piperazinylmethyl. Examples of the "heterocyclylalkenyl" include 2-piperidinylethenyl. Examples of the "heteroarylalkyl" include pyridylmethyl and quinolin-3-ylmethyl.

In the present invention, the term "silyl" encompasses groups represented by the formula $R_3Si—$, where R independently can be selected from the aforementioned alkyls, aryls, and cycloalkyls. Examples of the silyl include a trimethylsilyl group and a tert-butyldimethylsilyl group. Examples of the "silyloxy" include a trimethylsilyloxy group. Examples of the "silyloxyalkyl" include trimethylsilyloxymethyl.

In the present invention, examples of the "alkylene" include methylene, ethylene, and propylene.

In the present invention, the above-described various groups may be substituted. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like.

2. Nucleotide Residue

The aforementioned nucleotide residue includes, for example, a sugar, a base, and a phosphate as its components. The aforementioned nucleotide residue may be, for example, a ribonucleotide residue or a deoxyribonucleotide residue, as described above. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned nucleotide residue may be, for example, an unmodified nucleotide residue or a modified nucleotide residue. The aforementioned components of the aforementioned unmodified nucleotide residue are the same or substantially the same as, for example, the components of a naturally-occurring nucleotide residue. Preferably, the components are the same or substantially the same as the components of a nucleotide residue occurring naturally in a human body.

The aforementioned modified nucleotide residue is, for example, a nucleotide residue obtained by modifying the aforementioned unmodified nucleotide residue. For example, the aforementioned modified nucleotide residue may be such that any of the components of the aforementioned unmodified nucleotide residue is modified. In the present invention, "modification" means, for example, substitution, addition, and/or deletion of any of the aforementioned components; and substitution, addition, and/or deletion of an atom(s) and/or a functional group(s) in the aforementioned component(s). It can also be referred to as "alteration". Examples of the aforementioned modified nucleotide residue include naturally-occurring nucleotide residues and artificially-modified nucleotide residues. Regarding the aforementioned naturally-derived modified nucleotide residues, for example, Limbach et al. (Limbach et al., 1994, Summary: the modified nucleosides of RNA, Nucleic Acids Res. 22: pp. 2183 to 2196) can be referred to. The aforementioned modified nucleotide residue may be, for example, a residue of an alternative of the aforementioned nucleotide residue.

Examples of the modification of the aforementioned nucleotide residue include modification of a ribose-phosphate backbone (hereinafter referred to as a "ribophosphate backbone").

In the aforementioned ribophosphate backbone, for example, a ribose residue may be modified. In the aforementioned ribose residue, for example, the 2'-position carbon can be modified. Specifically, a hydroxyl group bound to, for example, the 2'-position carbon can be substituted with hydrogen or fluoro. By substituting the hydroxyl group bound to the aforementioned 2'-position carbon with hydrogen, it is possible to substitute the ribose residue with deoxyribose residue. The aforementioned ribose residue can be substituted with its stereoisomer, for example, and may be substituted with, for example, an arabinose residue.

The aforementioned ribophosphate backbone may be substituted with, for example, a non-ribophosphate backbone having a non-ribose residue and/or a non-phosphate. The aforementioned non-ribophosphate backbone may be, for example, the aforementioned ribophosphate backbone modified to be uncharged. Examples of an alternative obtained by substituting the ribophosphate backbone with the aforementioned non-ribophosphate backbone in the aforementioned nucleotide residue include morpholino, cyclobutyl, and pyrrolidine. Other examples of the aforementioned alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acids). Among them, PNA is preferable.

In the aforementioned ribophosphate backbone, for example, a phosphate group can be modified. In the aforementioned ribophosphate backbone, a phosphate group in the closest proximity to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking atoms asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is, for example, an alkyl group or an aryl group) and substitution with S is preferable. It is preferable that both the aforementioned non-linking oxygens are substituted, for example, and it is more preferable that both the non-linking oxygens are substituted with S. Examples of the aforementioned modified phosphate group include phosphorothioates, phosphorodithioates, phosphoroselenates, boranophosphates, boranophosphate esters, hydrogen phosphonates, phosphoroamidates, alkyl or aryl phosphonates, and phosphotriesters. In particular, phosphorodithioate in which both of the aforementioned two non-linking oxygens are substituted with S is preferable.

In the aforementioned phosphate group, for example, the aforementioned linking oxygen(s) may be substituted. The aforementioned oxygen(s) can be substituted with, for example, any atom selected from S (sulfur), C (carbon), and N (nitrogen). Examples of the aforementioned modified phosphate group include: bridged phosphoroamidates resulting from the substitution with N; bridged phosphorothioates resulting from the substitution S; and bridged methylenephosphonates resulting from the substitution C. Preferably, substitution of the aforementioned linking oxygen(s) is performed in, for example, at least one of the 5' end nucleotide residue and the 3' end nucleotide residue of the ssPN molecule of the present invention. When the substitution is performed on the 5' side, substitution with C is preferable. When the substitution is performed on the 3' side, substitution with N is preferable.

The aforementioned phosphate group may be substituted with, for example, the aforementioned phosphate-free linker. The aforementioned linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylenecarbonylamino group and a methylenemethylimino group.

In the ssPN molecule of the present invention, for example, at least one of a nucleotide residue at the 3' end and a nucleotide residue at the 5' end may be modified. For example, the nucleotide residue at either one of the 3' end and the 5' end may be modified, or the nucleotide residues at both the 3' end and the 5' end may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances as described above and protecting groups. Examples of the aforementioned protecting groups include S (sulfur), Si (silicon), B (boron), and ester-containing groups. The functional molecules such as the aforementioned labeling substances can be used, for example, in the detection and the like of the ssPN molecule of the present invention.

The aforementioned other molecule may be, for example, added to the phosphate group of the aforementioned nucleotide residue or may be added to the aforementioned phosphate group or the aforementioned sugar residue via a spacer. For example, the terminus atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminus atom of the aforementioned nucleotide alternative such as PNA.

The aforementioned spacer is not particularly limited, and examples thereof include —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxathiine), peptide complexes (e.g., Antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, Eu$^{3+}$ complexes of tetraazamacrocycles).

In the ssPN molecule of the present invention, for example, the aforementioned 5' end may be modified with a phosphate group or a phosphate group analog. Examples of the aforementioned phosphorylation include:

5'-monophosphate ((HO)$_2$(O)P—O-5');
5'-diphosphate ((HO)$_2$(O)P—O—P (HO) (O)—O-5');
5'-triphosphate ((HO)$_2$(O)P—O—(HO)(O)P—O—P(HO)(O)—O-5');
5'-guanosine cap (7-methylated or non-methylated, 7m-G-O-5'-(HO) (O)P—O—(HO)(O)P—O—P(HO)(O)—O-5');
5'-adenosine cap (Appp);
any modified or unmodified nucleotide cap structure (N—O-5'-(HO)(O)P—O—(HO)(O)P—O—P(HO)(O)—O-5');
5'-monothiophosphate (phosphorothioate: (HO)$_2$(S)P—O-5');
5'-monodithiophosphate (phosphorodithioate: (HO) (HS)(S) P—O-5');
5'-phosphorothiolate ((HO)$_2$ (O) P—S-5');

sulfur substituted monophosphate, diphosphate, and triphosphates (e.g., 5'-α-thiotriphosphate, 5'-γ-thiotriphosphate, and the like);

5'-phosphoramidates ((HO)$_2$ (O) P—NH-5', (HO)(NH$_2$)(O) P—O-5');

5'-alkylphosphonates (e.g., RP(OH)(O)—O-5', (OH)$_2$(O)P-5'-CH$_2$, where R is alkyl (e.g., methyl, ethyl, isopropyl, propyl, or the like)); and 5'-alkyletherphosphonates (e.g., RP(OH)(O)—O-5', where R is alkylether (e.g., methoxymethyl, ethoxymethyl, or the like)).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

Examples of the aforementioned base include: purine bases such as adenine and guanine; and pyrimidine bases such as cytosine, uracil, and thymine. Other examples of the aforementioned base include inosine, thymine, xanthine, hypoxanthine, nubularine, isoguanisine, and tubercidine. Examples of the aforementioned base also include: 2-aminoadenine, alkyl derivatives such as 6-methylated purine; alkyl derivatives such as 2-propylated purine; 5-halouracil and 5-halocytosine; 5-propynyluracil and 5-propynylcytosine; 6-azouracil, 6-azocytosine, and 6-azothymine; 5-uracil (pseudouracil), 4-thiouracil, 5-halouracil, 5-(2-aminopropyl)uracil, 5-aminoallyluracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N$^4$-acetylcytosine; 2-thiocytosine; N6-methyladenine; N6-isopentyladenine; 2-methylthio-N6-isopentenyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the aforementioned modified nucleotide residue include those having no base, i.e., those having an abasic ribophosphate backbone. Furthermore, as the aforementioned modified nucleotide residue, for example, those described in U.S. Provisional Application No. 60/465,665 (filing date: Apr. 25, 2003) and International Application No. PCT/US04/07070 (filing date: Mar. 8, 2004) can be used and these documents are incorporated herein by reference.

3. Synthesis Method of ssPN Molecule of the Present Invention

The method for synthesizing the ssPN molecule of the present invention is not particularly limited, and a conventionally known method can be employed. Examples of the aforementioned synthesis method include synthesis methods according to genetic engineering procedures and chemical synthesis methods. Examples of the genetic engineering procedures include: synthesis methods utilizing in vitro transcription; methods using a vector; methods carried out using a PCR cassette and the like. The aforementioned vector is not particularly limited, and examples thereof include non-virus vectors such as plasmid, and virus vectors, which is not limited thereto. The aforementioned chemical synthesis methods are not particularly limited, and examples thereof include a phosphoramidite method and an H-phosphonate method. The aforementioned chemical synthesis methods can be carried out, for example, using a commercially available automated nucleic acid synthesizer. In the aforementioned chemical synthesis methods, an amidite is generally used. The aforementioned amidite is not particularly limited. Examples of commercially available amidites include RNA Phosphoramidites (2'-O-TEDMSi, trade name, Samchully Pharm. Co., Ltd.), ACE amidite, TOM amidite, CEE amidite, CEM amidite, and TEM amidite. In the synthesis of the ssPN molecule of the present invention, it is preferable to use, for example, the monomer of the present invention to be described below for the synthesis of the linker region(s) represented by the aforementioned formula (I).

4. Composition

The expression inhibitory composition according to the present invention is, as described above, a composition for inhibiting the expression of a target gene, containing the aforementioned ssPN molecule of the present invention. The composition of the present invention is characterized in that it contains the aforementioned ssPN molecule of the present invention, and other configurations are by no means limited. The expression inhibitory composition of the present invention can also be referred to, for example, as an expression inhibitory reagent.

According to the present invention, for example, by administering to a subject in which the aforementioned target gene is present, it is possible to inhibit the expression of the aforementioned target gene.

Furthermore, as described above, the pharmaceutical composition according to the present invention contains the aforementioned ssPN molecule of the present invention. The composition of the present invention is characterized in that it contains the aforementioned ssPN molecule of the present invention, and other configurations are by no means limited. The pharmaceutical composition of the present invention can also be referred to, for example, as a pharmaceutical product.

According to the present invention, for example, administration to a patient with a disease caused by a gene can inhibit the expression of the aforementioned gene, thereby treating the aforementioned disease. In the present invention, the term "treatment" encompasses, as mentioned above, prevention of the aforementioned diseases; improvement of the diseases; and improvement in prognosis, for example, and it can mean any of them.

In the present invention, a disease to be treated is not particularly limited, and examples thereof include diseases caused by the expression of genes. Depending on the kind of the aforementioned disease, a gene that causes the disease may be set as the aforementioned target gene, and further, depending on the aforementioned target gene, the aforementioned expression inhibitory sequence may be set as appropriate.

A specific example is as follows. By setting the aforementioned TGF-β1 gene as the aforementioned target gene and incorporating an expression inhibitory sequence for the aforementioned gene into the aforementioned ssPN molecule, the ssPN molecule can be used for the treatment of, for example, inflammatory diseases, specifically, acute lung injury and the like.

The method of using the expression inhibitory composition and the pharmaceutical composition according to the present invention (hereinafter, both the compositions simply are referred to as "the compositions") are not particularly limited, and examples thereof include administering the aforementioned ssPN molecule to a subject having the aforementioned target gene.

Examples of the aforementioned subject to which the ssPN molecule of the present invention is administered include cells, tissues, organs and the like. Examples of the aforementioned subject also include humans, nonhuman animals and the like such as nonhuman mammals, i.e., mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, and COS cells; stem cells such as ES cells and hematopoietic stem cells; and cells isolated from living organisms, such as primary cultured cells.

The aforementioned administration method is not particularly limited, and can be determined, for example, as appropriate depending on the subject. When the aforementioned subject is a cultured cell, the administration method may be, for example, a method using a transfection reagent, an electroporation method, or the like. When the aforementioned administration is performed in vivo, the administration may be, for example, either oral administration or parenteral administration. Examples of the aforementioned parenteral administration include injection, subcutaneous administration, and local administration.

For example, each of the compositions of the present invention may contain only the ssPN molecule of the present invention or further may contain an additive(s) in addition to the ssPN molecule. The aforementioned additive is not particularly limited, and is preferably, for example, a pharmaceutically acceptable additive. The kind of the aforementioned additive is not particularly limited, and can be selected as appropriate depending on, for example, the kind of the subject.

In the composition of the present invention, for example, the aforementioned ssPN molecule may form a complex with the aforementioned additive. The aforementioned additive can also be referred to, for example, as a complexing agent. The aforementioned complex allows, for example, the aforementioned ssPN molecule to be delivered efficiently. The bond between the aforementioned ssPN molecule and the aforementioned complexing agent is not particularly limited, and examples thereof include noncovalent bond and the like. The aforementioned complex may be, for example, an inclusion complex and the like.

The aforementioned complexing agent is not particularly limited, and examples thereof include polymers, cyclodextrins, and adamantine. Examples of the aforementioned cyclodextrins include linear cyclodextrin copolymers and linear oxidized cyclodextrin copolymers.

Other examples of the aforementioned additive include a carrier, a binding substance that binds to a target cell, a condensing agent, and a fusogenic agent.

For example, the aforementioned carrier is preferably a polymer, more preferably a biopolymer. Preferably, the aforementioned carrier is, for example, biodegradable. Examples of the aforementioned carrier include: proteins such as human serum albumin (HSA), low-density lipoprotein (LDL), and globulin; carbohydrates such as, for example, dextran, pullulan, chitin, chitosan, inulin, cyclodextrin, and hyaluronic acid; and lipids. As the aforementioned carrier, for example, a synthetic polymer such as a synthetic polyamino acid can also be used. Examples of the aforementioned polyamino acid include polylysine (PLL), poly-L-aspartic acid, poly-L-glutamic acid, styrene-maleic anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymer, and polyphosphazine.

Examples of the aforementioned binding substance include thyroid-stimulating hormone, melanocyte-stimulating hormone, lectin, glycoproteins, surfactant protein A, mucin carbohydrate, multivalent lactose, multivalent galactose, N-acetyl-galactosamine, N-acetyl-gulucosamine, multivalent mannose, multivalent fucose, glycosylated polyamino acid, multivalent galactose, transferrin, bisphosphonate, polyglutamic acid, polyaspartic acid, lipids, cholesterol, steroids, bile acid, folate, vitamin B12, biotin, Neproxin, RGD peptide, and RDG peptide mimetic.

Examples of the aforementioned fusogenic agent and condensing agent include polyamino chains such as polyethyleneimine (PEI). For example, PEI may be either linear or branched, and also may be either synthetic or naturally occurring. The aforementioned PEI may be, for example, substituted with an alkyl or a lipid. As the aforementioned fusogenic agent, it is also possible to use, for example, polyhistidine, polyimidazole, polypyridine, polypropyleneimine, mellitin, a polyacetal substance (e.g., cationic polyacetal or the like), or the like. The aforementioned fusogenic agent may have, for example, an $\alpha$-helix structure. The aforementioned fusogenic agent may be, for example, a membrane disruptive agent such as mellitin.

As to the compositions according to the present invention, for example, the descriptions regarding the formation of the aforementioned complex and the like in U.S. Pat. No. 6,509,323, U.S. Patent Publication No. 2003/0008818, PCT/US04/07070, and the like are incorporated herein by reference.

Other examples of the aforementioned additive include amphiphilic molecules and the like. The aforementioned amphiphilic molecule is, for example, a molecule having a hydrophobic region and a hydrophilic region. The aforementioned molecule is, for example, preferably a polymer. The aforementioned polymer may have, for example, a secondary structure, preferably a repeating secondary structure. Specifically, for example, polypeptide is preferable, and a-helix polypeptide and the like are more preferable.

The aforementioned amphiphilic polymer may be, for example, a polymer having two or more amphiphilic subunits. Examples of the aforementioned subunit include subunits with a cyclic structure having at least one hydrophilic group and one hydrophobic group, and the like. The aforementioned subunit may contain, for example, steroid such as cholic acid, an aromatic structure, and the like. The aforementioned polymer may contain, for example, both a cyclic structure subunit, such as an aromatic subunit, and an amino acid.

5. Expression Inhibitory Method

The expression inhibitory method according to the present invention is, as described above, a method for inhibiting the expression of a target gene, in which the aforementioned ssPN molecule of the present invention is used. The expression inhibitory method of the present invention is characterized in that the aforementioned ssPN molecule of the present invention is used therein, and other steps and conditions are by no means limited.

In the expression inhibitory method of the present invention, the mechanism by which the aforementioned gene expression is inhibited is not particularly limited, and examples thereof include inhibition of the expression by RNA interference, and the like. The expression inhibitory method of the present invention is, for example, a method for inducing RNA interference that inhibits the aforementioned expression of a target gene, and it can also be referred to a method for inducing the expression that is characterized in that the aforementioned ssPN molecule of the present invention is used therein.

The expression inhibitory method of the present invention includes, for example, the step of administering the aforementioned ssPN molecule to a subject in which the aforementioned target gene is present. By the aforementioned administration step, for example, the aforementioned ssPN molecule is bought into contact with the aforementioned subject to which the ssPN molecule is administered. Examples of the aforementioned subject to which the ssPN molecule of the present invention is administered include cells, tissues, organs and the like. Examples of the aforementioned subject also include humans, nonhuman animals and the like such as nonhuman mammals, i.e., mammals excluding humans. The aforementioned administration may be performed, for example, in vivo or in vitro.

In the expression inhibitory method of the present invention, for example, the aforementioned ssPN molecule may be administered alone, or the aforementioned composition of the present invention containing the aforementioned ssPN molecule may be administered. The aforementioned administration method is not particularly limited and, for example, can be selected as appropriate depending on the kind of the subject.

6. Treatment Method

As described above, the method for treating a disease according to the present invention includes the step of administering the aforementioned ssPN molecule of the present invention to a patient, and the aforementioned ssPN molecule includes, as the aforementioned expression inhibitory sequence, a sequence that inhibits expression of a gene causing the aforementioned disease. The treatment method of the present invention is characterized in that the aforementioned ssPN molecule of the present invention is used therein, and other steps and conditions are by no means limited. The description regarding the aforementioned expression inhibitory method of the present invention also applies to, for example, the treatment method of the present invention.

7. Use of ssPN Molecule

The use according to the present invention is the use of the aforementioned ssPN molecule of the present invention for the aforementioned inhibition of the expression of a target gene. Also, the use according to the present invention is the use of the aforementioned ssPN molecule of the present invention for inducing RNA interference.

The nucleic acid molecule according to the present invention is a nucleic acid molecule for use in treatment of a disease. The aforementioned nucleic acid molecule is the aforementioned ssPN molecule of the present invention, and the aforementioned ssPN molecule includes, as the aforementioned expression inhibitory sequence, a sequence that inhibits expression of a gene causing the aforementioned disease.

8. Monomer

The monomer according to the present invention is a monomer for nucleic acid synthesis, having the structure of the following formula (II). The description regarding the aforementioned ssPN molecule of the present invention also applies to the monomer of the present invention, unless otherwise stated.

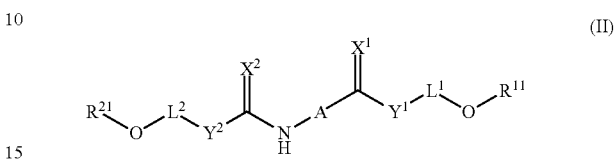

(II)

By use of the monomer of the present invention, for example, in the synthesis of the aforementioned ssPN molecule of the present invention, the linker regions (Lx) and (Ly) represented by the aforementioned formula (I) can be synthesized easily. The monomer of the present invention can be used an amidite for automated nucleic acid synthesis, for example, and is applicable to, for example, general automated nucleic acid synthesizers. Examples of the aforementioned synthesis method include a phosphoramidite method and an H-phosphonate method.

In the aforementioned formula, $X^1$ and $X^2$ are each independently $H_2$, O, S, or NH;

$Y^1$ and $Y^2$ are each independently a single bond, $CH_2$, NH, O, or S;

$R^{11}$ and $R^{21}$ are each independently H, a protecting group or a phosphate-protecting group;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to $OR^{11}$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^{21}$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

A is any atomic group, the following formula (Ia) is an amino acid which is not a peptide.

(Ia)

As to the portions in common between the aforementioned formula (II) and the aforementioned formula (I), the descriptions stated above regarding the aforementioned formula (I) also apply to the aforementioned formula (II). Specifically, in the aforementioned formula (II), as to $X^1$, $X^2$, $Y^1$, $Y^2$, $L^1$, $L^2$, m, n, and the ring A, for example, all the descriptions about them stated above regarding the aforementioned formula (I) apply.

In the aforementioned formula (II), $R^{11}$ and $R^{21}$ are each independently H, a protecting group, or a phosphate-protecting group, as described above.

The aforementioned protecting group is, for example, as described above regarding the aforementioned formula (I). Specifically, for example, the protecting group can be selected from Group I. The aforementioned Group I includes, for example, a dimethoxytrityl (DMTr) group, a TBDMS group, an ACE group, a TOM group, a CEE group, a CEM group, a TEM group, and silyl-containing groups represented by the following formulae (P1) or (P2). In particular, it is preferable that the protecting group is the DMtr group or any of the aforementioned silyl-containing groups.

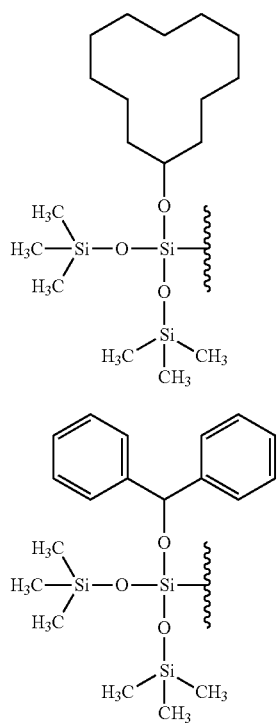

(P1)

(P2)

The aforementioned phosphate-protecting group can be represented, for example, by the following formula:

—P(OR$^6$)(NR$^7$R$^8$)

In the aforementioned formula, $R^6$ is a hydrogen atom or any substituent. For example, the substituent $R^6$ is preferably a hydrocarbon group, and the aforementioned hydrocarbon group may or may not be substituted with an electron-withdrawing group. Examples of the substituent $R^6$ include halogens, haloalkyls, heteroaryls, hydroxyalkyls, alkoxyalkyls, aminoalkyls, silyls, silyloxyalkyls, heterocyclylalkenyls, heterocyclylalkyls, heteroarylalkyls, and hydrocarbons such as alkyls, alkenyls, alkynyls, aryls, arylalkyls, cycloalkyls, cycloalkenyls, cycloalkylalkyls, and cyclylalkyls, which may or may not be substituted with an electron-withdrawing group. Specific examples of the substituent $R^6$ include a β-cyanoethyl group, a nitrophenylethyl group, and a methyl group.

$R^7$ and $R^8$ are each a hydrogen atom or any substituent, and they may be the same or different. The substituents $R^7$ and $R^8$ are preferably, for example, hydrocarbon groups, and the aforementioned hydrocarbon group may or may not be further substituted with any substituent. Examples of the aforementioned hydrocarbon group are the same as those listed in the above description regarding $R^6$, and the hydrocarbon group is preferably a methyl group, an ethyl group, or an isopropyl group. In this case, specific examples of —NR$^7$R$^8$ include a diisopropylamino group, a diethylamino group, and an ethylmethylamino group. Alternatively, the substituents $R^7$ and $R^8$ are joined to optionally form, together with the nitrogen atom(s) bonded thereto (i.e., —NR$^7$R$^8$ as a whole), a nitrogen-containing ring (e.g., a piperidyl group, a morpholino group, or the like).

Specifically, the aforementioned phosphate-protecting group can be selected from, for example, Group II described below. Group II includes, for example, —P(OCH$_2$CH$_2$CN)(N(i-Pr)$_2$) and —P(OCH$_3$)(N(i-Pr)$_2$). In the aforementioned formulae, i-Pr indicates isopropyl.

In the aforementioned formula (II), for example, one of $R^1$ and $R^2$ is H or a protecting group, and the other is H or a phosphate-protecting group. For example, it is preferable that, when $R^1$ is the aforementioned protecting group, $R^2$ is H or the aforementioned phosphate-protecting group. Specifically, it is preferable that, when $R^1$ is selected from the aforementioned Group I, $R^2$ is H or is selected from the aforementioned Group II. Also, it is preferable that, for example, when $R^1$ is the aforementioned phosphate-protecting group, $R^2$ is H or the aforementioned protecting group. Specifically, it is preferable that, when $R^1$ is selected from the aforementioned Group II, $R^2$ is H or is selected from the aforementioned Group I.

Examples of the structure of the aforementioned formula (II) include the following formulae (II-1) to (II-4). In the following formulae, n and m are the same as in the aforementioned formula (II).

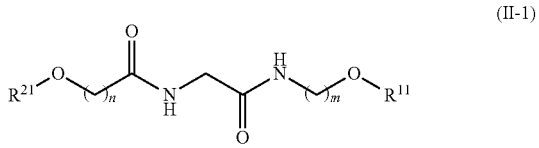

(II-1)

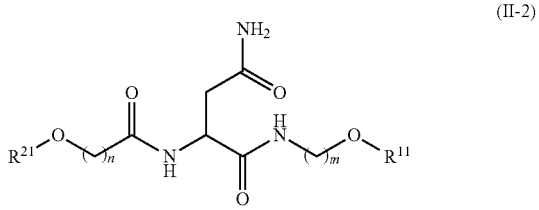

(II-2)

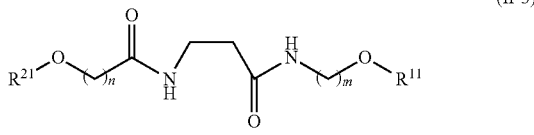

(II-3)

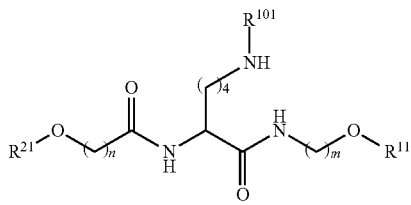

In the aforementioned formula (II-4), $R^{101}$ is, independently from $R^{11}$ and $R^{21}$, H, a protecting group or a phosphate-protecting group. The aforementioned protecting group and the aforementioned phosphate-protecting group for $R^{101}$ are not particularly limited and may be the same as, for example, $R^{11}$ and $R^{21}$, a perfluoroalkanoyl group such as Tfa (trifluoroacetyl group) and the like, Fmoc (9-fluorenylmethyloxycarbonyl group) and the like.

In the aforementioned formulas (II-1)-(II-4), n and m are not particularly limited and are as described above. Specific example thereof is the aforementioned formula (II-1) wherein n=11 and m=12, and the structure thereof is shown by the following formula (II-1a). Another specific example is the aforementioned formula (II-1) wherein n=5 and m=4, and the structure thereof is shown by the following formula (II-1b). Still another specific example is the aforementioned formula (II-4) wherein n=5 and m=4, and the structure thereof is shown by the following formula (II-4a).

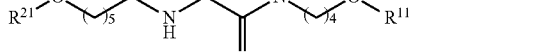

While the production method of a monomer in the present invention is not particularly limited, for example, as shown in the following scheme 1, the following compound (Ic) may be produced from compound (Ib), wherein the amino group of the aforementioned amino acid (Ia) is protected by a protecting group $R^{31}$, by a condensation reaction, (IIa) is produced from (Ic), and (IIa) is converted to (II). The following scheme 1 is an example and the present invention is not limited thereto. In the following chemical formulae (Ib) and (Ic), the protecting group $R^{31}$ is, for example, Fmoc (9-fluorenylmethyloxycarbonyl group), Z (benzyloxycarbonyl), BOC (t-butoxycarbonyl) and the like. In the following chemical formulae (Ib), (Ic) and (IIa), $Y^1$, $Y^2$, $L^1$, $L^2$, $R^{11}$ and $R^{21}$ are as defined for the aforementioned formula (II). The following compound (IIa) is a compound of the aforementioned formula (II) wherein $X^1$ is O and $X^2$ is O. Carbonyl oxygen in the following formula (II) may be appropriately converted to $X^1$ and $X^2$ in the aforementioned formula (II). When conversion is not necessary, the following compound (IIa) may be directly used as compound (II).

scheme 1

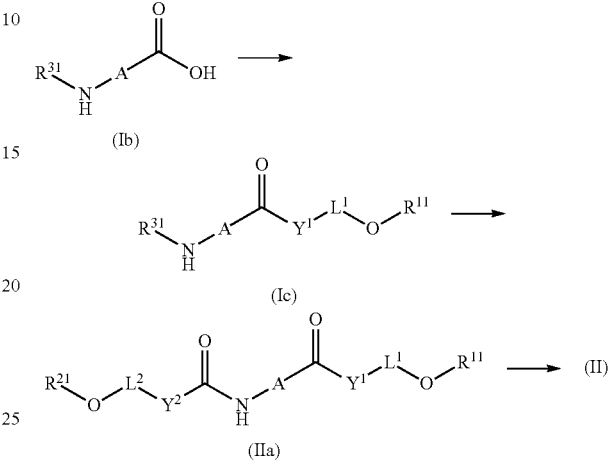

The monomer and the production method thereof in the present invention are further specifically exemplified by the following scheme 2. However, the following scheme 2 is an example, and the present invention is not limited thereto. In the following scheme 2, "Fmoc" is a 9-fluorenylmethyloxycarbonyl group, "iPr" is an isopropyl group, "Tr" is a trityl group or triphenylmethyl group, and "ODMTr" is a 4,4'-dimethoxytrityloxy group. Hereinafter the same.

scheme 2

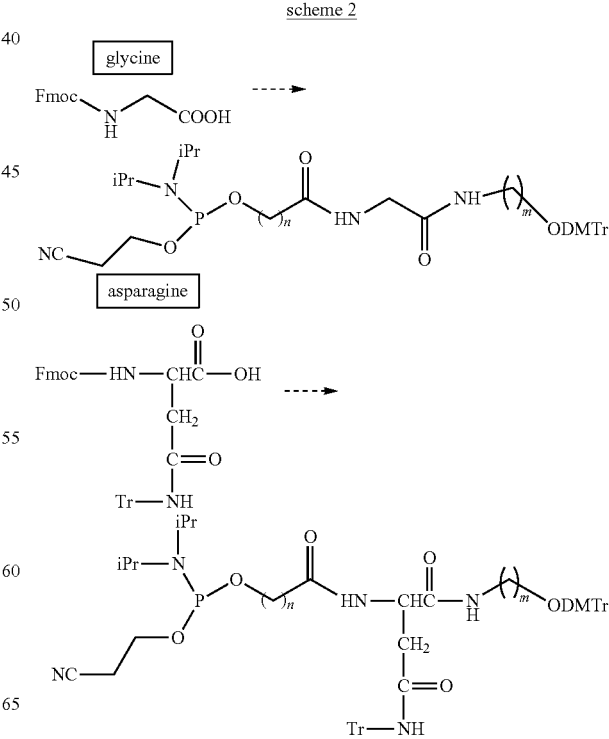

-continued

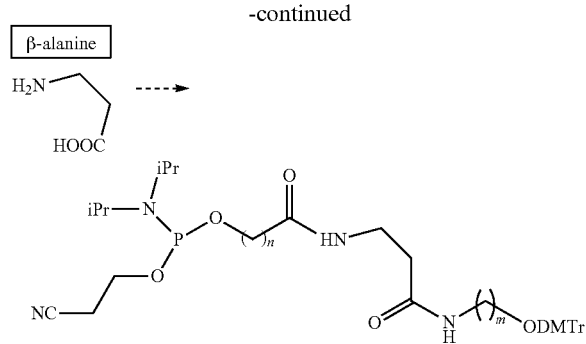

The monomer of the present invention preferably includes, for example, the aforementioned labeling substance. It is particularly preferable that the monomer of the present invention includes the aforementioned stable isotope. The aforementioned labeling substance is as described above.

When the monomer of the present invention includes an isotope such as the aforementioned stable isotope, the aforementioned isotope can be easily introduced into the aforementioned ssPN molecule of the present invention. The aforementioned monomer including an isotope can be synthesized from, for example, a raw material of amino acid (Ia) into which the aforementioned isotope is introduced. In the present invention, a method of obtaining the amino acid (Ia) into which an isotope is introduced is not particularly limited. For example, it may be produced by an appropriate method, or a commercially available product may be used.

As an amino acid into which a stable isotope is introduced, for example, an amino acid into which a heavy hydrogen (D) is introduced can be produced by treating amino acid (Ia) with $LiAlD_4$, as shown in the following scheme 3, and further oxidizing the resulting OH group.

scheme 3

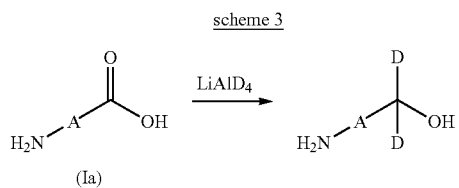

As an amino acid into which other stable isotope is introduced, for example, an amino acid into which a heavy oxygen ($^{18}O$) is introduced can be produced by reacting methyl ester of amino acid (Ia) with $H_2{}^{18}O$ under a basic condition, as shown in the following formula.

scheme 4

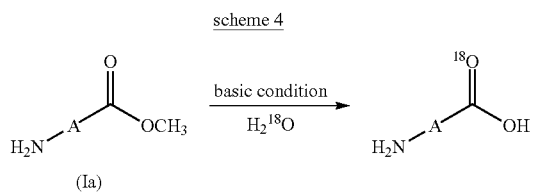

In addition, the production method of amino acid (Ia) including introduction of heavy nitrogen ($^{15}N$) or heavy carbon ($^{13}C$) and the like is not particularly limited, and it can be produced by an appropriate method.

A monomer having a stable isotope introduced thereto can be synthesized in the above-described manner. By using the aforementioned monomer as amidite for synthesis, a nucleic acid molecule in which a stable isotope is introduced to the aforementioned linker region can be synthesized.

In the following, the present invention will be described in detail with reference to examples and the like. It is to be noted, however, the present invention is by no means limited thereto.

EXAMPLES

Example A1

According to the following scheme 5, dodecanamidoglycine-4,4'-dimethoxytrityloxydodecanamido phosphoramidite (6) was synthesized. Compound (6) is one embodiment of the aforementioned monomer of the present invention. "Gly" in the following scheme 5 is a structure represented by the following formula, that is, an atomic group having a structure wherein one hydrogen atom of the amino group and OH of the carboxy group were removed from glycine. In the following, unless otherwise specified, "Gly" shows a structure of the following formula. In the following scheme 5, the NH side of Gly binds to Fmoc or carbonyl carbon, and the carbonyl carbon (CO) side of Gly binds to OH or N atom.

(Gly)

HN—$CH_2$—CO—

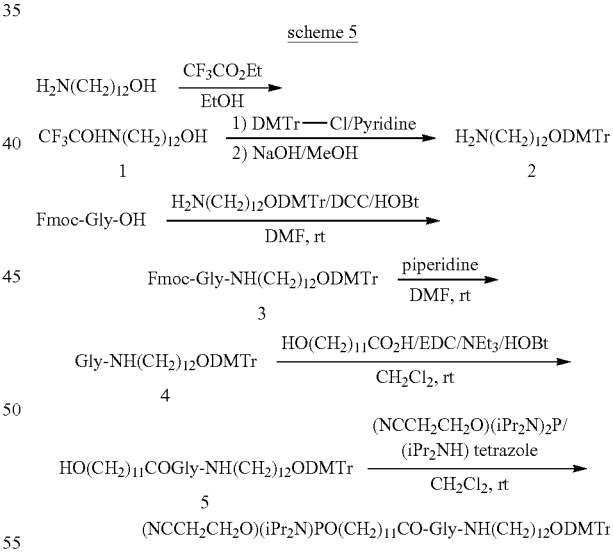

(1) 12-trifluoroacetamidododecanol (compound 1)

A solution (100 mL) of 12-aminododecanol (4.81 g, 23.9 mmol) and ethyl trifluoroacetate (6.79 g, 47.8 mmol) in ethanol was stirred at room temperature overnight. The reaction mixture was concentrated under reduced pressure to give 12-trifluoroacetamidododecanol (1) (6.98 g, q.) as a colorless syrup.

(2) 12-(4,4'-dimethoxytrityloxy)dodecanamine (compound 2)

Compound 1 (3.00 g, 10.08 mmol) was azeotropically dried three times with anhydrous pyridine. 4,4'-Dimethoxytrityl chloride (4.32 g, 12.1 mmol) and anhydrous pyridine (50 mL) were added to the residue by azeotropy, and the mixture was stirred at room temperature overnight. Methanol (10 mL) was added to the obtained reaction mixture and the mixture was stirred at room temperature for 30 min, and the solvent was evaporated to about 30 mL under reduced pressure at room temperature. Thereafter, dichloromethane (200 mL) was added, and the mixture was washed three times with saturated aqueous sodium bicarbonate, and further washed with saturated brine. After drying over sodium sulfate, the solvent was evaporated under reduced pressure. To a solution (100 mL) of the thus-obtained unpurified residue in methanol was added sodium hydroxide (2.02 g, 50.40 mmol) and the mixture was stirred at room temperature overnight. The reaction mixture was concentrated to about 30 mL under reduced pressure, water (100 mL) and dichloromethane (200 mL) were added, and the organic layer was separated. The separated organic layer was washed with saturated brine and dried over sodium sulfate. Thereafter, the desiccant (sodium sulfate) was separated by filtration and the solvent was evaporated under reduced pressure. The resultant residue was subjected to silica gel column chromatography (eluent: dichloromethane-methanol (95:5)+0.05% pyridine) to give 12-(4,4'-dimethoxytrityloxy)dodecanamine (2) (5.19 g, q.). The instrumental analytical values of 12-(4,4'-dimethoxytrityloxy)dodecanamine (2) are shown below.

12-(4,4'-dimethoxytrityloxy)dodecanamine (2);
$^1$H-NMR (CDCl$_3$): δ=7.45-7.43 (2H, m), 7.34-7.25 (6H, m), 7.21-7.20 (1H, m), 6.83-6.79 (4H, m), 3.78 (6H, s), 3.04-3.01 (2H, t, J=6.3 Hz), 2.70-2.67 (2H, t, J=6.8 Hz), 1.61-1.54 (6H, m), 1.33-1.24 (14H, m).

(3) Fmoc-glycine-4,4'-dimethoxytrityloxydodecanamide (compound 3)

To a solution (70 mL) of Fmoc-glycine (Fmoc-Gly-OH, purchased from Wako Pure Chemical Industries, Ltd.) (2.00 g, 6.73 mmol), dicyclohexylcarbodiimide (1.66 g, 8.07 mmol) and 1-hydroxybenzotriazole monohydrate (2.31 g, 16.14 mmol) in anhydrous N,N-dimethylformamide was added a solution (30 mL) of compound 2 (4.07 g, 8.07 mmol) in anhydrous N,N-dimethylformamide at room temperature under an argon atmosphere, and the mixture was stirred at room temperature overnight under an argon atmosphere. The resultant precipitate was separated by filtration, and the filtrate was concentrated under reduced pressure at 35° C. Dichloromethane (200 mL) was added to the obtained residue, and the mixture was washed three times with saturated aqueous sodium bicarbonate. The organic layer was fractionated and dried over sodium sulfate, and the solvent was evaporated under reduced pressure. The obtained residue was subjected to silica gel column chromatography (eluent: dichloromethane-methanol (95:5)+0.05% pyridine) to give Fmoc-glycylglycine-4,4'-dimethoxytrityloxybutyldodecanamide (3) (5.88 g, q.) as a colorless syrup.

(4) glycine-4,4'-dimethoxytrityloxydodecanamide (compound 4)

To compound 3 (5.88 g, 6.73 mmol) were added N,N-dimethylformamide (10 mL) and piperidine (4.8 mL) at room temperature, and the mixture was stirred at room temperature overnight. The solvent in the reaction mixture was evaporated under reduced pressure, and the obtained residue was subjected to silica gel column chromatography (eluent: dichloromethane-methanol (9:1)+0.05% pyridine) to give glycine-4,4'-dimethoxytrityloxydodecanamide (4) (3.44 g, 91%). The instrumental analytical values of glycine-4,4'-dimethoxytrityloxydodecanamide (4) are shown below.

glycine-4,4'-dimethoxytrityloxydodecanamide (4);
$^1$H-NMR (CDCl$_3$): δ=7.47-7.44 (2H, m), 7.33-7.26 (6H, m), 7.21-7.20 (1H, m), 6.83-6.80 (4H, m), 3.79 (6H, s), 3.34 (2H, s), 3.30-3.25 (2H, t, J=6.6 Hz), 3.06-3.02 (2H, t, J=6.3 Hz), 1.64-1.50 (6H, m), 1.38-1.25 (14H, m).

(5) hydroxydodecanamidoglycine-4,4'-dimethoxytrityloxydodecanamide (compound 5)

Compound 4 (3.15 g, 5.62 mmol) was azeotropically dried three times with anhydrous pyridine, 12-hydroxydodecanoic acid (3.41 g, 6.74 mmol), 1-ethyl-3-(3-dimethylaminopropyl)carbodiimide hydrochloride (1.29 g, 6.74 mmol), 1-hydroxybenzotriazole monohydrate (2.06 g, 13.48 mmol), and anhydrous dichloromethane (50 mL) were added at room temperature under an argon atmosphere, and the mixture was stirred for 10 min. Triethylamine (2.05 g, 20.22 mmol) was added to the thus-obtained mixture, and the mixture was stirred at room temperature overnight under an argon atmosphere. Dichloromethane (200 mL) was added to the obtained reaction mixture, and the mixture was washed three times with saturated aqueous sodium bicarbonate, and further washed once with saturated brine. The organic layer was separated and dried over sodium sulfate, and the solvent was evaporated under reduced pressure. The obtained residue was subjected to silica gel column chromatography (eluent: dichloromethane-methanol (95:5)+0.05% pyridine) to give hydroxydodecanamidoglycine-4,4'-dimethoxytrityloxydodecanamide (5) (2.97 g, 70%) as a colorless syrup. The instrumental analytical values of hydroxydodecanamidoglycine-4,4'-dimethoxytrityloxydodecanamide (5) are shown below.

hydroxydodecanamidoglycine-4,4'-dimethoxytrityloxydodecanamide (5);
$^1$H-NMR (CDCl$_3$): δ=7.42-7.40 (2H, m), 7.33-7.26 (6H, m), 7.22-7.21 (1H, m), 6.83-6.80 (4H, m), 3.84 (2H, s), 3.79 (6H, s), 3.64-3.61 (2H, t, J=6.3 Hz), 3.26-3.24 (2H, t, J=6.1 Hz), 3.08-3.06 (2H, t, J=5.6 Hz), 2.28-2.24 (2H, t, J=6.8 Hz), 1.69-1.52 (12H, m), 1.44-1.39 (26H, m).

(6) dodecanamidoglycine-4,4'-dimethoxytrityloxydodecanamido phosphoramidite (compound 6)

Compound 5 (2.78 g, 3.76 mmol) was azeotropically dried three times with anhydrous pyridine. Then, diisopropylammonium tetrazolide (772 mg, 4.51 mmol) was added, the mixture was deaerated under reduced pressure and filled with argon gas, and anhydrous acetonitrile (3 mL) was added. Furthermore, a solution (3 mL) of 2-cyanoethoxy-N,N,N',N'-tetraisopropyl phosphorodiamidite (1.36 g, 4.51 mmol) in anhydrous acetonitrile-dichloromethane was added, and the mixture was stirred at room temperature for 4 hr under an argon atmosphere. Dichloromethane (150 mL) was added to the obtained reaction mixture, and the mixture was washed twice with saturated aqueous sodium bicarbonate, and further washed once with saturated brine. The organic layer was separated and dried over sodium sulfate, and the solvent was evaporated under reduced pressure. The residue was subjected to column chromatography using amino silica (eluent: n-hexane-acetone (7:3)+0.05% pyridine) to give dodecanamidoglycine-4,4'-dimethoxytrityloxydodecanamido phosphoramidite (6) (2.72 g, 77%, HPLC 98.5%). The instrumental analytical values of dodecanamidoglycine-4,4'-dimethoxytrityloxydodecanamido phosphoramidite (6) are shown below.

dodecanamidoglycine-4,4'-dimethoxytrityloxydodecanamido phosphoramidite (6);

$^1$H-NMR (CDCl$_3$): δ=7.41-7.49 (m, 2H), 7.26-7.30 (m, 6H), 7.17-7.19 (m, 1H), 6.80-6,83(m, 4H), 6.46-6.62 (m, 2H), 4.07-4.29 (m, 2H), 3.89 (d, J=5.4 Hz, 2H), 3.75-3.87 (m, 4H), 3.67 (s, 6H), 3.47-3.70 (m, 4H), 3.20-3.26 (m, 2H), 3.02 (t, J=6.4 Hz, 2H, CH$_2$), 2.63 (t, 6.4 Hz, 2H, CH$_3$), 1.56-1.63 (m, 6H), 1.47-1.51 (m, 2H), 1.24-1.33 (m, 26H), 1.13-1.20 (m, 12H):

P-NMR(CDCl$_3$): δ=146.62.

Example B1

Solid Phase Synthesis of RNA

RNA having the linker of the present invention (single-stranded nucleic acid molecule of the present invention) was synthesized. RNA was synthesized from the 3' side toward the 5' side by a nucleic acid synthesizer (trade name: ABI Expedite (registered trademark) 8909 Nucleic Acid Synthesis System, Applied Biosystems) based on the phosphoramidite method. For the aforementioned synthesis, RNA Phosphoramidites (2'-O-TBDMSi, trade name, Samchully Pharm. Co., Ltd.) was used as RNA amidite (hereinafter the same). The aforementioned amidite was deprotected by a conventional method, and the synthesized RNA was purified by HPLC. In the following examples, RNA was synthesized in the same manner, unless otherwise indicated.

To be specific, a single-stranded RNA (ssRNA), wherein the structures of linker regions (Lx) and (Ly) are each represented by the following chemical formula Lg, was synthesized as the RNA (Ex) of the present Example, by using the aforementioned compound (6) of the aforementioned scheme 5 as the monomer of the present invention. (Lg [structure of Lx or Ly])

—O(CH$_2$)$_{11}$CO-Gly-NH(CH$_2$)$_{12}$O—

First, RNA having the sequence shown by SEQ ID NO: 1 below was synthesized. Then, the aforementioned compound 6 was linked to the 5' end of the aforementioned RNA. Then, RNA having the sequence shown by SEQ ID NO: 2 below was linked via the aforementioned compound 6 to the 5' side of the aforementioned RNA shown by SEQ ID NO: 1. Furthermore, the aforementioned compound 6 was linked to the 5' end of the aforementioned RNA shown by SEQ ID NO: 2. Furthermore, ssRNA of Example was synthesized by linking the RNA with the sequence shown by SEQ ID NO: 3 below to the 5' side of the aforementioned RNA shown by SEQ ID NO: 2, via the aforementioned compound 6.

```
                                              (SEQ ID NO: 1)
        5'-GAA-3'

(SEQ ID NO: 2)
        5'-GGCUGUUGUCAUACUUCUCAUGGUUC-3'

(SEQ ID NO: 3)
        5'-CAUGAGAAGUAUGACAACAGCC-3'
```

The ssRNA of Example synthesized as mentioned above is hereafter referred to as PK-0054. The aforementioned PK-0054 has a structure wherein, as shown by SEQ ID NO: 4 below, the aforementioned RNA of SEQ ID NO: 3, the aforementioned RNA of SEQ ID NO: 2, and the aforementioned RNA of SEQ ID NO: 1 are aligned in this order from the 5' side, the aforementioned RNA of SEQ ID NO: 3 (corresponding to Xc) and the aforementioned RNA of SEQ ID NO: 2 (corresponding to inner region Z) are linked via linker Lx (the aforementioned structure Lg), and the aforementioned RNA of SEQ ID NO: 2 (corresponding to inner region Z) and the aforementioned RNA of SEQ ID NO: 1 (corresponding to Yc) are linked via linker Ly (the aforementioned structure Lg). Furthermore, as shown in the following sequence, the aforementioned RNA sequence of SEQ ID NO: 2 is complementary to the aforementioned RNA sequence of SEQ ID NOs: 1 and 3. Hence, the aforementioned PK-0054 performs self-annealing to have a stem structure, as shown in the formula below. In the following sequence, the underlined part "GUUGUCAUACUUCUCAUGG" (SEQ ID NO: 5) is a region involved in the inhibition of the GAPDH gene expression.

```
                                              (SEQ ID NO: 4)
Ex: PK-0054

5'-CAUGAGAAGUAUGACAACAGCC-Lx-GGCUGUUGUCAUACUUCUCAUGGUUC-Ly-GAA-3'
   _____/   _____/   \_/
            Xc                          Z                   Yc
                            (SEQ ID NO: 5)
Expression inhibitory region of PK-0054

5'-GUUGUCAUACUUCUCAUGG-3'

GAA  CAUGAGAAGUAUGACAACAGCC
PK-0054    Ly                                           Lx
                CUUGGUACUCUUCAUACUGUUGUCGG
```

In the same manner as with PK-0054 except that the RNA of the following SEQ ID NO: 6 was used instead of the aforementioned RNA shown by SEQ ID NO: 2, and the RNA of the following SEQ ID NO: 7 was used instead of the aforementioned RNA shown by SEQ ID NO: 3, other ssRNA of Example was synthesized. Hereinafter this is referred to as PK-0055.

```
                                              (SEQ ID NO: 1)
        5'-GAA-3'

(SEQ ID NO: 6)
        5'-GGCUUUCACUUAUCGUUGAUGGCUUC-3'
```

-continued (SEQ ID NO: 7)
```
5'-CCAUCAACGAUAAGUGAAAGCC-3'
```

The aforementioned PK-0055 has a structure wherein, as shown by SEQ ID NO: 8 below, the aforementioned RNA shown by SEQ ID NO: 7, the aforementioned RNA shown by SEQ ID NO: 6, and the aforementioned RNA shown by SEQ ID NO: 1 are aligned in this order from the 5' side, the aforementioned RNA shown by SEQ ID NO: 7 (corresponding to Xc) and the aforementioned RNA shown by SEQ ID NO: 6 (corresponding to inner region Z) are linked via linker Lx (the aforementioned structure Lg), and the aforementioned RNA shown by SEQ ID NO: 6 (corresponding to inner region Z) and the aforementioned RNA shown by SEQ ID NO: 1 (corresponding to Yc) are linked via linker Ly (the aforementioned structure Lg). In addition, as shown in the sequences below, the aforementioned RNA sequence shown by SEQ ID NO: 6 is complementary to the aforementioned RNA sequences shown by SEQ ID NOs: 1 and 7. Hence, the aforementioned PK-0055 performs self-annealing to have a stem structure, as shown in the formula below.

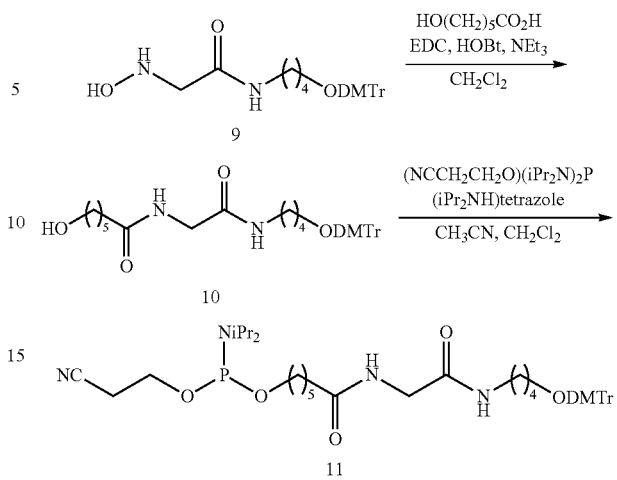

(SEQ ID NO: 8)
```
Ex: PK-0055
5'-CCAUCAACGAUAAGUGAAAGCC-Lx-GGCUUUCACUUAUCGUUGAUGGCUUC-Ly-GAA-3'
              Xc                          Z                       Yc

GAA  CCAUCAACGAUAAGUGAAAGCC
PK-0055  Ly                                Lx
            CUUCGGUAGUUGCUAUUCACUUUCGG
```

Example A2

According to the following scheme 6, butanamidoglycine-4,4'-dimethoxytrityloxybutanamido phosphoramidite (11) was synthesized. Compound (11) is one embodiment of the aforementioned monomer of the present invention. In addition, compound (11) corresponds to a compound (6) (scheme 5, Example A1) wherein the methylene chain directly bound to the both ends of —CO-Gly-NH— has a different carbon number.

scheme 6

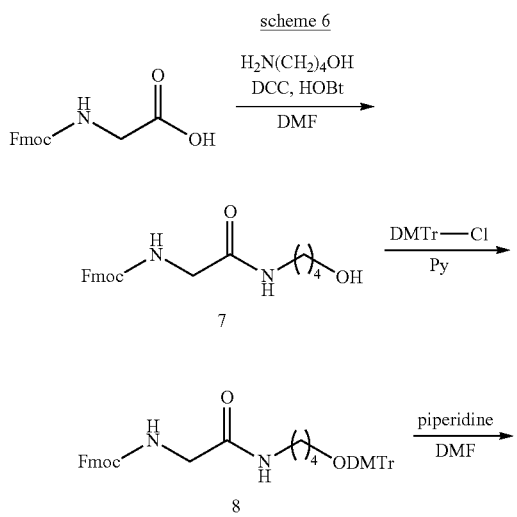

(1) Fmoc-glycine-butanamide (compound 7)

To a solution (100 mL) of Fmoc-glycine (4.00 g, 13.45 mmol), dicyclohexylcarbodiimide (3.33 g, 16.15 mmol) and 1-hydroxybenzotriazole monohydrate (4.94 g, 32.29 mmol) in anhydrous N,N-dimethylformamide was added a solution (30 mL) of 4-aminobutanol (1.44 g, 16.15 mmol) in anhydrous N,N-dimethylformamide, and the mixture was stirred at room temperature overnight under an argon atmosphere. The resultant precipitate was separated by filtration, and the filtrate was concentrated under reduced pressure. Dichloromethane (200 was added to the obtained residue, and the mixture was washed three times with saturated aqueous sodium bicarbonate, and further washed with saturated brine. After drying over sodium sulfate, the solvent was evaporated under reduced pressure. The obtained residue was subjected to silica gel column chromatography (eluent: dichloromethane-methanol (95:5)) to give Fmoc-glycine-butanamide (7) (4.30 g, 87%). The instrumental analytical values of Fmoc-glycine-butanamide (7) are shown below.

Fmoc-glycine-butanamide (7);
$^1$H-NMR (CDCl$_3$): δ=7.78-7.76 (2H, d, J=7.3 Hz), 7.65-7.63 (2H, d, J=7.3 Hz), 7.42-7.41 (2H, t, J=7.6 Hz), 7.34-7.30 (2H, td, J=7.6, 1.1 Hz), 4.42-4.40 (2H, d, J=7.3 Hz), 4.25-4.22 (1H, t, J=6.8 Hz), 3.83 (2H, s), 3.60-3.55 (2H, m), 3.30-3.25 (2H, m), 1.61-1.55 (4H, m).

(2) Fmoc-glycine-4,4'-dimethoxytrityloxybutanamide (compound 8)

Compound 7 (4.20 g, 11.40 mmol) was azeotropically dried three times with anhydrous pyridine. 4,4'-Dimethoxytrityl chloride (5.80 g, 17.10 mmol) and anhydrous pyridine (80 mL) were added to the residue by azeotropy, and the mixture was stirred at room temperature overnight. Methanol (20 mL) was added to the obtained reaction mixture and the mixture was stirred at room temperature for 30 min, and the solvent was evaporated under reduced pressure. Thereafter, dichloromethane (200 mL) was added, and the mixture was washed three times with saturated aqueous sodium bicarbonate, and further washed with saturated brine. After drying over sodium sulfate, the solvent was evaporated under reduced pressure to give unpurified Fmoc-glycine-4,4'-dimethoxytrityloxybutanamide (8) (11.40 g).

(3) glycine-4,4'-dimethoxytrityloxybutanamide (compound 9)

To the unpurified compound 8 (11.40 g, 16.99 mmol) were added N,N-dimethylformamide (45 mL) and piperidine (11.7 mL) at room temperature, and the mixture was stirred at room temperature overnight. The solvent in the reaction mixture was evaporated under reduced pressure, and the obtained residue was subjected to silica gel column chromatography (eluent: dichloromethane-methanol (9:1)+ 0.05% pyridine) to give glycine-4,4'-dimethoxytrityloxybutanamide (9) (4.90 g, 96%, 2 steps). The instrumental analytical values of glycine-4,4'-dimethoxytrityloxybutanamide (9) are shown below.

glycine-4,4'-dimethoxytrityloxybutanamide (9);
$^1$H-NMR (CDCl$_3$): δ=7.44-7.42 (2H, m), 7.33-7.26 (6H, m), 7.21-7.20 (1H, m), 6.83-6.80 (4H, m), 3.79 (6H, s), 3.49 (2H, s), 3.30-3.28 (2H, t, J=6.3 Hz), 3.09-3.06 (2H, t, J=5.9 Hz), 1.61-1.55 (4H, m).

(4) hydroxyhexanamidoglycine-4,4'-dimethoxytrityloxybutanamide (compound 10)

Compound 9 (4.80 g, 10.70 mmol) was azeotropically dried three times with anhydrous pyridine, 6-hydroxyhexanoic acid (1.70 g, 12.84 mmol), 1-ethyl-3-(3-dimethylaminopropyl)carbodiimide hydrochloride (2.46 g, 12.84 mmol), 1-hydroxybenzotriazole monohydrate (3.93 g, 25.69 mmol), and anhydrous dichloromethane (60 mL) were added at room temperature under an argon atmosphere, and the mixture was stirred for 10 min. Triethylamine (3.90 g, 38.53 mmol) was added to the thus-obtained mixture, and the mixture was stirred at room temperature overnight under an argon atmosphere. Dichloromethane (200 mL) was added to the obtained reaction mixture, and the mixture was washed three times with saturated aqueous sodium bicarbonate, and further washed once with saturated brine. The organic layer was separated and dried over sodium sulfate, and the solvent was evaporated under reduced pressure. The obtained residue was subjected to silica gel column chromatography (eluent: dichloromethane-methanol (95:5)+ 0.05% pyridine) to give hydroxyhexanamidoglycine-4,4'-dimethoxytrityloxybutanamide (10) (4.80 g, 80%). The instrumental analytical values of hydroxyhexanamidoglycine-4,4'-dimethoxytrityloxybutanamide (10) are shown below.

hydroxyhexanamidoglycine-4,4'-dimethoxytrityloxybutanamide (10);
$^1$H-NMR (CDCl$_3$): δ=7.43-7.40 (2H, m), 7.33-7.26 (6H, m), 7.22-7.20 (1H, m), 6.83-6.80 (4H, m), 3.85 (2H, s), 3.78 (6H, s), 3.63-3.60 (2H, t, J=6.3 Hz), 3.26-3.23 (2H, t, J=6.1 Hz), 3.07-3.05 (2H, t, J=5.6 Hz), 2.26-2.22 (2H, t, J=7.3 Hz), 1.68-1.52 (8H, m), 1.41-1.36 (2H, m).

(5) hydroxyhexanamidoglycine-4,4'-dimethoxytrityloxybutanamido phosphoramidite (compound 11)

Compound 10 (4.70 g, 8.35 mmol) was azeotropically dried three times with anhydrous pyridine. Then, diisopropylammonium tetrazolide (1.72 g, 10.02 mmol) was added, the mixture was deaerated under reduced pressure and filled with argon gas, and anhydrous acetonitrile (5 mL) was added. Furthermore, a solution (4 mL) of 2-cyanoethoxy-N,N,N',N'-tetraisopropyl phosphorodiamidite (3.02 g, 10.02 mmol) in a 1:1 anhydrous acetonitrile-dichloromethane mixture was added, and the mixture was stirred at room temperature for 4 hr under an argon atmosphere. Dichloromethane (150 mL) was added to the obtained reaction mixture, and the mixture was washed twice with saturated aqueous sodium bicarbonate, and further washed once with saturated brine. The organic layer was separated and dried over sodium sulfate, and the solvent was evaporated under reduced pressure. The residue was subjected to column chromatography using amino silica (eluent: n-hexane-acetone (3:2) 0.1% triethylamine) to give hydroxyhexanamidoglycine-4,4'-dimethoxytrityloxybutanamido phosphoramidite (11) (4.50 g, 71%, HPLC 98.2%). The instrumental analytical values of hydroxyhexanamidoglycine-4,4'-dimethoxytrityloxybutanamido phosphoramidite (11) are shown below.

hydroxyhexanamidoglycine-4,4'-dimethoxytrityloxybutanamido phosphoramidite (11);
$^1$H-NMR (CDCl$_3$): δ=7.43-7.40 (2H, m), 7.33-7.26 (6H, m), 7.22-7.20 (1H, m), 6.83-6.80 (4H, m), 3.85-3.81 (4H, s), 3.78 (6H, s), 3.63-3.61 (2H, t, J=6.3 Hz), 3.26-3.23 (2H, t, J=6.1 Hz), 3.05-2.97 (4H, m), 2.64-2.62 (2H, t, J=6.4 Hz), 2.25-2.23 (2H, t, J=7.3 Hz), 1.68-1.52 (8H, m), 1.40-1.38 (2H, m), 1.13-1.20 (12H, m). $^{31}$P-NMR(CDCl$_3$): δ=146.57.

Example A3

According to the following scheme 7, monomer (11) which is a lysine derivative was synthesized. In the following scheme 7, "Tfa" is a trifluoroacetyl group.

scheme 7

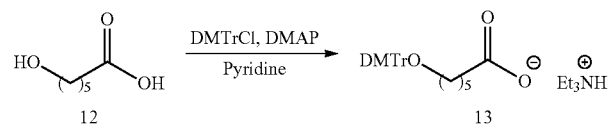

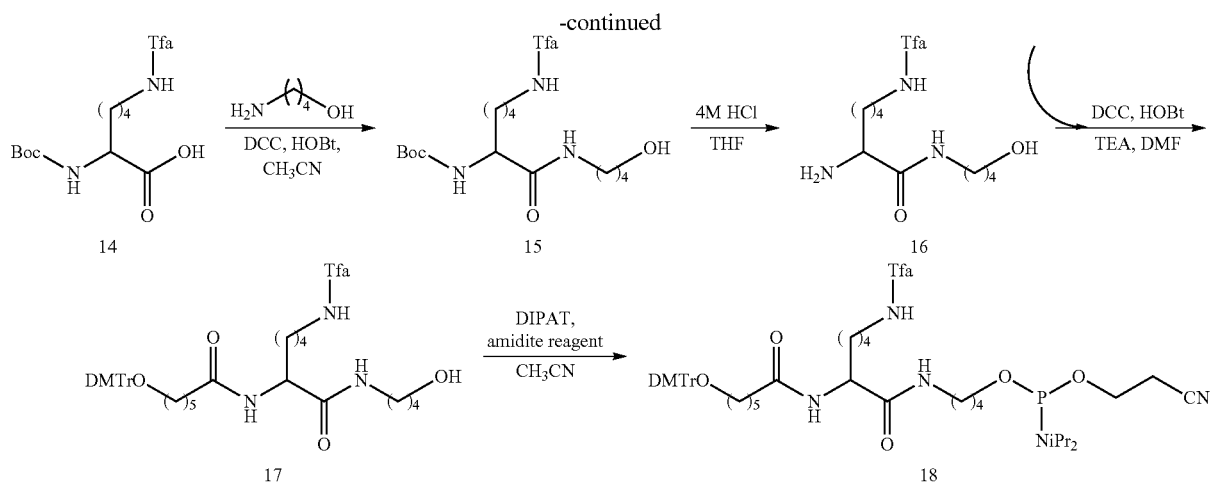

(1) Synthesis of Compound (13)

To a solution (124 mL) of 6-hydroxyhexanoic acid (compound 12) (6 g, 15.1 mmol) in pyridine were added 4,4'-dimethoxytrityl chloride (20 g, 1.3 eq.) and dimethylaminopyridine (0.5 g, 0.1 eq.), and the mixture was stirred at room temperature for 20 hr. After completion of the reaction, methanol (10 mL) was added, the mixture was stirred for 10 min, and the solvent was evaporated. The reaction mixture was diluted with ethyl acetate, washed three times with TEAA buffer (pH 8-9), and washed once with saturated brine. The organic layer was dried over sodium sulfate, and the solvent was evaporated under reduced pressure to give compound 13 (31 g, pyridine-containing) as a pale-yellow oily substance.

(2) Synthesis of Compound (15)

To a solution (45 mL) of compound 14 (2.7 g, 7.9 mmol), dicyclohexylcarbodiimide (1.9 g, 1.2 eq.), and 1-hydroxybenzotriazole monohydrate (2.6 g, 2.4 eq.) in acetonitrile was added a solution (5 mL) of 4-amino-1-butanol (0.86 g, 1.2 eq.) in acetonitrile, and the mixture was stirred at room temperature for 16 hr. After completion of the reaction, the precipitate was collected by filtration, and the solvent in the filtrate was evaporated by an evaporator. Dichloromethane was added to the obtained residue, and the mixture was washed three times with acetate buffer (pH 4) and three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=10/1) to give compound (15) (2.8 g, yield 85%) as a white solid. The instrumental analytical values of compound (15) are shown below.

compound (15);
$^1$H-NMR (400 MHz, CDCl$_3$) δ:7.07 (br, 1H), 6.72 (t, J=5.6 Hz, 1H), 4.03 (m, 1H), 3.66 (d, J=4.9 Hz, 2H), 3.37 (dd, J=12.9, 6.3 Hz, 2H), 3.29 (dd, J=12.4, 6.3 Hz, 2H), 1.83 (s, 2H), 1.66-1.60 (m, 6H), 1.44 (s, 9H), 1.41-1.37 (m, 2H)

(3) Synthesis of Compound (16)

Compound 15 (2.5 g, 6.1 mmol) was stirred in hydrochloric acid/tetrahydrofuran solution (4 M, 45 mL) at room temperature for 2 hr. After completion of the reaction, the solvent was evaporated under reduced pressure. The obtained residue was dissolved in ethanol, and azeotroped with toluene. The solvent was evaporated to give compound (16) (1.9 g) as a white solid. The instrumental analytical values of compound (16) are shown below.

compound (16);
$^1$H-NMR (400 MHz, CD$_3$OD) δ: 3.85-3.81 (m, 1H), 3.59-3.56 (m, 2H), 3.32-3.20 (m, 2H), 1.94-1.80 (m, 2H), 1.66-1.58 (m, 6H), 1.46-1.40 (m, 2H)

(4) Synthesis of Compound (17)

To a solution (150 mL) of compound 13 (pyridine-containing, 24 g, 35.5 mmol), dicyclohexylcarbodiimide (8.8 g, 1.2 eq.), and 1-hydroxybenzotriazole monohydrate (7.2 g, 1.5 eq.) was added triethylamine (4.5 mL, 0.9 eq.), a solution (30 mL) of compound 16 (10 g, 0.9 eq.) in N,N-dimethylformamide was further added, and the mixture was stirred at room temperature for 20 hr. After completion of the reaction, the precipitate was collected by filtration, and the solvent in the filtrate was evaporated by an evaporator. Dichloromethane was added to the obtained residue, and the mixture was washed three times with saturated aqueous sodium bicarbonate. The organic layer was dried over sodium sulfate, and the solvent was evaporated under reduced pressure. The obtained crude product was purified by silica gel column chromatography (eluent: dichloromethane/methanol=20/1+0.05% pyridine) to give compound (17) (16 g, yield 70%) as a pale-yellow solid. The instrumental analytical values of compound (17) are shown below.

compound (17);
$^1$H-NMR (400 MHz, CDCl$_3$) δ: 7.43-7.40 (m, 2H), 7.32-7.26 (m, 6H), 7.21-7.17 (m, 1H), 6.81 (d, J=8.8 Hz, 4H), 4.39-4.37 (m, 1H), 3.78 (s, 6H), 3.64-3.61 (m, 2H), 3.33-3.22 (m, 4H), 3.03 (t, J=6.6 Hz, 2H), 2.19 (t, J=7.6 Hz, 2H), 1.79-1.54 (m, 12H), 1.40-1.34 (m, 4H)

(5) Synthesis of Compound (18)

To a solution (3.5 mL) of compound (17) (1.26 g, 1.73 mmol), which was azeotropically dried by acetonitrile, in anhydrous acetonitrile were added diisopropylammonium tetrazolide (394 mg, 1.3 eq.) and 2-cyanoethoxy-N,N,N',N'-tetraisopropyl phosphorodiamidite (700 mg, 1.3 eq.), and the mixture was stirred at room temperature for 2.5 hr. Dichloromethane was added, the mixture was washed with saturated aqueous sodium bicarbonate and saturated brine and dried over sodium sulfate, and the solvent was evaporated. The obtained crude product was purified by silica gel column chromatography (amino silica, eluent: n-hexane/ethyl acetate=2/3) to give compound (18) (1.3 g, yield 78%) as a white solid. The instrumental analytical values of compound (18) are shown below.

compound (18);

$^1$H-NMR (400 MHz, CDCl$_3$) δ: 7.43-7.41 (m, 2H), 7.32-7.17 (m, 7H), 6.81 (dt, J=9.3, 2.9 Hz, 4H), 4.42-4.37 (m, 1H), 3.78 (s, 6H), 3.88-3.54 (m, 6H), 3.32-3.20 (m, 4H), 3.03 (t, J=6.3 Hz, 2H), 2.19 (t, J=7.6 Hz, 2H), 1.83-1.53 (m, 12H), 1.42-1.31 (m, 4H), 1.28-1.24 (m, 2H), 1.18-1.16 (m, 12H)

$^{31}$P-NMR (162 MHz, CDCl$_3$) δ: 146.9

Example B3

Solid Phase Synthesis of RNA

In the same manner as in the aforementioned Example B1 except that the aforementioned compound (18) in the aforementioned scheme 7 was used as the monomer of the present invention instead of the aforementioned compound (6) in the aforementioned scheme 5, guanosine was used instead of the aforementioned RNA shown by SEQ ID NO: 1, the RNA shown by the following SEQ ID NO: 63 was used instead of the aforementioned RNA shown by SEQ ID NO: 2 and the RNA shown by the following SEQ ID NO: 64 was used instead of the aforementioned RNA shown by SEQ ID NO: 3, RNA of the Example was solid phase synthesized. The RNA of the Example synthesized in this way is a single-stranded RNA (ssRNA) wherein the linker regions (Lx) and (Ly) each have a structure represented by the following chemical formula L1. The linker region (Lx) (represented by the following chemical formula L1) in the RNA in this Example is referred to as "Lx'" in the following to distinguish from the linker region (Lx) (represented by the aforementioned chemical formula Lg) in the aforementioned Example B1. Similarly, the linker region (Ly) (represented by the following chemical formula L1) in the RNA in this Example is referred to as "Ly'" in the following to distinguish from the linker region (Ly) (represented by the aforementioned chemical formula Lg) in the aforementioned Example B1.

(SEQ ID NO: 63)
5'-GGAAUCGAAGUACUCAGCGUAAGUUC-3'

(SEQ ID NO: 64)
5'-ACUUACGCUGAGUACUUCGAUUCC-3'

(L1 [structure of Lx' or Ly'])

—O(CH$_2$)$_5$CO-Lys-NH(CH$_2$)$_4$O—

In the structure L1 of the aforementioned linker, "Lys" is a structure represented by the following chemical formula.

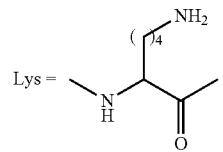

Therefore, structure L1 of the aforementioned linker is represented by the following chemical formula.

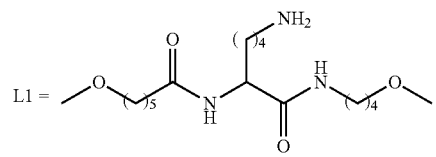

The ssRNA of this Example synthesized as mentioned above is hereinafter to be referred to as PK-0100. The aforementioned PK-0100 has a structure wherein, as shown by SEQ ID NO: 65 below, the aforementioned RNA shown by SEQ ID NO: 64, the aforementioned RNA shown by SEQ ID NO: 63, and guanosine are aligned in this order from the 5' side, the aforementioned RNA shown by SEQ ID NO: 64 (corresponding to Xc) and the aforementioned RNA shown by SEQ ID NO: 63 (corresponding to inner region Z) are linked via linker Lx' (the aforementioned structure L1), and the aforementioned RNA shown by SEQ ID NO: 63 (corresponding to inner region Z) and guanosine (corresponding to Yc) are linked via linker Ly' (the aforementioned structure L1). In addition, as shown in the sequences below, the aforementioned RNA sequence shown by SEQ ID NO: 63 is complementary to guanosine and the aforementioned RNA sequence shown by SEQ ID NO: 64. Hence, the aforementioned PK-0100 performs self-annealing to have a stem structure, as shown in the formula below.

(SEQ ID NO: 65)

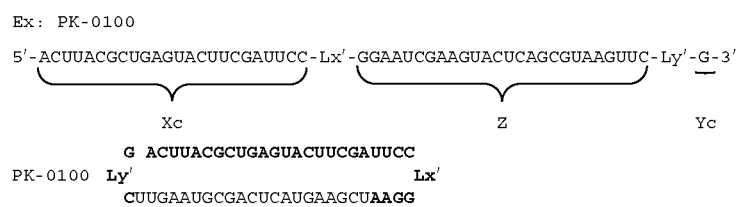

Reference Example A1

A synthesis material monomer of the single-stranded nucleic acid containing a proline skeleton was produced according to the following scheme 8.

scheme 8

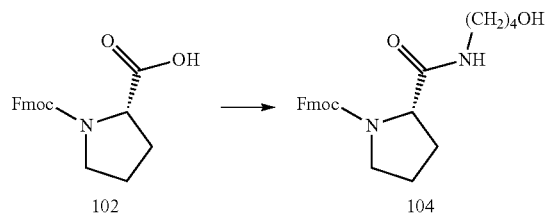

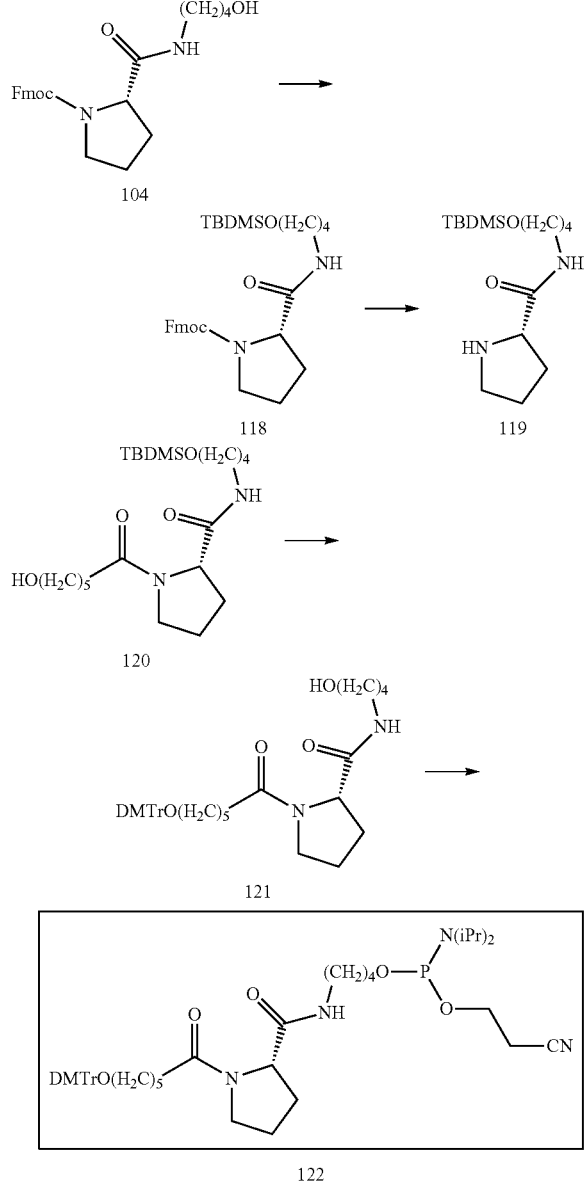

Fmoc: 9-fluorenylmethyloxycarbonyl
TBDMS: tert-butyldimethylsilyl
DMTr: 4,4'-dimethoxytrityl (1) Fmoc-hydroxyamido-L-proline (compound 104)

Compound 102 (Fmoc-L-proline), which is the starting material of the aforementioned Scheme 8 was purchased from Tokyo Chemical Industry Co., Ltd. This compound 102 (10.00 g, 29.64 mmol), 4-amino-1-butanol (3.18 g, 35.56 mmol), and 1-hydroxybenzotriazole (10.90 g, 70.72 mmol) were mixed together. The aforementioned mixture was deaerated under reduced pressure and filled with argon gas. Anhydrous acetonitrile (140 mL) was added to the aforementioned mixture at room temperature, and a solution (70 mL) of dicyclohexylcarbodiimide (7.34 g, 35.56 mmol) in anhydrous acetonitrile was further added thereto. Thereafter, this was stirred for 15 hours at room temperature under an argon atmosphere. After the completion of the reaction, the generated precipitate was removed by filtration, and the solvent in the collected filtrate was evaporated under reduced pressure. Dichloromethane (200 mL) was added to the obtained residue, and the mixture was washed with saturated aqueous sodium bicarbonate (200 mL). Then, an organic layer m was collected and dried over magnesium sulfate. Thereafter, the aforementioned organic layer was filtered, and the solvent in the obtained filtrate was evaporated under reduced pressure. Diethyl ether (200 mL) was added to the residue, thereby turning the residue to powder. The thus-obtained powder was collected by filtration. Thus, compound 104 in the form of colorless powder was obtained (10.34 g, yield 84%). The result of instrumental analysis with respect to the aforementioned compound 104 is shown below.

Fmoc-hydroxyamido-L-proline (104);
$^1$H-NMR (CDCl$_3$): δ7.76-7.83 (m, 2H, Ar—H), 7.50-7.63 (m, 2H, Ar—H), 7.38-7.43 (m, 2H, Ar—H), 7.28-7.33 (m, 2H, Ar—H), 4.40-4.46 (m, 1H, CH), 4.15-4.31 (m, 2H, CH$_2$), 3.67-3.73 (m, 2H, CH$_2$), 3.35-3.52 (m, 2H, CH$_2$) 3.18-3.30 (m, 2H, CH$_2$), 2.20-2.50 (m, 4H), 1.81-2.03 (m, 3H), 1.47-1.54 (m, 2H);
MS (FAB+): m/z409(M+H$^+$).

(2) Fmoc-t-butyl-dimethylsiloxyamido-L-proline (compound 118)

Fmoc-hydroxyamido-L-proline (compound 104) (2.00 g, 30 mmol), t-butyl-dimethylsilyl chloride (1.11 g, 35 mmol), and imidazole (10.90 g, 71 mmol) were mixed together. The aforementioned mixture was deaerated under reduced pressure and filled with argon gas. Anhydrous acetonitrile (20 mL) was added to the aforementioned mixture at room temperature, and this was stirred overnight at room temperature under an argon atmosphere. After the completion of the reaction, dichloromethane (150 mL) was added to the aforementioned mixture. The resultant mixture was washed with water three times and then with saturated brine. An organic layer was collected and dried over magnesium sulfate. Thereafter, the aforementioned organic layer was filtered. The solvent in the obtained filtrate was evaporated under reduced pressure, and the residue was applied to silica gel column chromatography (the eluent: CH$_2$Cl$_2$:CH$_3$OH=95:5). Thus, compound 118 in the form of colorless syrup was obtained (2.35 g, yield 92%). The result of instrumental analysis with respect to the aforementioned compound 118 is shown below.

Fmoc-t-butyl-dimethylsiloxyamido-L-proline (118);
$^1$H-NMR (CDCl$_3$): δ7.76-7.78 (m, 2H, Ar—H), 7.50-7.63 (m, 2H, Ar—H), 7.38-7.42 (m, 2H, Ar—H), 7.29-7.34 (m, 2H, Ar—H), 4.10-4.46 (m, 4H, CH$_2$), 3.47-3.59 (m, 4H, CH$_2$), 3.20-3.26 (m, 2H, CH), 1.85-1.95 (m, 2H), 1.42-1.55 (m, 6H), 0.96 (s, 9H, t-Bu), 0.02 (s, 6H, SiCH$_3$);
MS(FAB+): m/z 523(M+H$^+$).

(3) t-butyl-dimethylsiloxyamido-L-proline (compound 119)

To the aforementioned Fmoc-t-butyl-dimethylsiloxyamido-L-proline (compound 118) (1.18 g, 2.5 mmol) obtained above, anhydrous acetonitrile (5 mL) and piperidine (2.4 mL) were added, and this was stirred for 1 hour at room temperature. After the completion of the reaction, acetonitrile (50 mL) was added to the aforementioned mixture, and insoluble matters were removed by filtration. The solvent in the obtained filtrate was evaporated under reduced pressure. The obtained residue was applied to silica gel column chromatography (the eluent: CH$_2$Cl$_2$:CH$_3$OH=9:1).

Thus, compound 119 in the form of colorless syrup was obtained (0.61 g, yield 90%). The result of instrumental analysis with respect to the aforementioned compound 119 is shown below.

t-butyl-dimethylsiloxyamido-L-proline (119);
$^1$H-NMR (CDCl$_3$): δ3.71 (dd, 1H, J=9.0 Hz, 5.2 Hz, CH), 3.61-3.64 (m, 2H, CH$_2$), 3.22-3.28 (m, 2H, CH$_2$), 2.98-3.04 (m, 1H, CH), 2.86-2.91 (m, 1H, CH), 2.08-2.17 (m, 1H, CH), 1.86-1.93 (m, 1H, CH), 1.66-1.75 (m, 2H, CH$_2$), 1.52-1.57 (m, 4H), 0.89 (s, 9H, t-Bu). 0.05 (s, 6H, SiCH$_3$);
MS(FAB+); m/z 301(M+H$^+$).

(4)
t-butyl-dimethylsiloxyamidohydroxyamido-L-proline (compound 120)

The above-mentioned t-butyl-dimethylsiloxyamido-L-proline (compound 119) (550 mg, 1.8 mmol) obtained above, 6-hydroxyhexanoic acid (300 mg, 2.3 mmol), EDC (434 mg, 2.3 mmol), and a solution (20 mL) of 1-hydroxybenzotriazole (695 mg, 4.5 mmol) in anhydrous dichloromethane were mixed. Triethylamine (689 mg, 6.8 mmol) was added to the aforementioned mixture at room temperature under an argon atmosphere, and then, this was stirred overnight at room temperature under an argon atmosphere. The aforementioned mixture was washed with saturated brine. An organic layer was collected, and the aforementioned organic layer was dried over sodium sulfate. Thereafter, the aforementioned organic layer was filtered. The solvent in the obtained filtrate was evaporated under reduced pressure. The obtained residue was applied to silica gel column chromatography (the eluent: CH$_2$Cl$_2$:CH$_3$OH=9:1). Thus, compound 120 in the form of colorless syrup was obtained (696 mg, yield 92%). The result of instrumental analysis with respect to the aforementioned compound 120 is shown below.

t-butyl-dimethylsiloxyamidohydroxyamido-L-proline (120);
$^1$H-NMR (CDCl$_3$): δ4.54 (d, 1H, CH), 3.58-3.67 (m, 5H), 3.52-3.56 (m, 1H, CH), 3.32-3.39 (m, 1H), 3.20-3.25 (m, 2H), 2.40-2.43 (m, 1H, CH), 2.33 (t, J=7.3 Hz, 2H, CH$_2$), 2.05-2.25 (m, 2H), 1.93-2.03 (m, 1H, CH), 1.75-1.85 (m, 1H, CH), 1.50-1.73 (m, 8H), 1.37-1.46 (m, 2H, CH$_2$), 0.87 (s, 9H, t-Bu), 0.04 (s, 6H, SiCH$_3$);
MS(FAB+): m/z 415 (M$^+$+1).

(5) DMTr-hydroxydiamido-L-proline (compound 121)

The aforementioned t-butyl-dimethylsiloxyamidohydroxyamido-L-proline (compound 120) (640 mg, 1.54 mmol) obtained above was mixed with anhydrous pyridine (1 mL), and this was azeotropically dried at room temperature. To the obtained residue, 4,4'-dimethoxytrityl chloride (657 mg, 1.85 mmol), DMAP (2 mg), and anhydrous pyridine (5 mL) were added, and this was stirred for 4 hours at room temperature. Thereafter, methanol (1 mL) was added thereto, and this was stirred for 30 minutes at room temperature. The aforementioned mixture was diluted with dichloromethane, and this was washed with saturated aqueous sodium bicarbonate. An organic layer was collected and dried over sodium sulfate. Thereafter, the aforementioned organic layer was filtered. The solvent in the obtained filtrate was evaporated under reduced pressure. To the obtained residue, anhydrous acetonitrile (5 mL) and a 1 mol/L tetrabutylammonium fluoride-containing tetrahydrofuran solution (1.42 mL, tetrabutylammonium fluoride 1.42 mmol) were added, and this was stirred overnight at room temperature. After the completion of the reaction, ethyl acetate (100 mL) was added to the aforementioned mixture. The resultant mixture was washed with water and then with saturated brine. An organic layer was collected and dried over sodium sulfate. Thereafter, the aforementioned organic layer was filtered. The solvent in the obtained filtrate was evaporated under reduced pressure. The obtained residue was applied to silica gel column chromatography (the eluent: CH$_2$Cl$_2$:CH$_3$OH=95:5, containing 0.05% pyridine). Thus, compound 121 in the form of colorless syrup was obtained (680 mg, yield 73%). The result of instrumental analysis with respect to the aforementioned compound 121 is shown below.

DMTr-hydroxydiamido-L-proline (121);
$^1$H-NMR (CDCl$_3$): δ7.41-7.44 (m, 2H, Ar—H), 7.26-7.33 (m, 4H, Ar—H), 7.18-7.21 (m, 2H, Ar—H), 7.17-7.21 (m, 1H, Ar—H), 6.80-6.84 (m, 4H, Ar—H), 4.51-4.53 (d, 6.8 Hz, 1H, CH), 3.79 (s, 6H$_2$OCH$_3$), 3.61 (dd, 2H, J=11 Hz, 5.4 Hz, CH$_2$), 3.50-3.54 (m, 1H, CH), 3.36-3.43 (m, 1H, CH), 3.20-3.26 (m, 2H, CH$_2$), 3.05 (t, J=6.4 Hz, 2H, CH$_2$), 2.38-2.45 (m, 1H, CH), 2.30 (t, J=7.8 Hz, 2H, CH$_2$), 2.05-2.25 (m, 1H, CH), 1.92-2.00 (m, 1H, CH), 1.75-1.83 (m, 1H, CH), 1.52-1.67 (m, 8H), 1.35-1.45 (m, 2H, CH$_2$);
MS(FAB+): m/z 602(M$^+$), 303(DMTr$^+$).

(6) DMTr-diamido-L-proline amidite type B (compound 122)

The aforementioned DMTr-hydroxydiamido-L-proline (compound 121) (637 mg, 1.06 mmol) obtained above was mixed with anhydrous acetonitrile, and the resultant mixture was azeotropically dried at room temperature. To the obtained residue, diisopropylammonium tetrazolide (201 mg, 1.16 mmol) was added, and the resultant mixture was deaerated under reduced pressure and filled with argon gas. Anhydrous acetonitrile (1 mL) was added to the aforementioned mixture, and an anhydrous acetonitrile solution (1 mL) of 2-cyanoethoxy-N,N,N',N'-tetraisopropyl phosphorodiamidite (350 mg, 1.16 mmol) was further added thereto. This mixture was stirred for 4 hours at room temperature under an argon atmosphere. The aforementioned mixture was diluted with dichloromethane, and this was washed with saturated aqueous sodium bicarbonate and saturated brine. An organic layer was collected and dried over sodium sulfate. Thereafter, the aforementioned organic layer was filtered. The solvent in the obtained filtrate was evaporated under reduced pressure. The obtained residue was applied to column chromatography using amino silica gel as a filler (the eluent:hexane:acetone=7:3). Thus, compound 122 in the form of colorless syrup was obtained (680 mg, purity: 95%, yield 76%). The result of instrumental analysis with respect to the aforementioned compound 122 is shown below.

DMTr-diamido-L-proline amidite (122);
$^1$H-NMR (CDCl$_3$): δ7.41-7.43 (m, 2H, Ar—H), 7.25-7.32 (m, 4H, Ar—H), 7.17-7.22 (m, 2H, Ar—H), 6.80-6.83 (m, 4H, Ar—H), 4.53 (d, J=7.8 Hz, 1H, CH), 3.75-3.93 (m, 3H), 3.79 (s, 6H$_2$OCH$_3$), 3.46-3.68 (m, 5H), 3.34-3.41 (m, 1H, CH), 3.10-3.31 (m, 1H, CH), 3.05 (t, J=6.3 Hz, 2H, CH$_2$), 2.62 (t, J=6.3 Hz, 2H, CH$_2$), 2.39-2.46 (m, 1H, CH), 2.29 (t, 7.3 Hz, 2H, CH$_2$), 2.03-2.19 (m, 1H, CH), 1.90-2.00 (m, 1H, CH), 1.70-1.83 (m, 1H, CH), 1.51-1.71 (m, 8H), 1.35-1.45 (m, 2H, CH$_2$), 1.18 (d, J=6.4 Hz, 6H, CH$_3$), 1.16 (d, J=6.4 Hz, 6H, CH$_3$);
P-NMR (CH$_3$CN) 5146.90;
MS (FAB+): m/z 803(M$^+$+1), 303(DMTr$^+$).

Reference Example B1

Solid Phase Synthesis of RNA

In the same manner as in PK-0054 of the aforementioned Example B1 except that the aforementioned compound 122 was used instead of the aforementioned compound 6 (monomer in the present invention) in the aforementioned scheme 5, and the structure of the part corresponding to linker regions (Lx) and (Ly) was the following Lp instead of the aforementioned Lg, a single-stranded RNA (ssRNA) was synthesized.

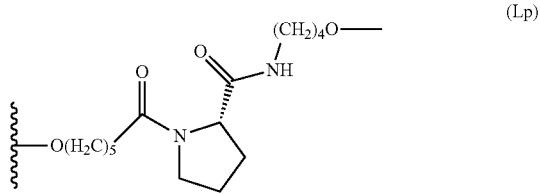

(Lp)

The ssRNA synthesized as mentioned above is hereinafter to be referred to as PK-0004. The aforementioned PK-0004 has a structure wherein, as shown by SEQ ID NO: 9 below, the aforementioned RNA shown by SEQ ID NO: 3, the aforementioned RNA shown by SEQ ID NO: 2, and the aforementioned RNA shown by SEQ ID NO: 1 are aligned in this order from the 5' side, and each RNA is linked via the aforementioned structure Lp. In addition, as explained in the aforementioned Example B1, the aforementioned RNA sequence shown by SEQ ID NO: 2 is complementary to the aforementioned RNA sequences shown by SEQ ID NOs: 1 and 3. Hence, the aforementioned PK-0004 performs self-annealing to have a stem structure, as shown in the formula below. Like the aforementioned PK-0054, the underlined part GUUGUCAUACUUCUCAUGG (SEQ ID NO: 5) is a region involved in the inhibition of the GAPDH gene expression.

```
                                       (SEQ ID NO: 1)
5'-GAA-3'

(SEQ ID NO: 2)
5'-GGCUGUUGUCAUACUUCUCAUGGUUC-3'

(SEQ ID NO: 3)
5'-CAUGAGAAGUAUGACAACAGCC-3'

Ex: PK-0004
                                       (SEQ ID NO: 9)
5'-CAUGAGAAGUAUGACAACAGCC-Lp-GGCUGUUGUCAUACUUCUCAU

GGUUC-Lp-GAA-3' expression inhibitory region of PK-0004
                                       (SEQ ID NO: 5)
5'-GUUGUCAUACUUCUCAUGG-3'

PK-0004
   GAA  CAUGAGAAGUAUGACAACAGCC
Lp                                Lp
   CUUGGUACUCUUCAUACUGUUGUCGG
```

In the same manner as with PK-0004 except that the RNA of the following SEQ ID NO: 6 was used instead of the aforementioned RNA shown by SEQ ID NO: 2, and the RNA of the following SEQ ID NO: 7 was used instead of the aforementioned RNA shown by SEQ ID NO: 3, other ssRNA of Reference Example was synthesized. Hereinafter this is referred to as PK-0003.

```
                                       (SEQ ID NO: 1)
5'-GAA-3'

(SEQ ID NO: 6)
5'-GGCUUUCACUUAUCGUUGAUGGCUUC-3'

(SEQ ID NO: 7)
5'-CCAUCAACGAUAAGUGAAAGCC-3'
```

The aforementioned PK-0003 has a structure wherein, as shown by SEQ ID NO: 10 below, the aforementioned RNA shown by SEQ ID NO: 7, the aforementioned RNA shown by SEQ ID NO: 6, and the aforementioned RNA shown by SEQ ID NO: 1 are aligned in this order from the 5' side, and each RNA is linked via the aforementioned structure Lp. In addition, like PK-0055 in the aforementioned Example B1, the aforementioned RNA sequence shown by SEQ ID NO: 6 is complementary to the aforementioned RNA sequences shown by SEQ ID NOs: 1 and 7. Hence, the aforementioned PK-0003 performs self-annealing to have a stem structure, as shown in the formula below.

```
PK-0003
                                       (SEQ ID NO: 10)
5'-CCAUCAACGAUAAGUGAAAGCC-Lp-GGCUUUCACUUAUCGUUGAUG

GCUUC-Lp-GAA-3'

PK-0003
   GAA  CCAUCAACGAUAAGUGAAAGCC
Lp                                Lp
   CUUCGGUAGUUGCUAUUCACUUUCGG
```

Reference Example B2

In the same manner as with PK-0100 of the aforementioned Example B3 except that the aforementioned compound 22 was used instead of the aforementioned compound 18 (monomer in the present invention) in the aforementioned scheme 7, and the structure of the part corresponding to linker regions (Lx) and (Ly) was the aforementioned Lp (the aforementioned Reference Example B1) instead of the aforementioned Ll, a single-stranded RNA (ssRNA) was synthesized.

The ssRNA synthesized as mentioned above is hereafter referred to as PK-0071. The aforementioned PK-0071 has a structure wherein, as shown by SEQ ID NO: 66 below, the aforementioned RNA of SEQ ID NO: 64, the aforementioned RNA of SEQ ID NO: 63, and guanosine are aligned in this order from the 5' side, and each RNA and guanosine are linked via the aforementioned structure Lp. Furthermore, as also explained in the aforementioned Example B3, the aforementioned RNA sequence of SEQ ID NO: 63 is complementary to guanosine and the aforementioned RNA sequence of SEQ ID NO: 64. Hence, the aforementioned PK-0071 performs self-annealing to have a stem structure, as shown in the formula below.

```
                                       (SEQ ID NO: 63)
5'-GGAAUCGAAGUACUCAGCGUAAGUUC-3'

(SEQ ID NO: 64)
5'-ACUUACGCUGAGUACUUCGAUUCC-3'
```

-continued

Ex: PK-0071
(SEQ ID NO: 66)
5'-ACUUACGCUGAGUACUUCGAUUCC-Lp-GGAAUCGAAGUACUCAGC

GUAGUUC-Lp-G-3'

PK-0071
```
     G ACUUACGCUGAGUACUUCGAUUCC
Lp                               Lp
     CUUGAAUGCGACUCAUGAAGCUAAGG
```

Example C1

Inhibitory Effect on GAPDH Gene Expression in HCT116 Cells

Using the RNA of the present invention, inhibition of the GAPDH gene expression in vitro was examined.
(1) Materials and Method As RNA (Ex) of the present example, ssRNAs (PK-0054 and PK-0055) of the aforementioned Example B1 were used. As RNA of Reference Example, ssRNA (PK-0004 and PK-0003) of the aforementioned Reference Example B1 was also used. RNA solutions were prepared by dissolving each of the aforementioned RNAs in distilled water for injection (Otsuka Pharmaceutical Co., Ltd., hereinafter the same) to achieve the desired concentration (10 µmol/L).

HCT116 cells (DS Pharma Biomedical Co., Ltd.) were used as cells. A 10% FBS-containing McCoy's 5A (Invitrogen) medium was used as the medium. The culture conditions were set to 37° C. and 5% $CO_2$.

First, the HCT116 cells were cultured in the aforementioned medium, and the culture medium were dispensed to a 24-well plate so that each well contained 400 µL of the culture medium to achieve a density of $2\times10^4$ cells/well. The cells in the aforementioned wells were cultured for another 24 hours. Thereafter, the cells were transfected with the aforementioned RNA using a transfection reagent Lipofectamine 2000 (Invitrogen) according to the protocol with the aforementioned transfection reagent. Specifically, the transfection was carried out by setting the composition per well as follows. The final concentration of the aforementioned RNA in the aforementioned well was set to 1 nmol/L, 5 nmol/L, or 25 nmol/L.

TABLE 1

| (Composition per well: µL) | |
|---|---|
| culture medium | 400 |
| (A) Lipofectamine 2000 | 1.5 |
| (B) Opti-MEM (Invitrogen) | 98 |
| (C) RNA solution | 0.5 |
| Total | 500 |

After the transfection, the cells in the aforementioned wells were cultured for 48 hours, and then, the RNA was collected using an RNeasy Mini Kit (Qiagen, Netherlands) according to the protocol supplied therewith. Subsequently, cDNA was synthesized from the aforementioned RNA using a reverse transcriptase (trade name: SuperScript III, Invitrogen) according to the protocol supplied therewith. Then, as shown below, PCR was carried out using the aforementioned synthesized cDNA as a template, and the expression level of the GAPDH gene and that of the β-actin gene as an internal standard were measured. The aforementioned expression level of the GAPDH gene was normalized with reference to that of the β-actin gene mentioned above.

The aforementioned PCR was carried out using a Light-Cycler FastStart DNA Master SYBR Green I (trade name, Roche) as a reagent and a Light Cycler DX400 (trade name, Roche) as an instrument (hereinafter the same). The aforementioned GAPDH gene and β-actin gene were amplified using the following primer sets, respectively.

```
PCR primer set for GAPDH gene
                                    (SEQ ID NO: 11)
5'-GGAGAAGGCTGGGGCTCATTTGC-3'

(SEQ ID NO: 12)
5'-TGGCCAGGGGTGCTAAGCAGTTG-3'

Primer set for β-actin gene
                                    (SEQ ID NO: 13)
5'-GCCACGGCTGCTTCCAGCTCCTC-3'

(SEQ ID NO: 14)
5'-AGGTCTTTGCGGATGTCCACGTCAC-3'
```

As control 1, regarding the cells to which 100 µL of the aforementioned solution (B) only had been added, the expression levels of the genes also were measured (−). Furthermore, as control 2, regarding the cells subjected to the same transfection procedures as in the above except that the aforementioned RNA solution was not added and that the aforementioned (B) and 1.5 µL of the aforementioned (A) were added so that the total amount of (A) and (B) would be 100 µL, the expression level of the gene also was measured (mock).

As for the normalized expression level of the GAPDH gene, the relative value in the cell introduced with each RNA was determined based on the expression level in the cells of the control (−) set as 1.
(2) Results The results thereof are shown in FIG. 4. FIG. 4 is a graph showing the relative expression level of the GAPDH gene, and the vertical axis indicates the relative gene expression level.

As shown in FIG. 4, PK-0004 and PK-0054 showed an expression inhibitory effect since they incorporate a sequence targeting human GAPDH. In contrast, PK-0003 and PK-0055 having different sequences showed a low expression inhibitory effect as compared to PK-0004 and PK-0054. That is, these RNAs were superior in the reaction specificity for the target base sequence.

In addition, since PK-0054 is an ssRNA (single-stranded RNA), it can be produced easily and efficiently and was also superior in the handleability as compared to siRNA (double stranded RNA).

Furthermore, PK-0054 which is the ssRNA of Example showed is an expression inhibitory effect also equivalent to that of PK-0004 which is the ssRNA of Reference Example. The synthetic starting material is L-proline for PK-0004 and glycine for PK-0054, and the raw material of PK-0054 is easily obtained far more economically. Therefore, it is overwhelmingly advantageous in the convenience and the cost of the production.

Example C2

Inhibitory Effect on Expression of Firefly Luciferase Gene

Using the RNA of the present invention, inhibition of the firefly luciferase gene expression in vitro was examined.

(1) Materials and Method

As RNA (Ex) of the present example, ssRNA (PK0100) of the aforementioned Example B3 was used. As RNA of Reference Example, ssRNA (PK-0071) of the aforementioned Reference Example B2 was also used. RNA solutions were prepared by dissolving each of the aforementioned RNAs in distilled water for injection (Otsuka Pharmaceutical Co., Ltd. hereinafter the same) to achieve the desired concentration (10 μmol/L).

Breast cancer cell line MCF-7 stably expressing firefly luciferase (pGL3 Luc) was used, RPMI 1640 (Invitrogen)+ 10% FCS was used as the medium. The culture conditions were set to 37° C. and 5% $CO_2$.

More specifically, breast cancer cell line MCF-7 stably expressing firefly luciferase (pGL3 Luc) was cultured as follows.

[1] The aforementioned cells were cultured in the medium, and the culture medium was dispensed to a 96 well plate by 50 μL to $1\times10^4$ cells/well.

[2] Then, the aforementioned cells in the well were transfected with the RNA sample by using a transfection reagent Lipofectamine 2000 (Invitrogen) according to the attached protocol. Specifically, 50 μL/well of a complex of the aforementioned RNA sample and the aforementioned transfection reagent was added to the total amount of 100 μL, and the final concentration of the aforementioned RNA sample to 0.1, 1 or 10 nmol/L. As control 1, the cells to which the aforementioned RNA sample and the aforementioned transfection reagent were not added (−) were prepared and, as control 2, the cells to which the aforementioned RNA sample was not added in transfection but the aforementioned transfection reagent was added alone (mock) were prepared.

[3] The cells were further cultured for 24 hr after the aforementioned transfection.

The luciferase activity was measured as follows. The luciferase activity measurement is the measurement of an inhibitory effect on the expression of firefly luciferase gene, which is retained by the breast cancer cell line MCF-7 stably expressing firefly luciferase (pGL3 Luc).

[1] First, using Steady-Glo (trade name) Luciferase Assay System (Promega), the luminescence intensity of luciferase was measured by multilabel reader ARVO X2 (PerkinElmer) according to the attached protocol.

[2] The results of the luciferase activity measurement in the aforementioned [1] were presented as the relative activity to that of the cell free from addition of the RNA sample and the transfection reagent (−) (the aforementioned control 1, non-addition cell group) as 1.

(2) Results

Figure 12:
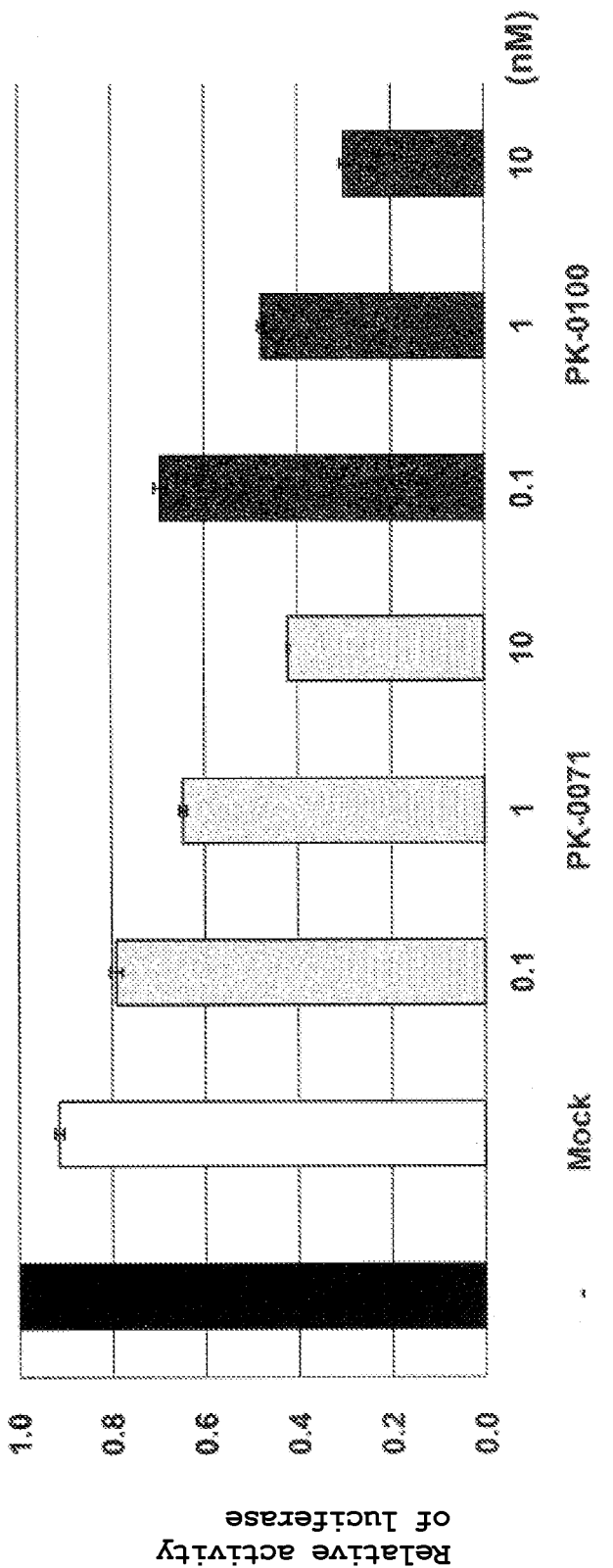
FIG. 12 is a graph showing the firefly luciferase gene expression inhibitory effect (relative activity of luciferase) of breast cancer cell line MCF-7 stably expressing firefly luciferase (pGL3 Luc) in the Example of the present invention.

The results are shown in FIG. 12. FIG. 12 is a graph showing the relative value of the luciferase activity.

As shown in FIG. 12, PK-0100 (sRNA of Example) could reduce the relative activity of luciferase to about 0.7-about 0.3. That is, PK-0100 showed a superior expression inhibitory effect on the firefly luciferase gene retained by the breast cancer cell line MCF-7 stably expressing firefly luciferase (pGL3 Luc). In addition, PK-0100 also showed an equivalent or more expression inhibitory effect on PK-0071, which is ssRNA of Reference Example.

Reference Example 1

Using ssRNAs having an unpaired base at different positions, inhibition of the GAPDH gene expression in vitro was examined.

(1) Materials and Method

As RNAs, ssRNAs shown in FIG. 5 were used. In FIG. 5, the numbers on the right indicate sequence identification numbers. In FIG. 5, from the 5' side, a region indicated with underlined lower-case letters is the aforementioned region (Xc); a region indicated with underlined upper-case letters is the aforementioned inner region (Z); and a region indicated with underlined lower-case letters is the aforementioned region (Yc). A region between the aforementioned Xc and Z is a linker region (Lx), and a region between the aforementioned Z and Yc is a linker region (Ly). Also, "Xc/Yc" indicates the ratio between the base length (Xc) of the aforementioned region (Xc) and the base length (Yc) of the aforementioned region (Yc). In FIG. 5, "*" indicates an unpaired base.

In each of the ssRNAs, the base length of the inner region (Z) was set to 26, the base length of the linker region (Lx) was set to 7, and the base length of the linker region (Ly) was set to 4. In NK-0036 and NK-0040, the total number of the bases (Xc+Yc) in the aforementioned regions (Xc) and (Yc) was set to 26. In the ssRNAs other than NK-0036 and NK-0040, the total number of the bases (Xc+Yc) in the aforementioned regions (Xc) and (Yc) was set to 25. Then, under these conditions, the base lengths of the aforementioned regions (Xc) and (Yc) were changed. As a result, NK-0036 and NK-0040 became the molecules without unpaired bases. Furthermore, each of the ssRNAs other than NK-0036 and NK-0040 became the molecule in which the aforementioned inner region (Z) includes only one unpaired base that does not form a double strand and the position of the aforementioned unpaired base in the aforementioned inner region (Z) was shifted from the 3' side to the 5' side.

Transfection into the HCT116 cells, culture, collection of RNA, synthesis of cDNA, and PCR were carried out in the same manner as in the aforementioned Example C1, except that each of the aforementioned RNAs was used, and the relative expression level of the GAPDH gene was determined. The RNA concentration at the time of the transfection was set to 10 nmol/L.

(2) Results and Consideration

Figure 6:
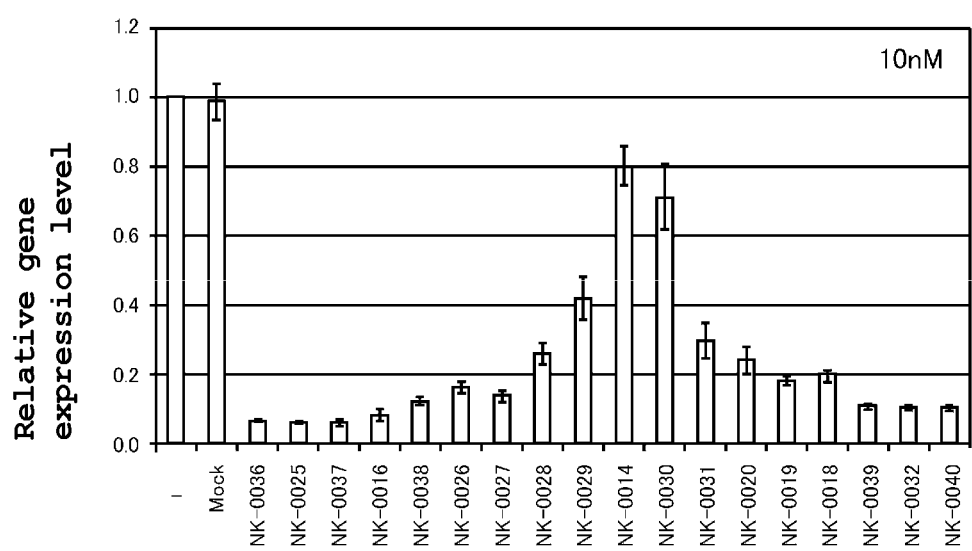
FIG. 6 is a graph showing the relative expression level of the GAPDH gene in a Reference Example.

The results thereof are shown in FIG. 6. FIG. 6 is a graph showing the relative expression level of the GAPDH gene when each of the RNAs was used at the final concentration of 10 nmol/L. As can be seen from FIG. 6, it was found that all the ssRNAs with the varied lengths of the aforementioned 5' side region (Xc) and the aforementioned 3' side region (Yc) inhibited the expression of the GAPDH gene.

In particular, it was found that, as the difference between the base length of the aforementioned region (Xc) and the base length of the aforementioned region (Yc) became greater, the expression level of the gene decreased relatively, i.e., the expression inhibitory activity increased. That is, it was found that, by setting the position of the unpaired base in the aforementioned inner region (Z) to be closer to the 5' side or the 3' side with respect to the middle of the aforementioned inner region, it is possible to improve the aforementioned expression inhibitory activity.

Reference Example 2

Using ssRNAs having an unpaired base at different positions, inhibition of the TGF-β1 gene expression in vitro was examined.

(1) Materials and Method

As RNAs, ssRNAs shown below were used. In the following sequences, "*" indicates an unpaired base.

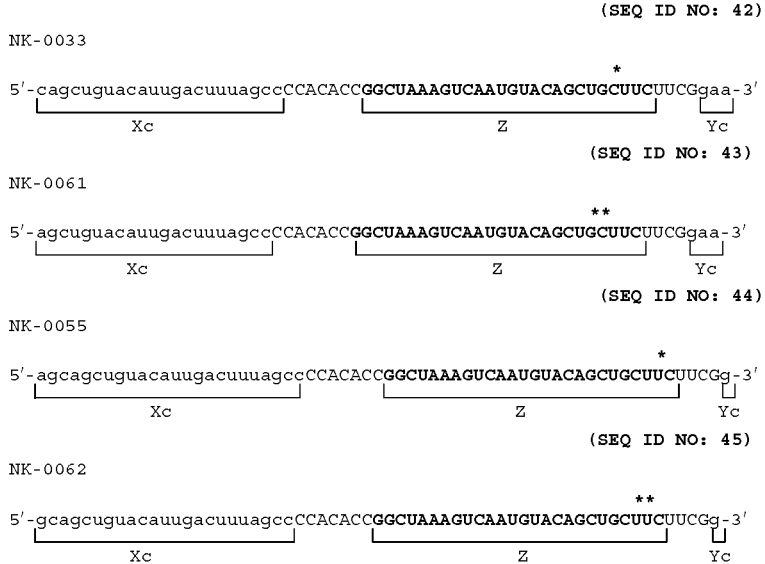

(1.2) Inhibition of Gene Expression

RNA solution was prepared by dissolving each of the aforementioned RNAs that had been cryopreserved in distilled water for injection to achieve a concentration of 20 µmol/L. Then, transfection of the aforementioned ssRNA to the Hepal-6 cells, collection of RNA, synthesis of cDNA and PCR were carried out in the same manner as in the aforementioned Example C1, except that the aforementioned RNA solution was used. The relative expression level of the TGF-β1 gene was determined. The RNA concentration at the time of the transfection was set to 1 nmol/L.

(2) Results

Figure 7:
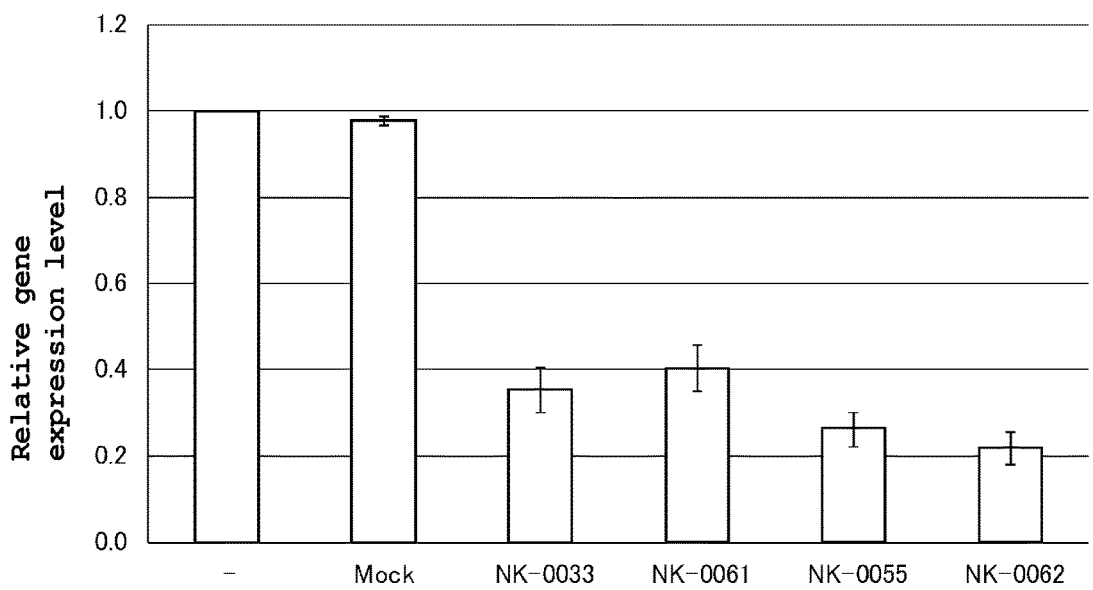
FIG. 7 is a graph showing the relative expression level of the TGF-β1 gene in a Reference Example.

The results thereof are shown in FIG. 7. FIG. 7 is a graph showing the relative expression level of the TGF-β1 gene. As can be seen from FIG. 7, these ssRNAs all exhibited gene-expression inhibitory activities. Furthermore, NK-0055 and NK-0062 in which the 2nd base and, the 3rd base from the 3' end of the aforementioned inner region (Z) are the unpaired bases, respectively, exhibited higher expression inhibitory activities than NK-0033 and NK-0061 in which the 4th base and the 5th base from the 3' end of the aforementioned inner region (Z) are the unpaired bases, respectively. These results agree with the behavior exhibited in the aforementioned Reference Example 1 directed to the different target gene.

Reference Example 3

Using ssRNAs having an unpaired base at different positions, inhibition of the LAMA1 gene expression in vitro was examined.

(1) Materials and Method

As RNA, ssRNAs shown below were used. In the following sequences, "*" indicates an unpaired base.

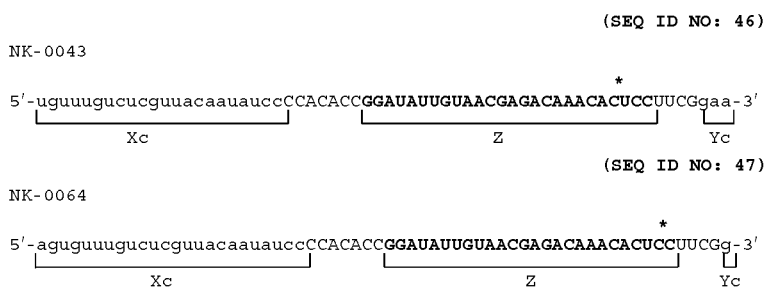

Transfection to 293 cells was carried out in the same manner as in the aforementioned Example C1, except that each of the aforementioned RNAs was used, and the aforementioned cells were cultured for 48 hours. The RNA concentration at the time of the transfection was set to 10 nmol/L. Then, collection of RNA, synthesis of cDNA, and PCR were carried out in the same manner as in the aforementioned Example C1, except that a primer set for the LAMA1 gene shown below were used as primer, and the expression level of the LAMA1 gene and that of the β-actin gene as an internal standard were measured. The aforementioned expression level of the LAMA1 gene was normalized with reference to that of the β-actin gene as the internal standard.

```
Primer set for LAMA1 gene
                                 (SEQ ID NO: 48)
5'-AAAGCTGCCAATGCCCCTCGACC-3'

(SEQ ID NO: 49)
5'-TAGGTGGGTGGCCCTCGTCTTG-3'
```

Figure 8:
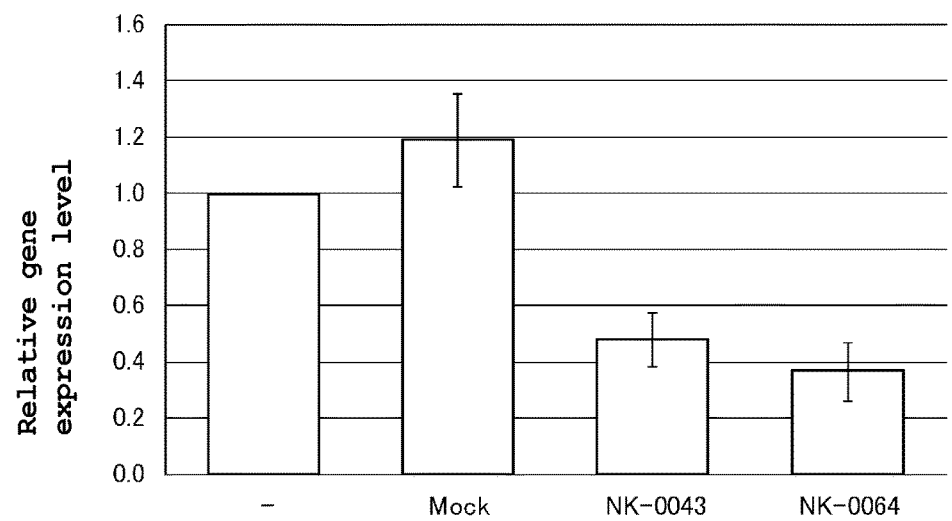
FIG. 8 is a graph showing the relative expression level of the LAMA gene in a Reference Example.

The expression level of control 1 (−) and control 2 (mock) was also measured in the same manner as in the aforementioned Example C1. As for the normalized expression level of the LAMA1 gene, the relative value in the cell introduced with each RNA was determined based on the expression level in the cells of the control (−) set as 1.
(2) Results The results thereof are shown in FIG. 8. FIG. 8 is a graph showing the relative expression level of the LAMA1 gene in the 293 cells. As can be seen from FIG. 8, these ssRNAs all exhibited gene-expression inhibitory activities. Furthermore, NK-0064 in which the 2nd base from the 3' end of the aforementioned inner region (Z) is the unpaired base exhibited a higher expression inhibitory activity than NK-0043 in which the 4th base from the 3' end of the aforementioned inner region (Z) is the unpaired base. These results agree with the behaviors exhibited in the aforementioned Reference Examples 1 and 2 directed to the different target genes.

Reference Example 4

Using ssRNAs having an unpaired base at different positions, inhibition of the LMNA gene expression in vitro was examined.
(1) Materials and Method As RNA, ssRNAs shown below were used. In the following sequences, "*" indicates an unpaired base.

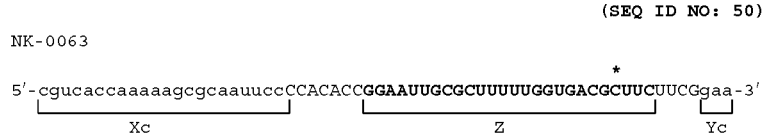

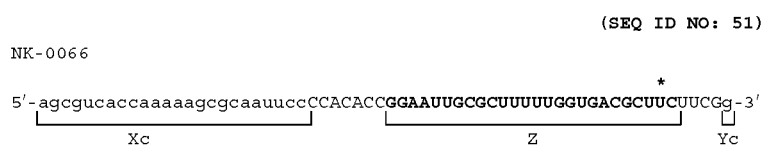

Transfection to A549 cells was carried out in the same manner as in the aforementioned Example C1, except that each of the aforementioned RNAs was used, and the aforementioned cells were cultured for 48 hours. The RNA concentration at the time of the transfection was set to 3 nmol/L. Then, collection of RNA, synthesis of cDNA, and PCR were carried out in the same manner as in the aforementioned Example C1, except that a primer set for the LMNA gene shown below was used as primer, and the expression level of the LMNA gene and that of the β-actin gene as an internal standard were measured. The aforementioned expression level of the LMNA gene was normalized with reference to that of the β-actin gene as the internal standard.

```
Primer set for LMNA gene
                                 (SEQ ID NO: 52)
5'-CTGGACATCAAGCTGGCCCTGGAC-3'

(SEQ ID NO: 53)
5'-CACCAGCTTGCGCATGGCCACTTC-3'
```

The expression level of control 1 (−) and control 2 (mock) was also measured in the same manner as in the aforementioned Example C1. As for the normalized expression level of the LMNA gene, the relative value in the cell introduced with each RNA was determined based on the expression level in the cells of the control (−) set as 1.
(2) Results The results thereof are shown in FIG. 9. FIG. 9 is a graph showing the relative expression level of the LMNA gene in the A549 cells. As can be seen from FIG. 9, these ssRNAs all exhibited gene-expression inhibitory activities. Furthermore, NK-0066 in which the 2nd base from the 3' end of the aforementioned inner region (Z) is the unpaired base exhibited a higher expression inhibitory activity than NK-0063 in which the 4th base from the 3' end of the aforementioned inner region (Z) is the unpaired base. These results agree with the behaviors exhibited in the aforementioned Reference Examples 1 to 3 directed to the different target genes.

From the results obtained in Reference Examples 1 to 4, it is clear that, for example, regarding the position of the unpaired base, similar behaviors are exhibited regardless of the kind of a target gene and an expression inhibitory sequence for the target gene. Furthermore, it has already been described above that the aforementioned Example C1 exhibited a similar behavior to those of the Reference Examples.

Reference Example 5

Using ssRNAs with the length of each of the aforementioned inner 5' side region (X), the aforementioned 5' side region (Xc), the aforementioned inner 3' side region (Y), and the aforementioned 3' side region (Yc) being varied, inhibition of the GAPDH gene expression in vitro was examined.
(1) Materials and Method As RNAs, ssRNAs shown in FIG. 10 were used. In FIG. 10, the numbers on the right indicate the sequence identification numbers. In FIG. 10, from the 5' side, a region indicated with underlined lower-case letters is the aforementioned region (Xc); a region indicated with underlined upper-case letters is the aforementioned inner region (Z); and a region indicated with underlined lower-case letters is the aforementioned region (Yc). Also, "Xc+Yc/X+Y" indicates the ratio between the total base length of the aforementioned regions (Xc) and (Yc) and the total base length of the aforementioned regions (X) and (Y). In FIG. 10, "*" indicates an unpaired base.

In each of the ssRNAs, the base length of the linker region (Lx) was set to 7, the base length of the linker region (Ly) was set to 4, the base length of the aforementioned region (Yc) was set to 1, and the 2nd base from the 3' side of the aforementioned inner region (Z) was set to be an unpaired base. Then, the base length of the aforementioned inner region (Z) and the base length of the aforementioned region (Xc) were changed.

Unless otherwise specified, transfection of the aforementioned RNAs into HCT116 cells, culture, collection of RNA, synthesis of cDNA, and PCR were carried out in the same manner as in the aforementioned Example C1, and the relative value of the expression level of the GAPDH gene was calculated. In the conditions for the aforementioned transfection, the aforementioned composition per well was the same as that in the following Table 2.

TABLE 2

| (Composition per well: µL) | |
|---|---|
| culture medium | 400 |
| (A) Lipofectamine 2000 | 1.5 |
| (B) + (C) | 98.5 |
| Total | 500 |

(2) Results and Consideration

Figure 11:
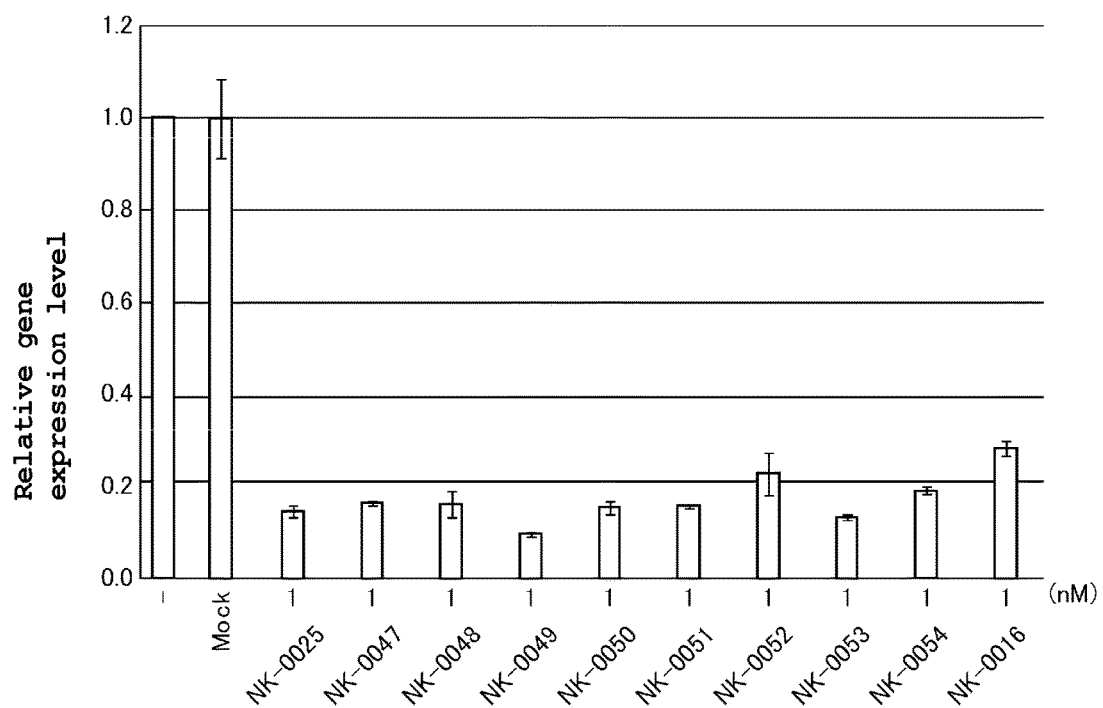
FIG. 11 is a graph showing the relative expression level of the GAPDH gene in a Reference Example.

The results thereof are shown in FIG. 11. FIG. 11 is a graph showing the relative expression level of the GAPDH gene when each of the RNAs was used at the final concentration of 1 nmol/L. As can be seen from FIG. 11, it was found that all the ssRNAs with the varied lengths of the aforementioned regions (X), (Xc), (Y), and (Yc) inhibited the expression of the GAPDH gene.

While the present invention has been described above with reference to illustrative embodiments, the present invention is by no means limited thereto. Various changes that may become apparent to those skilled in the art may be made in the configuration and specifics of the present invention without departing from the scope of the present invention.

INDUSTRIAL APPLICABILITY

The ssPN molecule of the present invention can inhibit gene expression. Since it is not circular, synthesis thereof is easy. Since it is a single strand that does not require an annealing step for a double strand, it can be produced efficiently. Moreover, since the aforementioned linker region contains the aforementioned non-nucleotide residue, for example, conventional alteration of nucleotide residue is not the limited option but, for example, alteration such as modification of the aforementioned linker region and the like is also possible. Thus, since the ssPN molecule of the present invention can inhibit the expression of a target gene as described above, it is useful as, for example, a pharmaceutical product, a diagnostic agent, an agricultural chemical, and a tool for conducting research on medical science, life science, and the like.

The invention claimed is:

1. A single-stranded nucleic acid molecule comprising an expression inhibitory sequence that inhibits expression of a target gene, and comprising region (X), region (Y), linker region (Lx), linker region (Ly), region (Xc) and region (Yc), wherein
the linker region (Lx) is linked between the region (X) and the region (Xc),
the linker region (Ly) is linked between the region (Y) and the region (Yc),
the region (Xc) is complementary to the region (X),
the region (Yc) is complementary to the region (Y),
an inner region (Z) is composed of the region (X) and the region (Y) that are linked to each other,
at least one of the region (Z), the region (Xc) and the region (Yc) contains the expression inhibitory sequence, and
the linker region (Lx) and the linker region (Ly) are represented by the following formula (I-1) or (I-4) wherein n is an integer of 0-30 and m is an integer of 0-30:

(I-1)

(I-4)

2. The single-stranded nucleic acid molecule according to claim 1, wherein the number of bases (X) in the region (X) and the number of bases (Xc) in the region (Xc) satisfy the condition of the following formula (3) or (5):

$$X > Xc \tag{3}$$

$$X = Xc \tag{5}$$

3. The single-stranded nucleic acid molecule according to claim 1, wherein the number of bases (X) in the region (X) and the number of bases (Xc) in the region (Xc) satisfy the condition of the following formula (11):

$$X - Xc = 1, 2 \text{ or } 3 \tag{11}$$

4. The single-stranded nucleic acid molecule according to claim 1, wherein the number of bases (Xc) in the region (Xc) is 19 to 30.

5. The single-stranded nucleic acid molecule according to claim 1, wherein, in the formula (I-1), n =11 and m =12.

6. The single-stranded nucleic acid molecule according to claim 1, wherein, in the formula (I-1), n=5 and m=4.

7. The single-stranded nucleic acid molecule according to claim 1, wherein, in the formula (I-4), n=5 and m=4.

8. The single-stranded nucleic acid molecule according to claim 1, wherein the number of bases (X) in the region (X), the number of bases (Y) in the region (Y), the number of bases (Xc) in the region (Xc) and the number of bases (Yc) in the region (Yc) satisfy the condition of the following formula (2):

$$Z \geq Xc + Yc \tag{2}$$

9. The single-stranded nucleic acid molecule according to claim 1, wherein the number of bases (X) in the region (X), the number of bases (Xc) in the (Xc), the number of bases (Y) in the region (Y), and the number of bases (Yc) in the region (Yc) satisfy any of the following conditions (a) to (d):
(a) conditions of the following formula (3) and (4) are satisfied;

$$X > Xc \tag{3}$$

$$Y = Yc \tag{4}$$

(b) conditions of the following formula (5) and (6) are satisfied;

$$X = Xc \tag{5}$$

$$Y > Yc \tag{6}$$

(c) conditions of the following formula (7) and (8) are satisfied;

$$X > Xc \tag{7}$$

$$Y > Yc \tag{8}$$

(d) conditions of the following formula (9) and (10) are satisfied;

$$X=Xc \qquad (9)$$

$$Y=Yc \qquad (10).$$

10. The single-stranded nucleic acid molecule according to claim 9, wherein, in the conditions (a) to (d), the difference between the number of bases (X) in the region (X) and the number of bases (Xc) in the region (Xc), and the difference between the number of bases (Y) in the region (Y) and the number of bases (Yc) in the region (Yc) satisfy the following conditions:

(a) conditions of the following formula (11) and (12) are satisfied;

$$X-Xc=1, 2 \text{ or } 3 \qquad (11)$$

$$Y-Yc=0 \qquad (12)$$

(b) conditions of the following formula (13) and (14) are satisfied;

$$X-Xc=0 \qquad (13)$$

$$Y-Yc=1, 2 \text{ or } 3 \qquad (14)$$

(c) conditions of the following formula (15) and (16) are satisfied;

$$X-Xc=1, 2 \text{ or } 3 \qquad (15)$$

$$Y-Yc=1, 2 \text{ or } 3 \qquad (16)$$

(d) conditions of the following formula (17) and (18) are satisfied;

$$X-Xc=0 \qquad (17)$$

$$Y-Yc=0 \qquad (18).$$

11. The single-stranded nucleic acid molecule according to claim 1, wherein the number of bases (Xc) in the region (Xc) is 1 to 11.

12. (The single-stranded nucleic acid molecule according to claim 11, wherein the number of bases (Xc) in the region (Xc) is 1 to 7.

13. The single-stranded nucleic acid molecule according to claim 11, wherein the number of bases (Xc) in the region (Xc) is 1 to 3.

14. The single-stranded nucleic acid molecule according to claim 1, wherein the number of bases (Yc) in the region (Yc) 1 to 11.

15. The single-stranded nucleic acid molecule according to claim 14, wherein the number of bases (Yc) in the region (Yc) is 1 to 7.

16. The single-stranded nucleic acid molecule according to claim 14, wherein the number of bases (Yc) in the region (Yc) is 1 to 3.

17. The single-stranded nucleic acid molecule according to claim 1, wherein the single-stranded nucleic acid molecule comprises at least one modified residue.

18. The single-stranded nucleic acid molecule according to claim 1, further comprising a labeling substance.

19. The single-stranded nucleic acid molecule according to claim 1, further comprising a stable isotope.

20. The single-stranded nucleic acid molecule according to claim 1, which is an RNA molecule.

21. The single-stranded nucleic acid molecule according to claim 1, wherein the total number of bases in the single-stranded nucleic acid molecule is 50 or more.

22. The single-stranded nucleic acid molecule according to claim 1, wherein expression of the gene is inhibited by RNA interference.

23. A pharmaceutical composition comprising:
the single-stranded nucleic acid molecule according to claim 1, and a pharmaceutically acceptable additive.

24. A monomer for nucleic acid molecule synthesis, having the structure of the following formula (II-1) or (II-4):

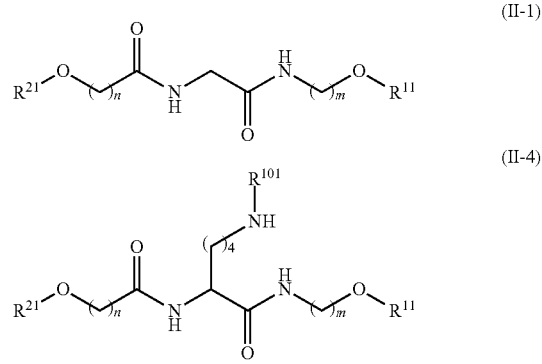

wherein $R^{11}$ and $R^{21}$ are each independently H, a protecting group or a phosphate-protecting group, in the formula (II-4), $R^{101}$ is, independently from $R^{11}$ and $R^{21}$, H, a protecting group or a phosphate-protecting group, in the formula (II-1), n=11 and m=12 or n=5 and m=4 and in the formula (II-4), n=5 and m=4.

25. The monomer according to claim 24, further comprising a labeling substance.

26. The monomer according to claim 24, further comprising a stable isotope.

27. A method for inhibiting expression of a target gene, comprising the step of:
administering the single-stranded nucleic acid molecule according to claim 1 to a cell, a tissue, or an organ.

28. The method according to claim 27, wherein the single-stranded nucleic acid molecule is administered in vivo or in vitro.

29. The method according to claim 27, wherein expression of the gene is inhibited by RNA interference.

30. The method according to claim 28, wherein the single-stranded nucleic acid molecule is administered to a subject suffering from inflammation in vivo, and wherein the target gene is TGF-β1 gene.

31. A method of producing the nucleic acid molecule according to claim 1, which comprises the steps of:
linking the region (X) of a nucleic acid consisting of the inner region (Z) and a nucleic acid consisting of the region (Xc) via a monomer consisting of the linker region (Lx) such that the region (X) and the region (Xc) form a complementary double-stranded structure, and
linking the region (Y) of the nucleic acid consisting of the inner region (Z) and a nucleic acid consisting of the region (Yc) via a monomer consisting of the linker region (Ly) such that the region (Y) and the region (Yc) form a complementary double-stranded structure.

* * * * *

SEQUENCE LISTING

<160> NUMBER OF SEQ ID NOS: 66

<210> SEQ ID NO 1
<211> LENGTH: 3
<212> TYPE: RNA
<213> ORGANISM: Artificial Sequence
<220> FEATURE:
<223> OTHER INFORMATION: synthetic RNA

<400> SEQUENCE: 1 gaa                                                                       3

<210> SEQ ID NO 2
<211> LENGTH: 26
<212> TYPE: RNA
<213> ORGANISM: Artificial Sequence
<220> FEATURE:
<223> OTHER INFORMATION: synthetic nucleic acid molecule

<400> SEQUENCE: 2
ggcuguuguc auacuucuca ugguuc                                              26

<210> SEQ ID NO 3
<211> LENGTH: 22
<212> TYPE: RNA
<213> ORGANISM: Artificial Sequence
<220> FEATURE:
<223> OTHER INFORMATION: synthetic nucleic acid molecule

<400> SEQUENCE: 3
caugagaagu augacaacag cc                                                  22

<210> SEQ ID NO 4
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 4
caugagaagu augacaacag ccggcuguug ucauacuucu caugguucga a        51

<210> SEQ ID NO 5
<211> LENGTH: 19
<212> TYPE: RNA
<213> ORGANISM: Artificial Sequence
<220> FEATURE:
<223> OTHER INFORMATION: synthetic expression inhibiting region

<400> SEQUENCE: 5 guugcauac uucucaugg        19

<210> SEQ ID NO 6
<211> LENGTH: 26
<212> TYPE: RNA
<213> ORGANISM: Artificial Sequence
<220> FEATURE:
<223> OTHER INFORMATION: synthetic nucleic acid molecule

<400> SEQUENCE: 6
ggcuuucacu uaucguugau ggcuuc        26

<210> SEQ ID NO 7
<211> LENGTH: 22
<212> TYPE: RNA
<213> ORGANISM: Artificial Sequence
<220> FEATURE:
<223> OTHER INFORMATION: synthetic nucleic acid molecule

<400> SEQUENCE: 7
ccaucaacga uaagugaaag cc        22

<210> SEQ ID NO 8
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 8
ccaucaacga uaagugaaag ccggcuuuca cuuaucguug auggcuucga a        51

<210> SEQ ID NO 9
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 9
caugagaagu augacaacag ccggcuguug ucauacuucu caugguucga a        51

<210> SEQ ID NO 10
<211> LENGTH: 51
<212> TYPE: RNA
<213> ORGANISM: Artificial Sequence
<220> FEATURE:

<223> OTHER INFORMATION: synthetic nucleic acid molecule

<400> SEQUENCE: 10
ccaucaacga uaagugaaag ccggcuuuca cuuaucguug auggcuucga a        51

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
ggagaaggct ggggctcatt tgc        23

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
tggccagggg tgctaagcag ttg        23

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
gccacggctg cttccagctc ctc        23

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
aggtctttgc ggatgtccac gtcac        25

<210> SEQ ID NO 15
<211> LENGTH: 21
<212> TYPE: RNA
<213> ORGANISM: Artificial Sequence
<220> FEATURE:
<223> OTHER INFORMATION: synthetic expression inhibiting sequence

<400> SEQUENCE: 15
aaagucaaug uacagcugcu u        21

<210> SEQ ID NO 16
<211> LENGTH: 19
<212> TYPE: RNA
<213> ORGANISM: Artificial Sequence
<220> FEATURE:
<223> OTHER INFORMATION: synthetic expression inhibiting sequence

<400> SEQUENCE: 16
auuguaacga gacaaacac        19

```
<210> SEQ ID NO 17
<211> LENGTH: 19
<212> TYPE: RNA
<213> ORGANISM: Artificial Sequence
<220> FEATURE:
<223> OTHER INFORMATION: synthetic expression inhibiting sequence

<400> SEQUENCE: 17
uugcgcuuuu uggugacgc                                                    19

<210> SEQ ID NO 18
<211> LENGTH: 48
<212> TYPE: RNA
<213> ORGANISM: Artificial Sequence
<220> FEATURE:
<223> OTHER INFORMATION: synthetic nucleic acid molecule

<400> SEQUENCE: 18
ccaugagaag uaugacaaca gccggcuguu gucauacuuc ucaugguu                    48

<210> SEQ ID NO 19
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 19
cagcuguaca uugacuuuag ccggcuaaag ucaauguaca gcugcuucga a                51

<210> SEQ ID NO 20
<211> LENGTH: 50
<212> TYPE: RNA
<213> ORGANISM: Artificial Sequence
<220> FEATURE:
<223> OTHER INFORMATION: synthetic nucleic acid molecule

<400> SEQUENCE: 20
agcuguacau ugacuuuagc cggcuaaagu caauguacag cugcuucgaa                  50

<210> SEQ ID NO 21
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 21
agcagcugua cauugacuuu agccggcuaa agucaaugua cagcugcuuc g                51

<210> SEQ ID NO 22
<211> LENGTH: 50
<212> TYPE: RNA
<213> ORGANISM: Artificial Sequence
<220> FEATURE:
<223> OTHER INFORMATION: synthetic nucleic acid molecule

<400> SEQUENCE: 22
gcagcuguac auugacuuua gccggcuaaa gucaauguac agcugcuucg                  50

<210> SEQ ID NO 23
<211> LENGTH: 51
<212> TYPE: RNA
<213> ORGANISM: Artificial Sequence
<220> FEATURE:
<223> OTHER INFORMATION: synthetic nucleic acid molecule
```

-continued

<400> SEQUENCE: 23
ugucagugcu cauuuacaag ccggcuugua aaugagcacu gacacuucga a    51

<210> SEQ ID NO 24
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 24
aaccaugaga aguaugacaa cagccccaca ccggcuguug ucauacuucu caugguucuu    60
cg    62

<210> SEQ ID NO 25
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 25
accaugagaa guaugacaac agccccacac cggcuguugu cauacuucuc augguucuuc    60
gg    62

<210> SEQ ID NO 26
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 26
ccaugagaag uaugacaaca gccccacacc ggcuguuguc auacuucuca ugguucuucg    60
ga    62

<210> SEQ ID NO 27
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 27
caugagaagu augacaacag ccccacaccg gcuguuguca uacuucaugu gguucucgg    60 aa    62

<210> SEQ ID NO 28
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 28
augagaagua ugacaacagc cccacaccgg cuguugucau acuucucaug guucuucgga    60
ac    62

<210> SEQ ID NO 29
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 29
ugagaaguau gacaacagcc ccacaccggc uguugucaua cuucucaugg uucuucggaa    60
cc    62

<210> SEQ ID NO 30
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 30
agaaguauga caacagcccc acaccggcug uugucauacu cucaugguu cuucggaacc    60 au    62

<210> SEQ ID NO 31
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 31
aaguaugaca acagccccac accggcuguu gucauacuuc caugguucu ucggaaccau    60 ga    62

<210> SEQ ID NO 32
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 32
guaugacaac agccccacac cggcuguugu cauacuucuc augguucuuc ggaaccauga    60
ga    62

<210> SEQ ID NO 33
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 33
augacaacag ccccacaccg gcuguuguca uacuucucau gguucuucgg aaccaugaga    60
ag    62

<210> SEQ ID NO 34
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 34
acaacagccc cacaccggcu guugucauac uucucauggu cuucggaac caugagaagu    60 au    62

<210> SEQ ID NO 35
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 35
aacagcccca caccggcugu ugucauacuu cucaugguuc uucggaacca ugagaaguau    60
ga                                                                  62

<210> SEQ ID NO 36
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 36
cagccccaca ccggcuguug ucauacuucu caugguucuu cggaaccaug agaaguauga    60
ca                                                                  62

<210> SEQ ID NO 37
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 37
agccccacac cggcuguugu cauacuucuc augguucuuc ggaaccauga aguaugac     60 aa                                                                  62

<210> SEQ ID NO 38
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 38
gccccacacc ggcuguuguc auacuucuca ugguucuucg gaaccaugag aaguaugaca    60
ac                                                                  62

<210> SEQ ID NO 39
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 39
ccccacaccg gcuguuguca uacuucucau gguucuucgg aaccaugaga aguaugacaa    60
ca                                                                  62

<210> SEQ ID NO 40
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 40

```
cccacaccgg cuguugucau acuucucaug guucuucgga accaugagaa guaugacaac    60
ag                                                                  62

<210> SEQ ID NO 41
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 41
ccacaccggc uguugucaua cuucucaugg uucuucggaa ccaugagaag uaugacaaca    60
gc                                                                  62

<210> SEQ ID NO 42
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 42
cagcuguaca uugacuuuag ccccacaccg gcuaaaguca auguacagcu gcuucuucgg    60
aa                                                                  62

<210> SEQ ID NO 43
<211> LENGTH: 61
<212> TYPE: RNA
<213> ORGANISM: Artificial Sequence
<220> FEATURE:
<223> OTHER INFORMATION: synthetic nucleic acid molecule

<400> SEQUENCE: 43
agcuguacau ugacuuuagc cccacaccgg cuaaagucaa uguacagcug cuucuucgga    60
a                                                                   61

<210> SEQ ID NO 44
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 44
agcagcugua cauugacuuu agccccacac cggcuaaagu caauguacag cugcuucuuc    60
gg                                                                  62

<210> SEQ ID NO 45
<211> LENGTH: 61
<212> TYPE: RNA
<213> ORGANISM: Artificial Sequence
<220> FEATURE:
<223> OTHER INFORMATION: synthetic nucleic acid molecule

<400> SEQUENCE: 45
gcagcuguac auugacuuua gccccacacc ggcuaaaguc aauguacagc ugcuucuucg    60
g                                                                   61

<210> SEQ ID NO 46
<211> LENGTH: 62
<212> TYPE: RNA
```

```
<213> ORGANISM: Artificial Sequence
<220> FEATURE:
<223> OTHER INFORMATION: synthetic nucleic acid molecule

<400> SEQUENCE: 46 uguuugcuc guuacaauau ccccacaccg gauauuguaa cgagacaaac acuccuucgg       60
ga                                                                    62

<210> SEQ ID NO 47
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 47
aguguuuguc ucguuacaau auccccacac cggauauugu aacgagacaa acacuccuuc      60
gg                                                                    62

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
aaagctgcca atgcccctcg acc                                             23

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
taggtgggtg gccctcgtct tg                                              22

<210> SEQ ID NO 50
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 50
cgucaccaaa aagcgcaauu ccccacaccg gaauugcgcu uuuggugac gcuucuucgg       60 aa                                                                    62

<210> SEQ ID NO 51
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 51
agcgucacca aaaagcgcaa uuccccacac cggaauugcg cuuuuggug acgcuucuuc       60 gg                                                                    62

<210> SEQ ID NO 52
<211> LENGTH: 24
```

```
<212> TYPE: DNA
<213> ORGANISM: Artificial Sequence
<220> FEATURE:
<223> OTHER INFORMATION: primer

<400> SEQUENCE: 52
ctggacatca agctggccct ggac                                           24

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
caccagcttg cgcatggcca cttc                                           24

<210> SEQ ID NO 54
<211> LENGTH: 64
<212> TYPE: RNA
<213> ORGANISM: Artificial Sequence
<220> FEATURE:
<223> OTHER INFORMATION: synthetic nucleic acid molecule

<400> SEQUENCE: 54
aaccaugaga aguaugacaa cagccccaca ccggcuguug ucauacuucu caugguucgu    60
ucgc                                                                 64

<210> SEQ ID NO 55
<211> LENGTH: 62
<212> TYPE: RNA
<213> ORGANISM: Artificial Sequence
<220> FEATURE:
<223> OTHER INFORMATION: synthetic nucleic acid molecule

<400> SEQUENCE: 55
accaugagaa guaugacaac agccccacac cggcuguugu cauacuucuc augguucuuc    60
gg                                                                   62

<210> SEQ ID NO 56
<211> LENGTH: 60
<212> TYPE: RNA
<213> ORGANISM: Artificial Sequence
<220> FEATURE:
<223> OTHER INFORMATION: synthetic nucleic acid molecule

<400> SEQUENCE: 56
accaugagaa guaugacaac agcccacacc gcuguuguca uacuucucau gguucuucgg    60

<210> SEQ ID NO 57
<211> LENGTH: 58
<212> TYPE: RNA
<213> ORGANISM: Artificial Sequence
<220> FEATURE:
<223> OTHER INFORMATION: synthetic nucleic acid molecule

<400> SEQUENCE: 57
ccaugagaag uaugacaaca gcccacaccg cuguugucau acuucucaug guuucga       58

<210> SEQ ID NO 58
<211> LENGTH: 58
<212> TYPE: RNA
<213> ORGANISM: Artificial Sequence
<220> FEATURE:
```

<223> OTHER INFORMATION: synthetic nucleic acid molecule

<400> SEQUENCE: 58
accaugagaa guaugacaac agccacaccc uguugucaua cuucucaugg uucuucgg        58

<210> SEQ ID NO 59
<211> LENGTH: 56
<212> TYPE: RNA
<213> ORGANISM: Artificial Sequence
<220> FEATURE:
<223> OTHER INFORMATION: synthetic nucleic acid molecule

<400> SEQUENCE: 59
ccaugagaag uaugacaaca gccacacccu guugucauac uucucauggu uuucga          56

<210> SEQ ID NO 60
<211> LENGTH: 54
<212> TYPE: RNA
<213> ORGANISM: Artificial Sequence
<220> FEATURE:
<223> OTHER INFORMATION: synthetic nucleic acid molecule

<400> SEQUENCE: 60
caugagaagu augacaacag ccacacccug uugucauacu ucucaugguu ucga            54

<210> SEQ ID NO 61
<211> LENGTH: 54
<212> TYPE: RNA
<213> ORGANISM: Artificial Sequence
<220> FEATURE:
<223> OTHER INFORMATION: synthetic nucleic acid molecule

<400> SEQUENCE: 61
ccaugagaag uaugacaaca ccacaccugu ugcauacuu cucauggu uu ucga            54

<210> SEQ ID NO 62
<211> LENGTH: 52
<212> TYPE: RNA
<213> ORGANISM: Artificial Sequence
<220> FEATURE:
<223> OTHER INFORMATION: synthetic nucleic acid molecule

<400> SEQUENCE: 62
caugagaagu augacaacac cacaccuguu gucauacuuc caugguuuc ga               52

<210> SEQ ID NO 63
<211> LENGTH: 26
<212> TYPE: RNA
<213> ORGANISM: Artificial Sequence
<220> FEATURE:
<223> OTHER INFORMATION: synthetic nucleic acid molecule

<400> SEQUENCE: 63
ggaaucgaag uacucagcgu aaguuc                                            26

<210> SEQ ID NO 64
<211> LENGTH: 24
<212> TYPE: RNA
<213> ORGANISM: Artificial Sequence
<220> FEATURE:
<223> OTHER INFORMATION: synthetic nucleic acid molecule

<400> SEQUENCE: 64
acuuacgcug aguacuucga uucc                                              24

```
<210> SEQ ID NO 65
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 65
acuuacgcug aguacuucga uuccggaauc gaaguacuca gcguaaguuc g          51

<210> SEQ ID NO 66
<211> LENGTH: 51
<212> TYPE: RNA
<213> ORGANISM: Artificial Sequence
<220> FEATURE:
<223> OTHER INFORMATION: synthetic nucleic acid molecule

<400> SEQUENCE: 66
acuuacgcug aguacuucga uuccggaauc gaaguacuca gcguaaguuc g          51
```